US007268275B2

(12) United States Patent
ffrench-Constant et al.

(10) Patent No.: US 7,268,275 B2
(45) Date of Patent: Sep. 11, 2007

(54) **TCDB2 PROTEIN FROM *PHOTORHABDUS LUMINESCENS* W-14**

(75) Inventors: Richard H. ffrench-Constant, Bath (GB); Nicholas R. Waterfield, Bath (GB)

(73) Assignee: University of Bath (GB)

( * ) Notice: Subject to any disclaimer, the term of this patent is extended or adjusted under 35 U.S.C. 154(b) by 130 days.

(21) Appl. No.: 10/706,424

(22) Filed: Nov. 12, 2003

(65) Prior Publication Data
US 2004/0103455 A1 May 27, 2004

Related U.S. Application Data

(60) Provisional application No. 60/425,672, filed on Nov. 12, 2002.

(51) Int. Cl.
*A01H 5/00* (2006.01)
*A01H 5/10* (2006.01)
*C12N 15/82* (2006.01)
*C12N 15/31* (2006.01)
*C12P 21/04* (2006.01)

(52) U.S. Cl. .................... 800/302; 536/23.7; 435/418; 435/70.1

(58) Field of Classification Search .................... None
See application file for complete search history.

(56) References Cited

U.S. PATENT DOCUMENTS 6,281,413 B1 * 8/2001 Kramer et al. .............. 800/302
2002/0078478 A1 6/2002 Ffrench-Constant et al.

FOREIGN PATENT DOCUMENTS

WO WO 01/11029 A 2/2001

OTHER PUBLICATIONS

Waterfield et al 2001, Trends Microbiol. 9:185-191.*
Waterfield et al 2001, Appl. Environ. Microbiol. 67:5017-5024.*
DATABASE EMBL 'Online! , Oct. 27, 2001, XP002290086 retrieved from EBI Database accession No. AF346500 abstract.
Waterfield N. R. et. al.: "The tc genes of Photorhabdus: A growing family" Trends in Microbiology, Elsevier Science Ltd., Kidlington, GB, vol. 9, No. 4, Apr. 2001, pp. 181-191 xp002221683.
Ffrench-Constant R H et al: "A genomic sample sequence of the entomopathogenic bacterium *Photorhabdus luminescens* W14: Potential implications for virulence" Applied and Environmental Microbiology, Washington, DC US, vol. 66, No. 8, Aug. 2000, pp. 3310-3329.
Waterfield N. et al: "Oral toxicity of *Photorhabdus luminescens* W14 toxin complexes in *Escherichia coli*" Applied Environmental Microbiology, Washington, DC, US, vol. 67, No. 11, Nov. 2001, pp. 5017-5024.
Ffrench-Constant R et al: "Photorohabdus toxins: novel biological insecticides." Current Opinion in Microbiology. Jun. 1999, vol. 2, No. 3, Jun. 1999, pp. 284-228.
Ffrence-Constant R H et al: "Novel insecticidal toxins from nematode-symbiotic bacteria" CMLS Cellular and Molecular Life Sciences, vol. 57, No. 5, May 2000, pp. 828-833.
Waterfield Nicholas R et al: "Genomic islands in Photorhabdus." Trends in Microbiology, vol. 10, No. 12, Dec. 2002, pp. 541-545.

* cited by examiner

*Primary Examiner*—Anne Kubelik
(74) *Attorney, Agent, or Firm*—Donald Stuart

(57) ABSTRACT

TcdB2, a protein from *Photorhabdus luminescens* W-14, and nucleotide sequences encoding TcdB2, are useful for enhancing expression of orally active *Photorhabdus luminescens* insecticidal toxins in heterologous organisms.

14 Claims, 1 Drawing Sheet

TCDB2 PROTEIN FROM *PHOTORHABDUS LUMINESCENS* W-14

This application claims priority from United States Provisional patent Application Ser. No. U.S. 60/425,672, filed Nov. 12, 2002.

This invention provides genes from the tcd genomic region of *Photorhabdus luminescens* (W-14) that are useful in heterologous expression of orally active insect toxins.

BACKGROUND OF THE INVENTION

As reported in WO98/08932, protein toxins from the genus *Photorhabdus* have been shown to have oral toxicity against insects. The toxin complex produced by *Photorhabdus luminescens* (W-14), for example, has been shown to contain ten to fourteen proteins, and it is known that these are produced by expression of genes from four distinct genomic regions: tca, tcb, tcc, and tcd. WO98/08932 discloses nucleotide sequences for many of the native toxin genes, including the toxin gene referred to hereinafter as tcda1.

Of the separate toxins isolated from *Photorhabdus luminescens* (W-14), those designated Toxin A and Toxin B have been the subject of focused investigation for their activity against target insect species of interest, for example corn rootworm. Toxin A is comprised of two different subunits. The native gene tcdA1 (SEQ ID NO:1) encodes protoxin TcdA (see SEQ ID NO:1). As determined by mass spectrometry, TcdA1 is processed by one or more proteases to provide Toxin A. More specifically, TcdA1 is an approximately 282.9 kDA protein (2516 aa) that is processed to provide TcdAii, an approximately 208.2 kDA (1849 aa) protein encoded by nucleotides 265-5811 of SEQ ID NO:1, and TcdAiii, an approximately 63.5 kDA (579 aa) protein encoded by nucleotides 5812-7551 of SEQ ID NO:1.

WO 01/11029 discloses nucleotide sequences that encode TcdA1 and TcbA and have base compositions that have been altered from that of the native genes to make them more similar to plant genes. Also disclosed are transgenic plants that express Toxin A and Toxin B.

Heterologous expression of Toxin A does not afford the level of oral toxicity to insects that is observed for the native toxin. It would be very valuable if means could be found to enhance the level of toxicity of heterologously expressed Toxin A.

Published United States Patent Application 2002/0078478 discloses nucleotide sequences for two genes, tcdB and tccC2, from the tcd genomic region of *Photorhabdus luminescens* (W-14), and discloses that co-expression of tcdB and tccC2 with tcdA1 in heterologous hosts results in enhanced levels of oral insect toxicity compared to that obtained when tcdA1 is expressed alone in such heterologous hosts. The tcdB gene disclosed in Published U.S. patent application Ser. No. 2002/0078478 is referred to hereinafter as tcdB1.

SUMMARY OF THE INVENTION

The present invention provides nucleotide sequences for seven newly discovered genes, tccC4, tcdA3, tcdA2, tcdB2, tccC3, tcdA4, tccC5, from the tcd genomic region of *Photorhabdus luminescens* W-14. The genes can be used to express orally active insect toxins in heterologous hosts.

Three of these genes, tccC3, tccC4, tccC5, can be used in the same way that tccC2 is used, and one of them, tcdB2 can be used in the same way that tcdB1 is used, as disclosed in Published U.S. patent application Ser. No. 2002/0078478, hereby incorporated by reference, to obtain enhanced levels of oral insect activity when co-expressed with tcdA1. The tcdA3, tcdA2, and tcdA4 genes are similar to tcdA1 and are therefore expected to have similar utility as insect toxin genes.

In one embodiment of the invention tcdA1 and tcdB1 are expressed with a gene selected from tccC3, tccC4, or tccC5 in a host other than *Photorhabdus luminescens* W-14, for example in a plant.

In a second embodiment of the invention tcdA1 and tcdB2 are expressed with a gene selected from tccC2, tccC3, tccC4, or tccC5 in a host other than *Photorhabdus luminescens* W-14, for example in a plant.

SUMMARY OF THE SEQUENCES

Figure 1:
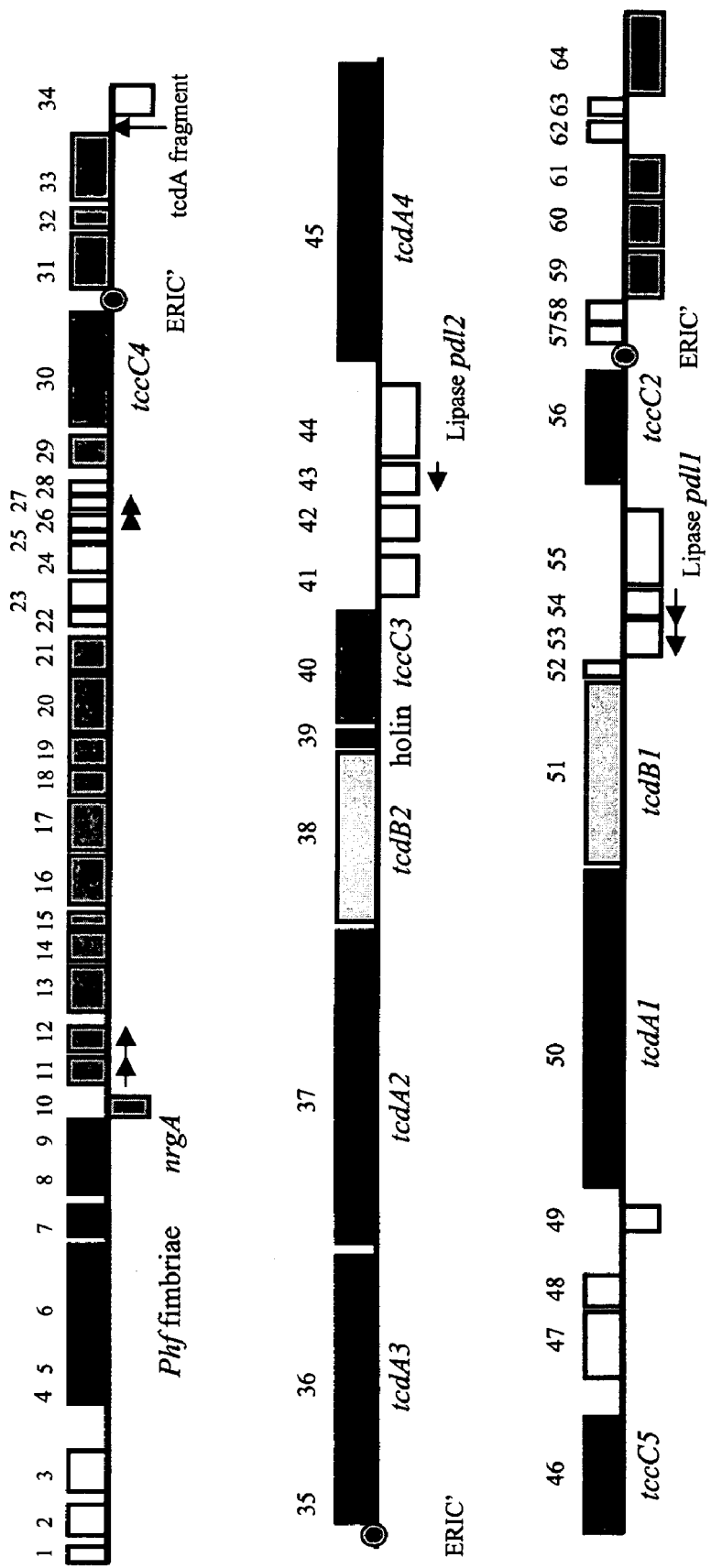
FIG. 1 illustrates a portion of the toxin complex d (tcd) island from *Photorahbdus luminescens*.

SEQ ID NO: 1 is the DNA sequence for tcdA1 from *Photorhabdus luminescens* W-14.

SEQ ID NO: 2 is the amino acid sequence for TcdA1 from *Photorhabdus luminescens* W-14.

SEQ ID NO: 3 is the DNA sequence for tcdA2 from *Photorhabdus luminescens* W-14.

SEQ ID NO: 4 is the amino acid sequence for TcdA2 from *Photorhabdus luminescens* W-14.

SEQ ID NO: 5 is the DNA sequence for tcdA3 from *Photorhabdus luminescens* W-14.

SEQ ID NO: 6 is the amino acid sequence for TcdA3 from *Photorhabdus luminescens* W-14.

SEQ ID NO: 7 is the DNA sequence for tcdA4 from *Photorhabdus luminescens* W-14.

SEQ ID NO: 8 is the amino acid sequence for TcdA4 from *Photorhabdus luminescens* W-14.

SEQ ID NO: 9 is the DNA sequence for tcdB2 from *Photorhabdus luminescens* W-14.

SEQ ID NO: 10 is the amino acid sequence for TcdB2 from *Photorhabdus luminescens* W-14.

SEQ ID NO: 11 is the DNA sequence for tccC3 from *Photorhabdus luminescens* W-14.

SEQ ID NO: 12 is the amino acid sequence for TccC3 from from *Photorhabdus luminescens* W-14.

SEQ ID NO: 13 is the DNA sequence for tccC4 from *Photorhabdus luminescens* W-14.

SEQ ID NO: 14 is the amino acid sequence for TccC4 from *Photorhabdus luminescens* W-14.

SEQ ID NO:15 is the DNA sequence for tccC5 from *Photorhabdus luminescens* W-14.

SEQ ID NO: 16 is the amino acid sequence for TccC5 from *Photorhabdus luminescens* W-14.

DETAILED DESCRIPTION OF THE INVENTION

To isolate islands unique to *Photorhabdus* we end-sequenced an arrayed cosmid library of the W-14 strain and compared the end-sequences with those in public databases using BLAST algorithms. Unique cosmids were sequenced and checked for pathogenic phenotypes, such as the ability to persist within, or kill, insects. As all *Photorhabdus* strains (even clinical isolates) are pathogenic to insects, we identified genomic islands by gene homology (BlastX), relative location in the genome (tRNA linkage or within *E. coli*-like core sequence) or altered GC content (estimated as 41.5% for the W14 core).

FIG. 1 illustrates a portion of the toxin complex d (tcd) island from *P. luminescens* W14 (accession AY144119). This unique island carries multiple copies of toxin complex (tc) genes. The tc genes encode high molecular weight insecticidal Toxin complexes or Tc's which destroy the insect midgut. The island carries multiple tcdA-like genes (ORFs 36, 37, 45 and 50) and tcdB-like genes like genes (ORFs 38 and 51). The region also carries multiple tccC-like genes (ORFs 30, 40, 46 and 56), ERIC-like (Enteric Repetitive Intergenic Consensus) sequences (see Versalovic, J. et al. (1991) Distribution of repetitive DNA sequences in eubacteria and application to fingerprinting of bacterial genomes. *Nucleic Acids Res* 19 (24), 6823-6831.), duplicated ORFs (luxR-like regulators), and a truncated tcdA-like gene.

It is preferred for the nucleic acids according to the invention to comprise at least one sequence chosen from
(a) the sequences according to SEQ ID NOS: 3, 5, 7, 9, 11, 13, and 15.
(b) at least 14 base pairs-long partial sequences of the sequences defined under (a),
(c) sequences that hybridize with the sequences defined under (a),
(d) sequences that are at least 70%, preferably 80% and even more preferred, 90% identical to the sequences defined under (a),
(e) sequences that are at least 70%, preferably 80% and even more preferred, 90% similar to the sequences defined under (a),
(f) sequences that complement the sequences defined under (a), and
(g) sequences that due to the degeneracy of the genetic code, code for the same amino acid sequence as (i.e. are "isocoding" with) the sequences defined under (a) through (e).

The expression "hybridize" as used herein refers to hybridization under the following specified conditions: 5×SSC; blocking reagent (Roche Diagnostics Inc., Mannheim, Germany), 1%; N-lauroyl-sarcosine, 0.1%; SDS (sodium-dodecyl sulfate) 0.02%; hybridization temperature: 60° C.; first wash step: 2×SSC at 60° C.; second wash step: 2×SSC at 60° C.; preferred second wash step: 0.5×SSC at 60° C.; especially preferred second wash step: 0.2×SSC at 60° C.

"Identity" and "similarity" are scored by the GAP algorithm using the Blosum 62 protein scoring matrix (Wisconsin Package Version 9.0, Genetics Computer Group (GCG), Madison, Wis.).

Expression of the Nucleotide Sequences in Heterologous Microbial Hosts

As biological insect control agents, the insecticidal toxins are produced by expression of the nucleotide sequences in heterologous host cells capable of expressing the nucleotide sequences. In a first embodiment, additional copies of one or more of the nucleotide sequences are added to *Xenorhabdus nematophilus, Xenorhabdus poinarii,* or *Photorhabdus luminescens* cells either by insertion into the chromosome or by introduction of extrachromosomally replicating molecules containing the nucleotide sequences.

In another embodiment, at least one of the nucleotide sequences of the invention is inserted into an appropriate expression cassette, comprising a promoter and termination signals. Expression of the nucleotide sequence is constitutive, or an inducible promoter responding to various types of stimuli to initiate transcription is used. In a preferred embodiment, the cell in which the toxin is expressed is a microorganism, such as a virus, a bacteria, or a fungus. In a preferred embodiment, a virus, such as a baculovirus, contains a nucleotide sequence of the invention in its genome and expresses large amounts of the corresponding insecticidal toxin after infection of appropriate eukaryotic cells that are suitable for virus replication and expression of the nucleotide sequence. The insecticidal toxin thus produced is used as an insecticidal agent. Alternatively, baculoviruses engineered to include the nucleotide sequence are used to infect insects in-vivo and kill them either by expression of the insecticidal toxin or by a combination of viral infection and expression of the insecticidal toxin.

Bacterial cells are also hosts for the expression of the nucleotide sequences of the invention. In a preferred embodiment, non-pathogenic symbiotic bacteria, which are able to live and replicate within plant tissues, so-called endophytes, or non-pathogenic symbiotic bacteria, which are capable of colonizing the phyllosphere or the rhizosphere, so-called epiphytes, are used. Such bacteria include bacteria of the genera Agrobacterium, Alcaligenes, Azospiriilum, Azotobacter, Bacillus, Ciavibacter, Enterobacter, Erwinia, Flavobacter, Klebsielia, Pseudomonas, Rhizobium, Serratia, Streptomyces and Xanthomonas. Symbiotic fungi, such as Trichoderma and Gliocladium are also possible hosts for expression of the inventive nucleotide sequences for the same purpose.

Techniques for these genetic manipulations are specific for the different available hosts and are known in the art. For example, the expression vectors pKK223-3 and pKK223-2 can be used to express heterologous genes in *E. coli*, either in transcriptional or translational fusion, behind the tac or trc promoter. For the expression of operons encoding multiple ORFS, the simplest procedure is to insert the operon into a vector such as pKK2233 in transcriptional fusion, allowing the cognate ribosome binding site of the heterologous genes to be used. Techniques for overexpression in gram-positive species such as Bacillus are also known in the art and can be used in the context of this invention (Quax et al. In.: Industrial Microorganisms: Basic and Applied Molecular Genetics, Eds. Baltz et al., American Society for Microbiology, Washington (1993)). Alternate systems for overexpression rely for example, on yeast vectors and include the use of Pichia, Saccharomyces and Kluyveromyces (Sreekrishna, In: industrial microorganisms: basic and applied molecular genetics, Baltz, Hegeman, and Skatrud eds., American Society for Microbiology, Washington (1993); Dequin & Barre, Biotechnology 12:173-177 (1994); van den Berg et al., Biotechnology 8:135-139 (1990)).

Expression of the Nucleotide Sequences in Plant Tissue

In a particularly preferred embodiment, at least one of the insecticidal toxins of the invention is expressed in a higher organism, e.g., a plant. In this case, transgenic plants expressing effective amounts of the toxins protect themselves from insect pests. When the insect starts feeding on such a transgenic plant, it also ingests the expressed toxins. This will deter the insect from further biting into the plant tissue or may even harm or kill the insect. A nucleotide sequence of the present invention is inserted into an expression cassette, which is then preferably stably integrated in the genome of said plant, In another preferred embodiment, the nucleotide sequence is included in a non-pathogenic self-replicating virus. Plants transformed in accordance with the present invention may be monocots or dicots and include, but are not limited to, maize, wheat, barley, rye, sweet potato, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, papaya, mango, banana, soybean, tomato, sorghum, sugarcane, sugarbeet, sunflower, rapeseed, clover, tobacco, carrot, cotton, alfalfa, rice, potato, eggplant, cucumber, Arabidopsis, and woody plants such as coniferous and deciduous trees.

Once a desired nucleotide sequence has been transformed into a particular plant species, it may be propagated in that species or moved into other varieties of the same species, particularly including commercial varieties, using traditional breeding techniques.

A nucleotide sequence of this invention is preferably expressed in transgenic plants, thus causing the biosynthesis of the corresponding toxin in the transgenic plants. In this way, transgenic plants with enhanced resistance to insects are generated. For their expression in transgenic plants, the nucleotide sequences of the invention may require modification and optimization. Although in many cases genes from microbial organisms can be expressed in plants at high levels without modification, low expression in transgenic plants may result from microbial nucleotide sequences having codons that are not preferred in plants. It is known in the art that all organisms have specific preferences for codon usage, and the codons of the nucleotide sequences described in this invention can be changed to conform with plant preferences, while maintaining the amino acids encoded thereby. Furthermore, high expression in plants is best achieved from coding sequences that have at least about 35% GC content, preferably more than about 45%, more preferably more than about 50%, and most preferably more than about 60%. Microbial nucleotide sequences which have low GC contents may express poorly in plants due to the existence of ATTTA motifs which may destabilize messages, and AATAAA motifs which may cause inappropriate polyadenylation. Although preferred gene sequences may be adequately expressed in both monocotyledonous and dicotyledonous plant species, sequences can be modified to account for the specific codon preferences and GC content preferences of monocotyledons or dicotyledons as these preferences have been shown to differ (Murray et al. Nucl. Acids Res. 17: 477-498 (1989)). In addition, the nucleotide sequences are screened for the existence of illegitimate splice sites that may cause message truncation. All changes required to be made within the nucleotide sequences such as those described above are made using well known techniques of site directed mutagenesis, PCR, and synthetic gene construction.

For efficient initiation of translation, sequences adjacent to the initiating methionine may require modification. For example, they can be modified by the inclusion of sequences known to be effective in plants. Joshi has suggested an appropriate consensus for plants (NAR 15: 6643-6653 (1987)) and Clontech suggests a further consensus translation initiator (1993/1994 catalog, page 210). These consensuses are suitable for use with the nucleotide sequences of this invention. The sequences are incorporated into constructions comprising the nucleotide sequences, up to and including the ATG (whilst leaving the second amino acid unmodified), or alternatively up to and including the GTC subsequent to the ATG (with the possibility of modifying the second amino acid of the transgene).

Expression of the nucleotide sequences in transgenic plants is driven by promoters shown to be functional in plants. The choice of promoter will vary depending on the temporal and spatial requirements for expression, and also depending on the target species. Thus, expression of the nucleotide sequences of this invention in leaves, in ears, in inflorescences (e.g. spikes, panicles, cobs, etc.), in roots, and/or seedlings is preferred. In many cases, however, protection against more than one type of insect pest is sought, and thus expression in multiple tissues is desirable. Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the nucleotide sequences in the desired cell.

Preferred promoters that are expressed constitutively include promoters from genes encoding actin or ubiquitin and the CAMV 35S and 19S promoters. The nucleotide sequences of this invention can also be expressed under the regulation of promoters that are chemically regulated. This enables the insecticidal toxins to be synthesized only when the crop plants are treated with the inducing chemicals.

A preferred category of promoters is that which is wound inducible. Numerous promoters have been described which are expressed at wound sites and also at the sites of phytopathogen infection. Ideally, such a promoter should only be active locally at the sites of infection, and in this way the insecticidal toxins only accumulate in cells which need to synthesize the insecticidal toxins to kill the invading insect pest. Preferred promoters of this kind include those described by Stanford et al. Mol. Gen. Genet. 215: 200-208 (1989), Xu et al. Plant Molec. Biol. 22: 573-588 (1993), Logemann et al. Plant Cell 1: 151-158 (1989), Rohrmeier & Lehle, Plant Molec. Biol. 22: 783-792 (1993), Firek et al. Plant Molec. Biol. 22: 129-142 (1993), and Warner et al. Plant J. 3: 191-201 (1993).

Especially preferred embodiments of the invention are transgenic plants expressing at least one of the nucleotide sequences of the invention in a root-preferred or root-specific fashion. Further preferred embodiments are transgenic plants expressing the nucleotide sequences in a wound-inducible or pathogen infection-inducible manner.

In addition to the selection of a suitable promoter, constructions for expression of an insecticidal toxin in plants require an appropriate transcription terminator to be attached downstream of the heterologous nucleotide sequence. Several such terminators are available and known in the art (e.g. tml from Agrobacterium, E9 from rbcs). Any available terminator known to function in plants can be used in the context of this invention.

Numerous other sequences can be incorporated into expression cassettes described in this invention. These include sequences which have been shown to enhance expression such as intron sequences (e.g. from Adhl and bronzel) and viral leader sequences (e.g. from TMV, MCMV and AMV).

It may be preferable to target expression of the nucleotide sequences of the present invention to different cellular localizations in the plant. In some cases, localization in the cytosol may be desirable, whereas in other cases, localization in some subcellular organelle may be preferred. Subcellular localization of transgene encoded enzymes is undertaken using techniques well known in the art Typically, the DNA encoding the target peptide from a known organelle-targeted gene product is manipulated and fused upstream of the nucleotide sequence. Many such target sequences are known for the chloroplast and their functioning in heterologous constructions has been shown. The expression of the nucleotide sequences of the present invention is also targeted to the endoplasmic reticulum or to the vacuoles of the host cells. Techniques to achieve this are well-known in the art.

Vectors suitable for plant transformation are described elsewhere in this specification. For Agrobacterium-mediated transformation, binary vectors or vectors carrying at least one T-DNA border sequence are suitable, whereas for direct gene transfer any vector is suitable and linear DNA containing only the construction of interest may be preferred. In the case of direct gene transfer, transformation with a single DNA species or co-transformation can be used (Schocher et al. Biotechnology 4: 1093-1096 (1986)). For both direct gene transfer and Agrobacterium-mediated transfer, transformation is usually (but not necessarily) undertaken with a selectable or screenable marker which may provide resistance to an antibiotic (kanamycin, hygromycin or methotrexate) or a herbicide (Basta). Examples of such markers are neomycin phosphotransferase, hygromycin phosphotransferase, dihydrofolate reductase, phosphinothricin acetyltransferase, 2,2-dichloroproprionic acid dehalogenase, acetohydroxyacid synthase, 5-enolpyruvyl-shikimate-phosphate synthase, haloarylnitrilase, protoporhyrinogen oxidase, acetyl-coenzyme A carboxylase, dihydropteroate synthase, chloramphenicol acetyl transferase, and β-glucuronidase. The choice of selectable or screenable marker for plant transformation is not, however, critical to the invention.

The recombinant DNA described above can be introduced into the plant cell in a number of art-recognized ways. Those skilled in the art will appreciate that the choice of method might depend on the type of plant targeted for transformation. Suitable methods of transforming plant cells include microinjection (Crossway et al., BioTechniques 4., 320-334 (1986)), electroporation (Riggs et al., Proc. Natl. Acad, Sci. USA 83., 5602-5606 (1986), Agrobacterium-mediated transformation (Hinchee et al., Biotechnology 6:915-921 (1988); See also, Ishida et al., Nature Biotechnology 14:745-750 (June 1996) (for maize transformation), direct gene transfer (Paszkowski et al., EMBO J. 3.2717-2722 (1984); Hayashimoto et al., Plant Physiol 93.857-863 (1990)(rice), and ballistic particle acceleration using devices available from Agracetus, Inc., Madison, Wis. and Dupont, Inc., Wilmington, Del. (see, for example, Sanford et al., U.S. Pat. No. 4,945,050; and McCabe et al., Biotechnology 6.923-926 (1988)). See also, Weissinger et al., Annual Rev Genet. 22-421-477 (1988); Sanford et al., Particulate Science and Technology 5.27-37 (1987)(onion); Svab et al., Proc. Natl. Acad. Sci. USA 87-8526-8530 (1990)(tobacco chloroplast); Christou et al., Plant Physiol 87,671-674 (1988)(soybean); McCabe et al., BioTechnology 6.923-926 (1988)(soybean); Klein et al., Proc. Natl. Acad. Sci. USA, 85:4305-4309 (1988)(maize); Klein et al., BioTechnology 6., 559-563 (1988) (maize); Klein et al., Plant PhysioL 91., 440-444 (1988) (maize); Fromm et al., BioTechnology 8:833-839 (1990); and Gordon-Kamm et al., Plant Cell 2: 603-618 (1990) (maize); Koziel et al., Biotechnology 11: 194-200 (1993) (maize); Shimamoto et al., Nature 338: 274-277 (1989) (rice); Christou et al., Biotechnology 9: 957-962 (1991) (rice); Datta et al., BioTechnology 8.736-740 (1990) (rice); European Patent Application EP 0 332 581 (orchardgrass and other Pooideae); Vasil et al., Biotechnology 11: 1553-1558 (1993) (wheat); Weeks et al., Plant Physiol. 102:1077-1084 (1993) (wheat); Wan et al., Plant Physiol. 104:37-48 (1994) (wheat); Jahne et al., Theor. Appl. Genet. 89:525-533 (1994)(barley); Umbeck et al., BioTechnology 5:263-266 (1987) (cotton); Casas et al., Proc. Natl. Acad. Sci. USA 90:11212-11216 (December 1993) (sorghum); Somers et al., BioTechnology 10:1589-1594 (December 1992) (oat); Torbert et al., Plant Cell Reports 14:635-640 (1995) (oat); Weeks et al., Plant Physiol. 102:1077-1084 (1993) (wheat); Chang et al., WO 94/13822 (wheat) and Nehra et al., The Plant Journal 5:285-297 (1994) (wheat). A particularly preferred set of embodiments for the introduction of recombinant DNA molecules into maize by microprojectile bombardment can be found in Koziel et al., Biotechnology 11: 194-200(1993), Hill et al., Euphytica 85:119-123 (1995) and Koziel et al., Annals of the New York Academy of Sciences 792:164-171 (1996). An additional preferred embodiment is the protoplast transformation method for maize as disclosed in EP 0 292 435. Transformation of plants can be undertaken with a single DNA species or multiple DNA species (i.e. co-transformation).

In another preferred embodiment, a nucleotide sequence of the present invention is directly transformed into the plastid genome. A major advantage of plastid transformation is that plastids are generally capable of expressing bacterial genes without substantial modification, and plastids are capable of expressing multiple open reading frames under control of a single promoter. Plastid transformation technology is extensively described in U.S. Pat. Nos. 5,451,513, 5,545,817, and 5,545,818, in PCT application no. WO 95/16783, and in McBride et al. (1994) Proc. Natl. Acad. Sci. USA 91, 7301-7305. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab, Z., Hajdukiewicz, P., and Maliga, P. (1990) Proc. Nati. Acad. Sci. USA 87, 8526-8530; Staub, J. M., and Maliga, P. (1992) Plant Cell 4, 39-45). This resulted in stable homoplasmic transformants at a frequency of approximately one per 100 bombardments of target leaves. The presence of cloning sites between these markers allowed creation of a plastid targeting vector for introduction of foreign genes (Staub, J. M., and Maliga, P. (1993) EMBO J. 12, 601-606). Substantial increases in transformation frequency are obtained by replacement of the recessive RRNA or r-protein antibiotic resistance genes with a dominant selectable marker, the bacterial aada gene encoding the spectinomycin-detoxifying enzyme aminoglycoside-3' adenyltransferase (Svab, Z., and Maliga, P. (1993) Proc. Natl. Acad. Sci. USA 90, 913-917). Previously, this marker had been used successfully for high-frequency transformation of the plastid genome of the green alga Chlamydomonas reinhardtii (Goldschmidt-Clermont, M. (1991) Nucl. Acids Res. 19: 4083-4089). Other selectable markers useful for plastid transformation are known in the art and encompassed within the scope of the invention. Typically, approximately 15-20 cell division cycles following transformation are required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein. In a preferred embodiment, a nucleotide sequence of the present invention is inserted into a plastid targeting vector and transformed into the plastid genome of a desired plant host. Plants homoplastic for plastid genomes containing a nucleotide sequence of the present invention are obtained, and are preferentially capable of high expression of the nucleotide sequence.

We claim:

1. An isolated nucleic acid that encodes SEQ ID NO:10.

2. The isolated nucleic acid of claim 1 comprising SEQ ID NO:9.

3. A transgenic monocot cell having a genome comprising a nucleic acid sequence that encodes the protein of SEQ ID NO:10.

4. A transgenic dicot cell having a genome comprising a nucleic acid sequence that encodes the protein of SEQ ID NO:10.

5. A transgenic plant with a genome comprising a nucleic acid sequence that encodes the protein of SEQ ID NO:10.

6. The transgenic plant of claim 5, wherein the plant is rice.

7. The transgenic plant of claim 5, wherein the plant is maize.

8. The transgenic plant of claim 5, wherein the plant is tobacco.

9. The transgenic plant of claim 5, wherein the plant is cotton.

10. A seed of the transgenic plant of claim 5, wherein the seed comprises the nucleic acid sequence.

11. A progeny of the seed of claim 10, wherein the progeny comprises the nucleic acid sequence.

12. In a method of producing Toxin A of *Photorhabdus luminescens* W-14 in a heterologous host the improvement comprising expressing in said host DNA that encodes the protein of SEQ ID NO: 10 and DNA that encodes a protein selected from the group consisting of—the protein of SEQ ID NO:12, the protein of SEQ ID NO:14, and the protein of SEQ ID NO:16.

13. A method of producing an orally active insect toxin said method comprising expressing in a host other than *Photorhabdus luminescens* W-14 a) a DNA sequence that encodes the protein of-SEQ ID NO:2, b) a DNA sequence that encodes the protein of SEQ ID NO:10, and c) a DNA sequence that encodes a protein selected from the group consisting of the protein of SEQ ID NO:12, the protein of SEQ ID NO:14, and the protein of SEQ ID NO:16;

wherein each of said DNA sequences is operably linked to a promoter.

14. A method of producing an orally active insect toxin which comprises expressing in a host other than *Photorhabdus luminescens* W-14 a) a DNA sequence that encodes the protein of-SEQ ID NO:2, b a DNA sequence that encodes the protein of SEQ ID NO:10, and c) a DNA sequence that encodes a protein selected from the group consisting of the protein of SEQ ID NO:12, the protein of SEQ ID NO:14, and the protein of SEQ ID NO:16;

wherein each of said DNA sequences is operably linked to a promoter.

* * * * *

SEQUENCE LISTING

<160> NUMBER OF SEQ ID NOS: 16

<210> SEQ ID NO 1
<211> LENGTH: 7551
<212> TYPE: DNA
<213> ORGANISM: Photorhabdus luminescens
<220> FEATURE:
<221> NAME/KEY: CDS
<222> LOCATION: (1)..(7548)

<400> SEQUENCE: 1

```
atg aac gag tct gta aaa gag ata cct gat gta tta aaa agc cag tgt      48
Met Asn Glu Ser Val Lys Glu Ile Pro Asp Val Leu Lys Ser Gln Cys
1               5                   10                  15 ggt ttt aat tgt ctg aca gat att agc cac agc tct ttt aat gaa ttt      96
Gly Phe Asn Cys Leu Thr Asp Ile Ser His Ser Ser Phe Asn Glu Phe
                20                  25                  30 cgc cag caa gta tct gag cac ctc tcc tgg tcc gaa aca cac gac tta     144
Arg Gln Gln Val Ser Glu His Leu Ser Trp Ser Glu Thr His Asp Leu
            35                  40                  45 tat cat gat gca caa cag gca caa aag gat aat cgc ctg tat gaa gcg     192
Tyr His Asp Ala Gln Gln Ala Gln Lys Asp Asn Arg Leu Tyr Glu Ala
        50                  55                  60 cgt att ctc aaa cgc gcc aat ccc caa tta caa aat gcg gtg cat ctt     240
Arg Ile Leu Lys Arg Ala Asn Pro Gln Leu Gln Asn Ala Val His Leu
65                  70                  75                  80 gcc att ctc gct ccc aat gct gaa ctg ata ggc tat aac aat caa ttt     288
Ala Ile Leu Ala Pro Asn Ala Glu Leu Ile Gly Tyr Asn Asn Gln Phe
                85                  90                  95 agc ggt aga gcc agt caa tat gtt gcg ccg ggt acc gtt tct tcc atg     336
Ser Gly Arg Ala Ser Gln Tyr Val Ala Pro Gly Thr Val Ser Ser Met
                100                 105                 110 ttc tcc ccc gcc gct tat ttg act gaa ctt tat cgt gaa gca cgc aat     384
Phe Ser Pro Ala Ala Tyr Leu Thr Glu Leu Tyr Arg Glu Ala Arg Asn
            115                 120                 125 tta cac gca agt gac tcc gtt tat tat ctg gat acc cgc cgc cca gat     432
Leu His Ala Ser Asp Ser Val Tyr Tyr Leu Asp Thr Arg Arg Pro Asp
        130                 135                 140 ctc aaa tca atg gcg ctc agt cag caa aat atg gat ata gaa tta tcc     480
Leu Lys Ser Met Ala Leu Ser Gln Gln Asn Met Asp Ile Glu Leu Ser
145                 150                 155                 160 aca ctc tct ttg tcc aat gag ctg tta ttg gaa agc att aaa act gaa     528
Thr Leu Ser Leu Ser Asn Glu Leu Leu Leu Glu Ser Ile Lys Thr Glu
                165                 170                 175 tct aaa ctg gaa aac tat act aaa gtg atg gaa atg ctc tcc act ttc     576
Ser Lys Leu Glu Asn Tyr Thr Lys Val Met Glu Met Leu Ser Thr Phe
            180                 185                 190 cgt cct tcc ggc gca acg cct tat cat gat gct tat gaa aat gtg cgt     624
Arg Pro Ser Gly Ala Thr Pro Tyr His Asp Ala Tyr Glu Asn Val Arg
        195                 200                 205 gaa gtt atc cag cta caa gat cct gga ctt gag caa ctc aat gca tca     672
Glu Val Ile Gln Leu Gln Asp Pro Gly Leu Glu Gln Leu Asn Ala Ser
        210                 215                 220
```

```
ccg gca att gcc ggg ttg atg cat caa gcc tcc cta ttg ggt att aac      720
Pro Ala Ile Ala Gly Leu Met His Gln Ala Ser Leu Leu Gly Ile Asn
225             230                 235                 240 gct tca atc tcg cct gag cta ttt aat att ctg acg gag gag att acc      768
Ala Ser Ile Ser Pro Glu Leu Phe Asn Ile Leu Thr Glu Glu Ile Thr
            245                 250                 255 gaa ggt aat gct gag gaa ctt tat aag aaa aat ttt ggt aat atc gaa      816
Glu Gly Asn Ala Glu Glu Leu Tyr Lys Lys Asn Phe Gly Asn Ile Glu
        260                 265                 270 ccg gcc tca ttg gct atg ccg gaa tac ctt aaa cgt tat tat aat tta      864
Pro Ala Ser Leu Ala Met Pro Glu Tyr Leu Lys Arg Tyr Tyr Asn Leu
    275                 280                 285 agc gat gaa gaa ctt agt cag ttt att ggt aaa gcc agc aat ttt ggt      912
Ser Asp Glu Glu Leu Ser Gln Phe Ile Gly Lys Ala Ser Asn Phe Gly
290                 295                 300 caa cag gaa tat agt aat aac caa ctt att act ccg gta gtc aac agc      960
Gln Gln Glu Tyr Ser Asn Asn Gln Leu Ile Thr Pro Val Val Asn Ser
305                 310                 315                 320 agt gat ggc acg gtt aag gta tat cgg atc acc cgc gaa tat aca acc     1008
Ser Asp Gly Thr Val Lys Val Tyr Arg Ile Thr Arg Glu Tyr Thr Thr
            325                 330                 335 aat gct tat caa atg gat gtg gag cta ttt ccc ttc ggt ggt gag aat     1056
Asn Ala Tyr Gln Met Asp Val Glu Leu Phe Pro Phe Gly Gly Glu Asn
        340                 345                 350 tat cgg tta gat tat aaa ttc aaa aat ttt tat aat gcc tct tat tta     1104
Tyr Arg Leu Asp Tyr Lys Phe Lys Asn Phe Tyr Asn Ala Ser Tyr Leu
    355                 360                 365 tcc atc aag tta aat gat aaa aga gaa ctt gtt cga act gaa ggc gct     1152
Ser Ile Lys Leu Asn Asp Lys Arg Glu Leu Val Arg Thr Glu Gly Ala
370                 375                 380 cct caa gtc aat ata gaa tac tcc gca aat atc aca tta aat acc gct     1200
Pro Gln Val Asn Ile Glu Tyr Ser Ala Asn Ile Thr Leu Asn Thr Ala
385                 390                 395                 400 gat atc agt caa cct ttt gaa att ggc ctg aca cga gta ctt cct tcc     1248
Asp Ile Ser Gln Pro Phe Glu Ile Gly Leu Thr Arg Val Leu Pro Ser
            405                 410                 415 ggt tct tgg gca tat gcc gcc gca aaa ttt acc gtt gaa gag tat aac     1296
Gly Ser Trp Ala Tyr Ala Ala Ala Lys Phe Thr Val Glu Glu Tyr Asn
        420                 425                 430 caa tac tct ttt ctg cta aaa ctt aac aag gct att cgt cta tca cgt     1344
Gln Tyr Ser Phe Leu Leu Lys Leu Asn Lys Ala Ile Arg Leu Ser Arg
    435                 440                 445 gcg aca gaa ttg tca ccc acg att ctg gaa ggc att gtg cgc agt gtt     1392
Ala Thr Glu Leu Ser Pro Thr Ile Leu Glu Gly Ile Val Arg Ser Val
450                 455                 460 aat cta caa ctg gat atc aac aca gac gta tta ggt aaa gtt ttt ctg     1440
Asn Leu Gln Leu Asp Ile Asn Thr Asp Val Leu Gly Lys Val Phe Leu
465                 470                 475                 480 act aaa tat tat atg cag cgt tat gct att cat gct gaa act gcc ctg     1488
Thr Lys Tyr Tyr Met Gln Arg Tyr Ala Ile His Ala Glu Thr Ala Leu
            485                 490                 495 ata cta tgc aac gcg cct att tca caa cgt tca tat gat aat caa cct     1536
Ile Leu Cys Asn Ala Pro Ile Ser Gln Arg Ser Tyr Asp Asn Gln Pro
        500                 505                 510 agc caa ttt gat cgc ctg ttt aat acg cca tta ctg aac gga caa tat     1584
Ser Gln Phe Asp Arg Leu Phe Asn Thr Pro Leu Leu Asn Gly Gln Tyr
    515                 520                 525 ttt tct acc ggc gat gag gag att gat tta aat tca ggt agc acc ggc     1632
Phe Ser Thr Gly Asp Glu Glu Ile Asp Leu Asn Ser Gly Ser Thr Gly
```

-continued

| | |
|---|---|
| gat tgg cga aaa acc ata ctt aag cgt gca ttt aat att gat gat gtc<br>Asp Trp Arg Lys Thr Ile Leu Lys Arg Ala Phe Asn Ile Asp Asp Val<br>545                        550                      555                      560 | 1680 |
| tcg ctc ttc cgc ctg ctt aaa att acc gac cat gat aat aaa gat gga<br>Ser Leu Phe Arg Leu Leu Lys Ile Thr Asp His Asp Asn Lys Asp Gly<br>565                        570                      575 | 1728 |
| aaa att aaa aat aac cta aag aat ctt tcc aat tta tat att gga aaa<br>Lys Ile Lys Asn Asn Leu Lys Asn Leu Ser Asn Leu Tyr Ile Gly Lys<br>                     580                      585                      590 | 1776 |
| tta ctg gca gat att cat caa tta acc att gat gaa ctg gat tta tta<br>Leu Leu Ala Asp Ile His Gln Leu Thr Ile Asp Glu Leu Asp Leu Leu<br>               595                      600                      605 | 1824 |
| ctg att gcc gta ggt gaa gga aaa act aat tta tcc gct atc agt gat<br>Leu Ile Ala Val Gly Glu Gly Lys Thr Asn Leu Ser Ala Ile Ser Asp<br>610                        615                      620 | 1872 |
| aag caa ttg gct acc ctg atc aga aaa ctc aat act att acc agc tgg<br>Lys Gln Leu Ala Thr Leu Ile Arg Lys Leu Asn Thr Ile Thr Ser Trp<br>625                        630                      635                      640 | 1920 |
| cta cat aca cag aag tgg agt gta ttc cag cta ttt atc atg acc tcc<br>Leu His Thr Gln Lys Trp Ser Val Phe Gln Leu Phe Ile Met Thr Ser<br>               645                      650                      655 | 1968 |
| acc agc tat aac aaa acg cta acg cct gaa att aag aat ttg ctg gat<br>Thr Ser Tyr Asn Lys Thr Leu Thr Pro Glu Ile Lys Asn Leu Leu Asp<br>660                        665                      670 | 2016 |
| acc gtc tac cac ggt tta caa ggt ttt gat aaa gac aaa gca gat ttg<br>Thr Val Tyr His Gly Leu Gln Gly Phe Asp Lys Asp Lys Ala Asp Leu<br>               675                      680                      685 | 2064 |
| cta cat gtc atg gcg ccc tat att gcg gcc acc ttg caa tta tca tcg<br>Leu His Val Met Ala Pro Tyr Ile Ala Ala Thr Leu Gln Leu Ser Ser<br>690                        695                      700 | 2112 |
| gaa aat gtc gcc cac tcg gta ctc ctt tgg gca gat aag tta cag ccc<br>Glu Asn Val Ala His Ser Val Leu Leu Trp Ala Asp Lys Leu Gln Pro<br>705                        710                      715                      720 | 2160 |
| ggc gac ggc gca atg aca gca gaa aaa ttc tgg gac tgg ttg aat act<br>Gly Asp Gly Ala Met Thr Ala Glu Lys Phe Trp Asp Trp Leu Asn Thr<br>               725                      730                      735 | 2208 |
| aag tat acg ccg ggt tca tcg gaa gcc gta gaa acg cag gaa cat atc<br>Lys Tyr Thr Pro Gly Ser Ser Glu Ala Val Glu Thr Gln Glu His Ile<br>                     740                      745                      750 | 2256 |
| gtt cag tat tgt cag gct ctg gca caa ttg gaa atg gtt tac cat tcc<br>Val Gln Tyr Cys Gln Ala Leu Ala Gln Leu Glu Met Val Tyr His Ser<br>               755                      760                      765 | 2304 |
| acc ggc atc aac gaa aac gcc ttc cgt cta ttt gtg aca aaa cca gag<br>Thr Gly Ile Asn Glu Asn Ala Phe Arg Leu Phe Val Thr Lys Pro Glu<br>770                        775                      780 | 2352 |
| atg ttt ggc gct gca act gga gca gcg ccc gcg cat gat gcc ctt tca<br>Met Phe Gly Ala Ala Thr Gly Ala Ala Pro Ala His Asp Ala Leu Ser<br>785                        790                      795                      800 | 2400 |
| ctg att atg ctg aca cgt ttt gcg gat tgg gtg aac gca cta ggc gaa<br>Leu Ile Met Leu Thr Arg Phe Ala Asp Trp Val Asn Ala Leu Gly Glu<br>               805                      810                      815 | 2448 |
| aaa gcg tcc tcg gtg cta gcg gca ttt gaa gct aac tcg tta acg gca<br>Lys Ala Ser Ser Val Leu Ala Ala Phe Glu Ala Asn Ser Leu Thr Ala<br>                     820                      825                      830 | 2496 |
| gaa caa ctg gct gat gcc atg aat ctt gat gct aat ttg ctg ttg caa<br>Glu Gln Leu Ala Asp Ala Met Asn Leu Asp Ala Asn Leu Leu Leu Gln<br>               835                      840                      845 | 2544 |
| gcc agt att caa gca caa aat cat caa cat ctt ccc cca gta act cca | 2592 |

```
                Ala Ser Ile Gln Ala Gln Asn His Gln His Leu Pro Pro Val Thr Pro
                    850                 855                 860 gaa aat gcg ttc tcc tgt tgg aca tct atc aat act atc ctg caa tgg        2640
Glu Asn Ala Phe Ser Cys Trp Thr Ser Ile Asn Thr Ile Leu Gln Trp
865                 870                 875                 880 gtt aat gtc gca caa caa ttg aat gtc gcc cca cag ggc gtt tcc gct        2688
Val Asn Val Ala Gln Gln Leu Asn Val Ala Pro Gln Gly Val Ser Ala
                885                 890                 895 ttg gtc ggg ctg gat tat att caa tca atg aaa gag aca ccg acc tat        2736
Leu Val Gly Leu Asp Tyr Ile Gln Ser Met Lys Glu Thr Pro Thr Tyr
    900                 905                 910 gcc cag tgg gaa aac gcg gca ggc gta tta acc gcc ggg ttg aat tca        2784
Ala Gln Trp Glu Asn Ala Ala Gly Val Leu Thr Ala Gly Leu Asn Ser
        915                 920                 925 caa cag gct aat aca tta cac gct ttt ctg gat gaa tct cgc agt gcc        2832
Gln Gln Ala Asn Thr Leu His Ala Phe Leu Asp Glu Ser Arg Ser Ala
            930                 935                 940 gca tta agc acc tac tat atc cgt caa gtc gcc aag gca gcg gcg gct        2880
Ala Leu Ser Thr Tyr Tyr Ile Arg Gln Val Ala Lys Ala Ala Ala Ala
945                 950                 955                 960 att aaa agc cgt gat gac ttg tat caa tac tta ctg att gat aat cag        2928
Ile Lys Ser Arg Asp Asp Leu Tyr Gln Tyr Leu Leu Ile Asp Asn Gln
                965                 970                 975 gtt tct gcg gca ata aaa acc acc cgg atc gcc gaa gcc att gcc agt        2976
Val Ser Ala Ala Ile Lys Thr Thr Arg Ile Ala Glu Ala Ile Ala Ser
                980                 985                 990 att caa ctg tac gtc aac cgg gca  ttg gaa aat gtg gaa  gaa aat gcc      3024
Ile Gln Leu Tyr Val Asn Arg Ala  Leu Glu Asn Val Glu  Glu Asn Ala
        995                 1000                1005 aat tcg ggg gtt atc agc cgc  caa ttc ttt atc gac  tgg gac aaa          3069
Asn Ser Gly Val Ile Ser Arg  Gln Phe Phe Ile Asp  Trp Asp Lys
    1010                1015                1020 tac aat aaa cgc tac agc act  tgg gcg ggt gtt tct  caa tta gtt          3114
Tyr Asn Lys Arg Tyr Ser Thr  Trp Ala Gly Val Ser  Gln Leu Val
1025                1030                1035 tac tac ccg gaa aac tat att  gat ccg acc atg cgt  atc gga caa          3159
Tyr Tyr Pro Glu Asn Tyr Ile  Asp Pro Thr Met Arg  Ile Gly Gln
    1040                1045                1050 acc aaa atg atg gac gca tta  ctg caa tcc gtc agc  caa agc caa          3204
Thr Lys Met Met Asp Ala Leu  Leu Gln Ser Val Ser  Gln Ser Gln
    1055                1060                1065 tta aac gcc gat acc gtc gaa  gat gcc ttt atg tct  tat ctg aca          3249
Leu Asn Ala Asp Thr Val Glu  Asp Ala Phe Met Ser  Tyr Leu Thr
    1070                1075                1080 tcg ttt gaa caa gtg gct aat  ctt aaa gtt att agc  gca tat cac          3294
Ser Phe Glu Gln Val Ala Asn  Leu Lys Val Ile Ser  Ala Tyr His
    1085                1090                1095 gat aat att aat aac gat caa  ggg ctg acc tat ttt  atc gga ctc          3339
Asp Asn Ile Asn Asn Asp Gln  Gly Leu Thr Tyr Phe  Ile Gly Leu
    1100                1105                1110 agt gaa act gat gcc ggt gaa  tat tat tgg cgc agt  gtc gat cac          3384
Ser Glu Thr Asp Ala Gly Glu  Tyr Tyr Trp Arg Ser  Val Asp His
    1115                1120                1125 agt aaa ttc aac gac ggt aaa  ttc gcg gct aat gcc  tgg agt gaa          3429
Ser Lys Phe Asn Asp Gly Lys  Phe Ala Ala Asn Ala  Trp Ser Glu
    1130                1135                1140 tgg cat aaa att gat tgt cca  att aac cct tat aaa  agc act atc          3474
Trp His Lys Ile Asp Cys Pro  Ile Asn Pro Tyr Lys  Ser Thr Ile
    1145                1150                1155
```

| | | | | | | | | | | | |
|---|---|---|---|---|---|---|---|---|---|---|---|
| cgt | cca | gtg | ata | tat | aaa | tcc | cgc | ctg | tat | ctg | ctc | tgg | ttg | gaa | 3519 |
| Arg | Pro | Val | Ile | Tyr | Lys | Ser | Arg | Leu | Tyr | Leu | Leu | Trp | Leu | Glu | |
| | 1160 | | | | 1165 | | | | | 1170 | | | | | |

| caa | aag | gag | atc | acc | aaa | cag | aca | gga | aat | agt | aaa | gat | ggc | tat | 3564 |
|---|---|---|---|---|---|---|---|---|---|---|---|---|---|---|---|
| Gln | Lys | Glu | Ile | Thr | Lys | Gln | Thr | Gly | Asn | Ser | Lys | Asp | Gly | Tyr | |
| | 1175 | | | | 1180 | | | | | 1185 | | | | | |

| caa | act | gaa | acg | gat | tat | cgt | tat | gaa | cta | aaa | ttg | gcg | cat | atc | 3609 |
|---|---|---|---|---|---|---|---|---|---|---|---|---|---|---|---|
| Gln | Thr | Glu | Thr | Asp | Tyr | Arg | Tyr | Glu | Leu | Lys | Leu | Ala | His | Ile | |
| 1190 | | | | | 1195 | | | | | 1200 | | | | | |

| cgc | tat | gat | ggc | act | tgg | aat | acg | cca | atc | acc | ttt | gat | gtc | aat | 3654 |
|---|---|---|---|---|---|---|---|---|---|---|---|---|---|---|---|
| Arg | Tyr | Asp | Gly | Thr | Trp | Asn | Thr | Pro | Ile | Thr | Phe | Asp | Val | Asn | |
| 1205 | | | | | 1210 | | | | | 1215 | | | | | |

| aaa | aaa | ata | tcc | gag | cta | aaa | ctg | gaa | aaa | aat | aga | gcg | ccc | gga | 3699 |
|---|---|---|---|---|---|---|---|---|---|---|---|---|---|---|---|
| Lys | Lys | Ile | Ser | Glu | Leu | Lys | Leu | Glu | Lys | Asn | Arg | Ala | Pro | Gly | |
| 1220 | | | | | 1225 | | | | | 1230 | | | | | |

| ctc | tat | tgt | gcc | ggt | tat | caa | ggt | gaa | gat | acg | ttg | ctg | gtg | atg | 3744 |
|---|---|---|---|---|---|---|---|---|---|---|---|---|---|---|---|
| Leu | Tyr | Cys | Ala | Gly | Tyr | Gln | Gly | Glu | Asp | Thr | Leu | Leu | Val | Met | |
| 1235 | | | | | 1240 | | | | | 1245 | | | | | |

| ttt | tat | aac | caa | caa | gac | aca | cta | gat | agt | tat | aaa | aac | gct | tca | 3789 |
|---|---|---|---|---|---|---|---|---|---|---|---|---|---|---|---|
| Phe | Tyr | Asn | Gln | Gln | Asp | Thr | Leu | Asp | Ser | Tyr | Lys | Asn | Ala | Ser | |
| 1250 | | | | | 1255 | | | | | 1260 | | | | | |

| atg | caa | gga | cta | tat | atc | ttt | gct | gat | atg | gca | tcc | aaa | gat | atg | 3834 |
|---|---|---|---|---|---|---|---|---|---|---|---|---|---|---|---|
| Met | Gln | Gly | Leu | Tyr | Ile | Phe | Ala | Asp | Met | Ala | Ser | Lys | Asp | Met | |
| 1265 | | | | | 1270 | | | | | 1275 | | | | | |

| acc | cca | gaa | cag | agc | aat | gtt | tat | cgg | gat | aat | agc | tat | caa | caa | 3879 |
|---|---|---|---|---|---|---|---|---|---|---|---|---|---|---|---|
| Thr | Pro | Glu | Gln | Ser | Asn | Val | Tyr | Arg | Asp | Asn | Ser | Tyr | Gln | Gln | |
| | 1280 | | | | 1285 | | | | | 1290 | | | | | |

| ttt | gat | acc | aat | aat | gtc | aga | aga | gtg | aat | aac | cgc | tat | gca | gag | 3924 |
|---|---|---|---|---|---|---|---|---|---|---|---|---|---|---|---|
| Phe | Asp | Thr | Asn | Asn | Val | Arg | Arg | Val | Asn | Asn | Arg | Tyr | Ala | Glu | |
| | 1295 | | | | 1300 | | | | | 1305 | | | | | |

| gat | tat | gag | att | cct | tcc | tcg | gta | agt | agc | cgt | aaa | gac | tat | ggt | 3969 |
|---|---|---|---|---|---|---|---|---|---|---|---|---|---|---|---|
| Asp | Tyr | Glu | Ile | Pro | Ser | Ser | Val | Ser | Ser | Arg | Lys | Asp | Tyr | Gly | |
| 1310 | | | | | 1315 | | | | | 1320 | | | | | |

| tgg | gga | gat | tat | tac | ctc | agc | atg | gta | tat | aac | gga | gat | att | cca | 4014 |
|---|---|---|---|---|---|---|---|---|---|---|---|---|---|---|---|
| Trp | Gly | Asp | Tyr | Tyr | Leu | Ser | Met | Val | Tyr | Asn | Gly | Asp | Ile | Pro | |
| 1325 | | | | | 1330 | | | | | 1335 | | | | | |

| act | atc | aat | tac | aaa | gcc | gca | tca | agt | gat | tta | aaa | atc | tat | atc | 4059 |
|---|---|---|---|---|---|---|---|---|---|---|---|---|---|---|---|
| Thr | Ile | Asn | Tyr | Lys | Ala | Ala | Ser | Ser | Asp | Leu | Lys | Ile | Tyr | Ile | |
| 1340 | | | | | 1345 | | | | | 1350 | | | | | |

| tca | cca | aaa | tta | aga | att | att | cat | aat | gga | tat | gaa | gga | cag | aag | 4104 |
|---|---|---|---|---|---|---|---|---|---|---|---|---|---|---|---|
| Ser | Pro | Lys | Leu | Arg | Ile | Ile | His | Asn | Gly | Tyr | Glu | Gly | Gln | Lys | |
| 1355 | | | | | 1360 | | | | | 1365 | | | | | |

| cgc | aat | caa | tgc | aat | ctg | atg | aat | aaa | tat | ggc | aaa | cta | ggt | gat | 4149 |
|---|---|---|---|---|---|---|---|---|---|---|---|---|---|---|---|
| Arg | Asn | Gln | Cys | Asn | Leu | Met | Asn | Lys | Tyr | Gly | Lys | Leu | Gly | Asp | |
| 1370 | | | | | 1375 | | | | | 1380 | | | | | |

| aaa | ttt | att | gtt | tat | act | agc | ttg | ggg | gtc | aat | cca | aat | aac | tcg | 4194 |
|---|---|---|---|---|---|---|---|---|---|---|---|---|---|---|---|
| Lys | Phe | Ile | Val | Tyr | Thr | Ser | Leu | Gly | Val | Asn | Pro | Asn | Asn | Ser | |
| 1385 | | | | | 1390 | | | | | 1395 | | | | | |

| tca | aat | aag | ctc | atg | ttt | tac | ccc | gtc | tat | caa | tat | agc | gga | aac | 4239 |
|---|---|---|---|---|---|---|---|---|---|---|---|---|---|---|---|
| Ser | Asn | Lys | Leu | Met | Phe | Tyr | Pro | Val | Tyr | Gln | Tyr | Ser | Gly | Asn | |
| 1400 | | | | | 1405 | | | | | 1410 | | | | | |

| acc | agt | gga | ctc | aat | caa | ggg | aga | cta | cta | ttc | cac | cgt | gac | acc | 4284 |
|---|---|---|---|---|---|---|---|---|---|---|---|---|---|---|---|
| Thr | Ser | Gly | Leu | Asn | Gln | Gly | Arg | Leu | Leu | Phe | His | Arg | Asp | Thr | |
| 1415 | | | | | 1420 | | | | | 1425 | | | | | |

| act | tat | cca | tct | aaa | gta | gaa | gct | tgg | att | cct | gga | gca | aaa | cgt | 4329 |
|---|---|---|---|---|---|---|---|---|---|---|---|---|---|---|---|
| Thr | Tyr | Pro | Ser | Lys | Val | Glu | Ala | Trp | Ile | Pro | Gly | Ala | Lys | Arg | |
| 1430 | | | | | 1435 | | | | | 1440 | | | | | |

| tct | cta | acc | aac | caa | aat | gcc | gcc | att | ggt | gat | gat | tat | gct | aca | 4374 |
|---|---|---|---|---|---|---|---|---|---|---|---|---|---|---|---|
| Ser | Leu | Thr | Asn | Gln | Asn | Ala | Ala | Ile | Gly | Asp | Asp | Tyr | Ala | Thr | |
| 1445 | | | | | 1450 | | | | | 1455 | | | | | |

```
gac tct ctg aat aaa ccg gat gat ctt aag caa tat atc ttt atg       4419
Asp Ser Leu Asn Lys Pro Asp Asp Leu Lys Gln Tyr Ile Phe Met
    1460                1465                1470 act gac agt aaa ggg act gct act gat gtc tca ggc cca gta gag       4464
Thr Asp Ser Lys Gly Thr Ala Thr Asp Val Ser Gly Pro Val Glu
    1475                1480                1485 att aat act gca att tct cca gca aaa gtt cag ata ata gtc aaa       4509
Ile Asn Thr Ala Ile Ser Pro Ala Lys Val Gln Ile Ile Val Lys
    1490                1495                1500 gcg ggt ggc aag gag caa act ttt acc gca gat aaa gat gtc tcc       4554
Ala Gly Gly Lys Glu Gln Thr Phe Thr Ala Asp Lys Asp Val Ser
    1505                1510                1515 att cag cca tca cct agc ttt gat gaa atg aat tat caa ttt aat       4599
Ile Gln Pro Ser Pro Ser Phe Asp Glu Met Asn Tyr Gln Phe Asn
    1520                1525                1530 gcc ctt gaa ata gac ggt tct ggt ctg aat ttt att aac aac tca       4644
Ala Leu Glu Ile Asp Gly Ser Gly Leu Asn Phe Ile Asn Asn Ser
    1535                1540                1545 gcc agt att gat gtt act ttt acc gca ttt gcg gag gat ggc cgc       4689
Ala Ser Ile Asp Val Thr Phe Thr Ala Phe Ala Glu Asp Gly Arg
    1550                1555                1560 aaa ctg ggt tat gaa agt ttc agt att cct gtt acc ctc aag gta       4734
Lys Leu Gly Tyr Glu Ser Phe Ser Ile Pro Val Thr Leu Lys Val
    1565                1570                1575 agt acc gat aat gcc ctg acc ctg cac cat aat gaa aat ggt gcg       4779
Ser Thr Asp Asn Ala Leu Thr Leu His His Asn Glu Asn Gly Ala
    1580                1585                1590 caa tat atg caa tgg caa tcc tat cgt acc cgc ctg aat act cta       4824
Gln Tyr Met Gln Trp Gln Ser Tyr Arg Thr Arg Leu Asn Thr Leu
    1595                1600                1605 ttt gcc cgc cag ttg gtt gca cgc gcc acc acc gga atc gat aca       4869
Phe Ala Arg Gln Leu Val Ala Arg Ala Thr Thr Gly Ile Asp Thr
    1610                1615                1620 att ctg agt atg gaa act cag aat att cag gaa ccg cag tta ggc       4914
Ile Leu Ser Met Glu Thr Gln Asn Ile Gln Glu Pro Gln Leu Gly
    1625                1630                1635 aaa ggt ttc tat gct acg ttc gtg ata cct ccc tat aac cta tca       4959
Lys Gly Phe Tyr Ala Thr Phe Val Ile Pro Pro Tyr Asn Leu Ser
    1640                1645                1650 act cat ggt gat gaa cgt tgg ttt aag ctt tat atc aaa cat gtt       5004
Thr His Gly Asp Glu Arg Trp Phe Lys Leu Tyr Ile Lys His Val
    1655                1660                1665 gtt gat aat aat tca cat att atc tat tca ggc cag cta aca gat       5049
Val Asp Asn Asn Ser His Ile Ile Tyr Ser Gly Gln Leu Thr Asp
    1670                1675                1680 aca aat ata aac atc aca tta ttt att cct ctt gat gat gtc cca       5094
Thr Asn Ile Asn Ile Thr Leu Phe Ile Pro Leu Asp Asp Val Pro
    1685                1690                1695 ttg aat caa gat tat cac gcc aag gtt tat atg acc ttc aag aaa       5139
Leu Asn Gln Asp Tyr His Ala Lys Val Tyr Met Thr Phe Lys Lys
    1700                1705                1710 tca cca tca gat ggt acc tgg tgg ggc cct cac ttt gtt aga gat       5184
Ser Pro Ser Asp Gly Thr Trp Trp Gly Pro His Phe Val Arg Asp
    1715                1720                1725 gat aaa gga ata gta aca ata aac cct aaa tcc att ttg acc cat       5229
Asp Lys Gly Ile Val Thr Ile Asn Pro Lys Ser Ile Leu Thr His
    1730                1735                1740 ttt gag agc gtc aat gtc ctg aat aat att agt agc gaa cca atg       5274
Phe Glu Ser Val Asn Val Leu Asn Asn Ile Ser Ser Glu Pro Met
```

-continued

```
              1745                1750                1755
gat ttc agc ggc gct aac agc ctc tat ttc tgg gaa ctg ttc tac      5319
Asp Phe Ser Gly Ala Asn Ser Leu Tyr Phe Trp Glu Leu Phe Tyr
        1760                1765                1770 tat acc ccg atg ctg gtt gct caa cgt ttg ctg cat gaa cag aac      5364
Tyr Thr Pro Met Leu Val Ala Gln Arg Leu Leu His Glu Gln Asn
        1775                1780                1785 ttc gat gaa gcc aac cgt tgg ctg aaa tat gtc tgg agt cca tcc      5409
Phe Asp Glu Ala Asn Arg Trp Leu Lys Tyr Val Trp Ser Pro Ser
        1790                1795                1800 ggt tat att gtc cac ggc cag att cag aac tac cag tgg aac gtc      5454
Gly Tyr Ile Val His Gly Gln Ile Gln Asn Tyr Gln Trp Asn Val
        1805                1810                1815 cgc ccg tta ctg gaa gac acc agt tgg aac agt gat cct ttg gat      5499
Arg Pro Leu Leu Glu Asp Thr Ser Trp Asn Ser Asp Pro Leu Asp
        1820                1825                1830 tcc gtc gat cct gac gcg gta gca cag cac gat cca atg cac tac      5544
Ser Val Asp Pro Asp Ala Val Ala Gln His Asp Pro Met His Tyr
        1835                1840                1845 aaa gtt tca act ttt atg cgt acc ttg gat cta ttg ata gca cgc      5589
Lys Val Ser Thr Phe Met Arg Thr Leu Asp Leu Leu Ile Ala Arg
        1850                1855                1860 ggc gac cat gct tat cgc caa ctg gaa cga gat aca ctc aac gaa      5634
Gly Asp His Ala Tyr Arg Gln Leu Glu Arg Asp Thr Leu Asn Glu
        1865                1870                1875 gcg aag atg tgg tat atg caa gcg ctg cat cta tta ggt gac aaa      5679
Ala Lys Met Trp Tyr Met Gln Ala Leu His Leu Leu Gly Asp Lys
        1880                1885                1890 cct tat cta ccg ctg agt acg aca tgg agt gat cca cga cta gac      5724
Pro Tyr Leu Pro Leu Ser Thr Thr Trp Ser Asp Pro Arg Leu Asp
        1895                1900                1905 aga gcc gcg gat atc act acc caa aat gct cac gac agc gca ata      5769
Arg Ala Ala Asp Ile Thr Thr Gln Asn Ala His Asp Ser Ala Ile
        1910                1915                1920 gtc gct ctg cgg cag aat ata cct aca ccg gca cct tta tca ttg      5814
Val Ala Leu Arg Gln Asn Ile Pro Thr Pro Ala Pro Leu Ser Leu
        1925                1930                1935 cgc agc gct aat acc ctg act gat ctc ttc ctg ccg caa atc aat      5859
Arg Ser Ala Asn Thr Leu Thr Asp Leu Phe Leu Pro Gln Ile Asn
        1940                1945                1950 gaa gtg atg atg aat tac tgg cag aca tta gct cag aga gta tac      5904
Glu Val Met Met Asn Tyr Trp Gln Thr Leu Ala Gln Arg Val Tyr
        1955                1960                1965 aat ctg cgt cat aac ctc tct atc gac ggc cag ccg tta tat ctg      5949
Asn Leu Arg His Asn Leu Ser Ile Asp Gly Gln Pro Leu Tyr Leu
        1970                1975                1980 cca atc tat gcc aca ccg gcc gat ccg aaa gcg tta ctc agc gcc      5994
Pro Ile Tyr Ala Thr Pro Ala Asp Pro Lys Ala Leu Leu Ser Ala
        1985                1990                1995 gcc gtt gcc act tct caa ggt gga ggc aag cta ccg gaa tca ttt      6039
Ala Val Ala Thr Ser Gln Gly Gly Gly Lys Leu Pro Glu Ser Phe
        2000                2005                2010 atg tcc ctg tgg cgt ttc ccg cac atg ctg gaa aat gcg cgc ggc      6084
Met Ser Leu Trp Arg Phe Pro His Met Leu Glu Asn Ala Arg Gly
        2015                2020                2025 atg gtt agc cag ctc acc cag ttc ggc tcc acg tta caa aat att      6129
Met Val Ser Gln Leu Thr Gln Phe Gly Ser Thr Leu Gln Asn Ile
        2030                2035                2040 atc gaa cgt cag gac gcg gaa gcg ctc aat gcg tta tta caa aat      6174
```

-continued

| | | | | | | | | | | | |
|---|---|---|---|---|---|---|---|---|---|---|---|
|Ile|Glu|Arg|Gln|Asp|Ala|Glu|Ala|Leu|Asn|Ala|Leu Leu Gln Asn|
|2045| | | |2050| | | |2055| | | | cag gcc gcc gag ctg ata ttg act aac ctg agc att cag gac aaa        6219
Gln Ala Ala Glu Leu Ile Leu Thr Asn Leu Ser Ile Gln Asp Lys
    2060                2065                2070 acc att gaa gaa ttg gat gcc gag aaa acg gtg ttg gaa aaa tcc        6264
Thr Ile Glu Glu Leu Asp Ala Glu Lys Thr Val Leu Glu Lys Ser
2075                2080                2085 aaa gcg gga gca caa tcg cgc ttt gat agc tac ggc aaa ctg tac        6309
Lys Ala Gly Ala Gln Ser Arg Phe Asp Ser Tyr Gly Lys Leu Tyr
    2090                2095                2100 gat gag aat atc aac gcc ggt gaa aac caa gcc atg acg cta cga        6354
Asp Glu Asn Ile Asn Ala Gly Glu Asn Gln Ala Met Thr Leu Arg
2105                2110                2115 gcg tcc gcc gcc ggg ctt acc acg gca gtt cag gca tcc cgt ctg        6399
Ala Ser Ala Ala Gly Leu Thr Thr Ala Val Gln Ala Ser Arg Leu
    2120                2125                2130 gcc ggt gcg gcg gct gat ctg gtg cct aac atc ttc ggc ttt gcc        6444
Ala Gly Ala Ala Ala Asp Leu Val Pro Asn Ile Phe Gly Phe Ala
2135                2140                2145 ggt ggc ggc agc cgt tgg ggg gct atc gct gag gcg aca ggt tat        6489
Gly Gly Gly Ser Arg Trp Gly Ala Ile Ala Glu Ala Thr Gly Tyr
    2150                2155                2160 gtg atg gaa ttc tcc gcg aat gtt atg aac acc gaa gcg gat aaa        6534
Val Met Glu Phe Ser Ala Asn Val Met Asn Thr Glu Ala Asp Lys
2165                2170                2175 att agc caa tct gaa acc tac cgt cgt cgc cgt cag gag tgg gag        6579
Ile Ser Gln Ser Glu Thr Tyr Arg Arg Arg Arg Gln Glu Trp Glu
    2180                2185                2190 atc cag cgg aat aat gcc gaa gcg gaa ttg aag caa atc gat gct        6624
Ile Gln Arg Asn Asn Ala Glu Ala Glu Leu Lys Gln Ile Asp Ala
2195                2200                2205 cag ctc aaa tca ctc gct gta cgc cgc gaa gcc gcc gta ttg cag        6669
Gln Leu Lys Ser Leu Ala Val Arg Arg Glu Ala Ala Val Leu Gln
    2210                2215                2220 aaa acc agt ctg aaa acc caa caa gaa cag acc caa tct caa ttg        6714
Lys Thr Ser Leu Lys Thr Gln Gln Glu Gln Thr Gln Ser Gln Leu
2225                2230                2235 gcc ttc ctg caa cgt aag ttc agc aat cag gcg tta tac aac tgg        6759
Ala Phe Leu Gln Arg Lys Phe Ser Asn Gln Ala Leu Tyr Asn Trp
    2240                2245                2250 ctg cgt ggt cga ctg gcg gcg att tac ttc cag ttc tac gat ttg        6804
Leu Arg Gly Arg Leu Ala Ala Ile Tyr Phe Gln Phe Tyr Asp Leu
2255                2260                2265 gcc gtc gcg cgt tgc ctg atg gca gaa caa gct tac cgt tgg gaa        6849
Ala Val Ala Arg Cys Leu Met Ala Glu Gln Ala Tyr Arg Trp Glu
    2270                2275                2280 ctc aat gat gac tct gcc cgc ttc att aaa ccg ggc gcc tgg cag        6894
Leu Asn Asp Asp Ser Ala Arg Phe Ile Lys Pro Gly Ala Trp Gln
2285                2290                2295 gga acc tat gcc ggt ctg ctt gca ggt gaa acc ttg atg ctg agt        6939
Gly Thr Tyr Ala Gly Leu Leu Ala Gly Glu Thr Leu Met Leu Ser
    2300                2305                2310 ctg gca caa atg gaa gac gct cat ctg aaa cgc gat aaa cgc gca        6984
Leu Ala Gln Met Glu Asp Ala His Leu Lys Arg Asp Lys Arg Ala
2315                2320                2325 tta gag gtt gaa cgc aca gta tcg ctg gcc gaa gtt tat gca gga        7029
Leu Glu Val Glu Arg Thr Val Ser Leu Ala Glu Val Tyr Ala Gly
2330                2335                2340

```
tta cca aaa gat aac ggt cca ttt tcc ctg gct cag gaa att gac      7074
Leu Pro Lys Asp Asn Gly Pro Phe Ser Leu Ala Gln Glu Ile Asp
    2345            2350                2355 aag ctg gtg agt caa ggt tca ggc agt gcc ggc agt ggt aat aat      7119
Lys Leu Val Ser Gln Gly Ser Gly Ser Ala Gly Ser Gly Asn Asn
    2360            2365                2370 aat ttg gcg ttc ggc gcc ggc acg gac act aaa acc tct ttg cag      7164
Asn Leu Ala Phe Gly Ala Gly Thr Asp Thr Lys Thr Ser Leu Gln
    2375            2380                2385 gca tca gtt tca ttc gct gat ttg aaa att cgt gaa gat tac ccg      7209
Ala Ser Val Ser Phe Ala Asp Leu Lys Ile Arg Glu Asp Tyr Pro
    2390            2395                2400 gca tcg ctt ggc aaa att cga cgt atc aaa cag atc agc gtc act      7254
Ala Ser Leu Gly Lys Ile Arg Arg Ile Lys Gln Ile Ser Val Thr
    2405            2410                2415 ttg ccc gcg cta ctg gga ccg tat cag gat gta cag gca ata ttg      7299
Leu Pro Ala Leu Leu Gly Pro Tyr Gln Asp Val Gln Ala Ile Leu
    2420            2425                2430 tct tac ggc gat aaa gcc gga tta gct aac ggc tgt gaa gcg ctg      7344
Ser Tyr Gly Asp Lys Ala Gly Leu Ala Asn Gly Cys Glu Ala Leu
    2435            2440                2445 gca gtt tct cac ggt atg aat gac agc ggc caa ttc cag ctc gat      7389
Ala Val Ser His Gly Met Asn Asp Ser Gly Gln Phe Gln Leu Asp
    2450            2455                2460 ttc aac gat ggc aaa ttc ctg cca ttc gaa ggc atc gcc att gat      7434
Phe Asn Asp Gly Lys Phe Leu Pro Phe Glu Gly Ile Ala Ile Asp
    2465            2470                2475 caa ggc acg ctg aca ctg agc ttc cca aat gca tct atg ccg gag      7479
Gln Gly Thr Leu Thr Leu Ser Phe Pro Asn Ala Ser Met Pro Glu
    2480            2485                2490 aaa ggt aaa caa gcc act atg tta aaa acc ctg aac gat atc att      7524
Lys Gly Lys Gln Ala Thr Met Leu Lys Thr Leu Asn Asp Ile Ile
    2495            2500                2505 ttg cat att cgc tac acc att aaa taa                              7551
Leu His Ile Arg Tyr Thr Ile Lys
    2510            2515
```

<210> SEQ ID NO 2
<211> LENGTH: 2516
<212> TYPE: PRT
<213> ORGANISM: Photorhabdus luminescens

<400> SEQUENCE: 2

```
Met Asn Glu Ser Val Lys Glu Ile Pro Asp Val Leu Lys Ser Gln Cys
1               5                   10                  15

Gly Phe Asn Cys Leu Thr Asp Ile Ser His Ser Ser Phe Asn Glu Phe
            20                  25                  30

Arg Gln Gln Val Ser Glu His Leu Ser Trp Ser Glu Thr His Asp Leu
        35                  40                  45

Tyr His Asp Ala Gln Gln Ala Gln Lys Asp Asn Arg Leu Tyr Glu Ala
    50                  55                  60

Arg Ile Leu Lys Arg Ala Asn Pro Gln Leu Gln Asn Ala Val His Leu
65                  70                  75                  80

Ala Ile Leu Ala Pro Asn Ala Glu Leu Ile Gly Tyr Asn Asn Gln Phe
                85                  90                  95

Ser Gly Arg Ala Ser Gln Tyr Val Ala Pro Gly Thr Val Ser Ser Met
            100                 105                 110

Phe Ser Pro Ala Ala Tyr Leu Thr Glu Leu Tyr Arg Glu Ala Arg Asn
        115                 120                 125
```

```
Leu His Ala Ser Asp Ser Val Tyr Tyr Leu Asp Thr Arg Arg Pro Asp
    130                 135                 140

Leu Lys Ser Met Ala Leu Ser Gln Gln Asn Met Asp Ile Glu Leu Ser
145                 150                 155                 160

Thr Leu Ser Leu Ser Asn Glu Leu Leu Leu Glu Ser Ile Lys Thr Glu
                    165                 170                 175

Ser Lys Leu Glu Asn Tyr Thr Lys Val Met Glu Met Leu Ser Thr Phe
                180                 185                 190

Arg Pro Ser Gly Ala Thr Pro Tyr His Asp Ala Tyr Glu Asn Val Arg
            195                 200                 205

Glu Val Ile Gln Leu Gln Asp Pro Gly Leu Glu Gln Leu Asn Ala Ser
        210                 215                 220

Pro Ala Ile Ala Gly Leu Met His Gln Ala Ser Leu Leu Gly Ile Asn
225                 230                 235                 240

Ala Ser Ile Ser Pro Glu Leu Phe Asn Ile Leu Thr Glu Glu Ile Thr
                    245                 250                 255

Glu Gly Asn Ala Glu Glu Leu Tyr Lys Lys Asn Phe Gly Asn Ile Glu
                260                 265                 270

Pro Ala Ser Leu Ala Met Pro Glu Tyr Leu Lys Arg Tyr Tyr Asn Leu
            275                 280                 285

Ser Asp Glu Glu Leu Ser Gln Phe Ile Gly Lys Ala Ser Asn Phe Gly
        290                 295                 300

Gln Gln Glu Tyr Ser Asn Asn Gln Leu Ile Thr Pro Val Val Asn Ser
305                 310                 315                 320

Ser Asp Gly Thr Val Lys Val Tyr Arg Ile Thr Arg Glu Tyr Thr Thr
                    325                 330                 335

Asn Ala Tyr Gln Met Asp Val Glu Leu Phe Pro Phe Gly Gly Glu Asn
                340                 345                 350

Tyr Arg Leu Asp Tyr Lys Phe Lys Asn Phe Tyr Asn Ala Ser Tyr Leu
            355                 360                 365

Ser Ile Lys Leu Asn Asp Lys Arg Glu Leu Val Arg Thr Glu Gly Ala
        370                 375                 380

Pro Gln Val Asn Ile Glu Tyr Ser Ala Asn Ile Thr Leu Asn Thr Ala
385                 390                 395                 400

Asp Ile Ser Gln Pro Phe Glu Ile Gly Leu Thr Arg Val Leu Pro Ser
                    405                 410                 415

Gly Ser Trp Ala Tyr Ala Ala Ala Lys Phe Thr Val Glu Glu Tyr Asn
                420                 425                 430

Gln Tyr Ser Phe Leu Leu Lys Leu Asn Lys Ala Ile Arg Leu Ser Arg
            435                 440                 445

Ala Thr Glu Leu Ser Pro Thr Ile Leu Glu Gly Ile Val Arg Ser Val
        450                 455                 460

Asn Leu Gln Leu Asp Ile Asn Thr Asp Val Leu Gly Lys Val Phe Leu
465                 470                 475                 480

Thr Lys Tyr Tyr Met Gln Arg Tyr Ala Ile His Ala Glu Thr Ala Leu
                    485                 490                 495

Ile Leu Cys Asn Ala Pro Ile Ser Gln Arg Ser Tyr Asp Asn Gln Pro
                500                 505                 510

Ser Gln Phe Asp Arg Leu Phe Asn Thr Pro Leu Leu Asn Gly Gln Tyr
            515                 520                 525

Phe Ser Thr Gly Asp Glu Glu Ile Asp Leu Asn Ser Gly Ser Thr Gly
        530                 535                 540
```

-continued

```
Asp Trp Arg Lys Thr Ile Leu Lys Arg Ala Phe Asn Ile Asp Asp Val
545                 550                 555                 560

Ser Leu Phe Arg Leu Leu Lys Ile Thr Asp His Asp Asn Lys Asp Gly
            565                 570                 575

Lys Ile Lys Asn Asn Leu Lys Asn Leu Ser Asn Leu Tyr Ile Gly Lys
        580                 585                 590

Leu Leu Ala Asp Ile His Gln Leu Thr Ile Asp Glu Leu Asp Leu Leu
    595                 600                 605

Leu Ile Ala Val Gly Glu Gly Lys Thr Asn Leu Ser Ala Ile Ser Asp
610                 615                 620

Lys Gln Leu Ala Thr Leu Ile Arg Lys Leu Asn Thr Ile Thr Ser Trp
625                 630                 635                 640

Leu His Thr Gln Lys Trp Ser Val Phe Gln Leu Phe Ile Met Thr Ser
            645                 650                 655

Thr Ser Tyr Asn Lys Thr Leu Thr Pro Glu Ile Lys Asn Leu Leu Asp
        660                 665                 670

Thr Val Tyr His Gly Leu Gln Gly Phe Asp Lys Asp Lys Ala Asp Leu
    675                 680                 685

Leu His Val Met Ala Pro Tyr Ile Ala Ala Thr Leu Gln Leu Ser Ser
690                 695                 700

Glu Asn Val Ala His Ser Val Leu Leu Trp Ala Asp Lys Leu Gln Pro
705                 710                 715                 720

Gly Asp Gly Ala Met Thr Ala Glu Lys Phe Trp Asp Trp Leu Asn Thr
            725                 730                 735

Lys Tyr Thr Pro Gly Ser Ser Glu Ala Val Glu Thr Gln Glu His Ile
        740                 745                 750

Val Gln Tyr Cys Gln Ala Leu Ala Gln Leu Glu Met Val Tyr His Ser
    755                 760                 765

Thr Gly Ile Asn Glu Asn Ala Phe Arg Leu Phe Val Thr Lys Pro Glu
770                 775                 780

Met Phe Gly Ala Ala Thr Gly Ala Ala Pro Ala His Asp Ala Leu Ser
785                 790                 795                 800

Leu Ile Met Leu Thr Arg Phe Ala Asp Trp Val Asn Ala Leu Gly Glu
            805                 810                 815

Lys Ala Ser Ser Val Leu Ala Ala Phe Glu Ala Asn Ser Leu Thr Ala
        820                 825                 830

Glu Gln Leu Ala Asp Ala Met Asn Leu Asp Ala Asn Leu Leu Leu Gln
    835                 840                 845

Ala Ser Ile Gln Ala Gln Asn His Gln His Leu Pro Pro Val Thr Pro
850                 855                 860

Glu Asn Ala Phe Ser Cys Trp Thr Ser Ile Asn Thr Ile Leu Gln Trp
865                 870                 875                 880

Val Asn Val Ala Gln Gln Leu Asn Val Ala Pro Gln Gly Val Ser Ala
            885                 890                 895

Leu Val Gly Leu Asp Tyr Ile Gln Ser Met Lys Glu Thr Pro Thr Tyr
        900                 905                 910

Ala Gln Trp Glu Asn Ala Ala Gly Val Leu Thr Ala Gly Leu Asn Ser
    915                 920                 925

Gln Gln Ala Asn Thr Leu His Ala Phe Leu Asp Glu Ser Arg Ser Ala
930                 935                 940

Ala Leu Ser Thr Tyr Tyr Ile Arg Gln Val Ala Lys Ala Ala Ala Ala
945                 950                 955                 960

Ile Lys Ser Arg Asp Asp Leu Tyr Gln Tyr Leu Leu Ile Asp Asn Gln
```

-continued

```
                965                 970                 975
Val Ser Ala Ala Ile Lys Thr Thr Arg Ile Ala Glu Ala Ile Ala Ser
            980                 985                 990
Ile Gln Leu Tyr Val Asn Arg Ala Leu Glu Asn Val Glu Glu Asn Ala
            995                1000                1005
Asn Ser Gly Val Ile Ser Arg Gln Phe Phe Ile Asp Trp Asp Lys
    1010                1015                1020
Tyr Asn Lys Arg Tyr Ser Thr Trp Ala Gly Val Ser Gln Leu Val
    1025                1030                1035
Tyr Tyr Pro Glu Asn Tyr Ile Asp Pro Thr Met Arg Ile Gly Gln
    1040                1045                1050
Thr Lys Met Met Asp Ala Leu Leu Gln Ser Val Ser Gln Ser Gln
    1055                1060                1065
Leu Asn Ala Asp Thr Val Glu Asp Ala Phe Met Ser Tyr Leu Thr
    1070                1075                1080
Ser Phe Glu Gln Val Ala Asn Leu Lys Val Ile Ser Ala Tyr His
    1085                1090                1095
Asp Asn Ile Asn Asn Asp Gln Gly Leu Thr Tyr Phe Ile Gly Leu
    1100                1105                1110
Ser Glu Thr Asp Ala Gly Glu Tyr Tyr Trp Arg Ser Val Asp His
    1115                1120                1125
Ser Lys Phe Asn Asp Gly Lys Phe Ala Ala Asn Ala Trp Ser Glu
    1130                1135                1140
Trp His Lys Ile Asp Cys Pro Ile Asn Pro Tyr Lys Ser Thr Ile
    1145                1150                1155
Arg Pro Val Ile Tyr Lys Ser Arg Leu Tyr Leu Leu Trp Leu Glu
    1160                1165                1170
Gln Lys Glu Ile Thr Lys Gln Thr Gly Asn Ser Lys Asp Gly Tyr
    1175                1180                1185
Gln Thr Glu Thr Asp Tyr Arg Tyr Glu Leu Lys Leu Ala His Ile
    1190                1195                1200
Arg Tyr Asp Gly Thr Trp Asn Thr Pro Ile Thr Phe Asp Val Asn
    1205                1210                1215
Lys Lys Ile Ser Glu Leu Lys Leu Glu Lys Asn Arg Ala Pro Gly
    1220                1225                1230
Leu Tyr Cys Ala Gly Tyr Gln Gly Glu Asp Thr Leu Leu Val Met
    1235                1240                1245
Phe Tyr Asn Gln Gln Asp Thr Leu Asp Ser Tyr Lys Asn Ala Ser
    1250                1255                1260
Met Gln Gly Leu Tyr Ile Phe Ala Asp Met Ala Ser Lys Asp Met
    1265                1270                1275
Thr Pro Glu Gln Ser Asn Val Tyr Arg Asp Asn Ser Tyr Gln Gln
    1280                1285                1290
Phe Asp Thr Asn Asn Val Arg Arg Val Asn Asn Arg Tyr Ala Glu
    1295                1300                1305
Asp Tyr Glu Ile Pro Ser Ser Val Ser Ser Arg Lys Asp Tyr Gly
    1310                1315                1320
Trp Gly Asp Tyr Tyr Leu Ser Met Val Tyr Asn Gly Asp Ile Pro
    1325                1330                1335
Thr Ile Asn Tyr Lys Ala Ala Ser Ser Asp Leu Lys Ile Tyr Ile
    1340                1345                1350
Ser Pro Lys Leu Arg Ile Ile His Asn Gly Tyr Glu Gly Gln Lys
    1355                1360                1365
```

-continued

```
Arg Asn Gln Cys Asn Leu Met Asn Lys Tyr Gly Lys Leu Gly Asp
    1370                1375                1380

Lys Phe Ile Val Tyr Thr Ser Leu Gly Val Asn Pro Asn Asn Ser
    1385                1390                1395

Ser Asn Lys Leu Met Phe Tyr Pro Val Tyr Gln Tyr Ser Gly Asn
    1400                1405                1410

Thr Ser Gly Leu Asn Gln Gly Arg Leu Leu Phe His Arg Asp Thr
    1415                1420                1425

Thr Tyr Pro Ser Lys Val Glu Ala Trp Ile Pro Gly Ala Lys Arg
    1430                1435                1440

Ser Leu Thr Asn Gln Asn Ala Ala Ile Gly Asp Asp Tyr Ala Thr
    1445                1450                1455

Asp Ser Leu Asn Lys Pro Asp Asp Leu Lys Gln Tyr Ile Phe Met
    1460                1465                1470

Thr Asp Ser Lys Gly Thr Ala Thr Asp Val Ser Gly Pro Val Glu
    1475                1480                1485

Ile Asn Thr Ala Ile Ser Pro Ala Lys Val Gln Ile Ile Val Lys
    1490                1495                1500

Ala Gly Gly Lys Glu Gln Thr Phe Thr Ala Asp Lys Asp Val Ser
    1505                1510                1515

Ile Gln Pro Ser Pro Ser Phe Asp Glu Met Asn Tyr Gln Phe Asn
    1520                1525                1530

Ala Leu Glu Ile Asp Gly Ser Gly Leu Asn Phe Ile Asn Asn Ser
    1535                1540                1545

Ala Ser Ile Asp Val Thr Phe Thr Ala Phe Ala Glu Asp Gly Arg
    1550                1555                1560

Lys Leu Gly Tyr Glu Ser Phe Ser Ile Pro Val Thr Leu Lys Val
    1565                1570                1575

Ser Thr Asp Asn Ala Leu Thr Leu His His Asn Glu Asn Gly Ala
    1580                1585                1590

Gln Tyr Met Gln Trp Gln Ser Tyr Arg Thr Arg Leu Asn Thr Leu
    1595                1600                1605

Phe Ala Arg Gln Leu Val Ala Arg Ala Thr Thr Gly Ile Asp Thr
    1610                1615                1620

Ile Leu Ser Met Glu Thr Gln Asn Ile Gln Glu Pro Gln Leu Gly
    1625                1630                1635

Lys Gly Phe Tyr Ala Thr Phe Val Ile Pro Pro Tyr Asn Leu Ser
    1640                1645                1650

Thr His Gly Asp Glu Arg Trp Phe Lys Leu Tyr Ile Lys His Val
    1655                1660                1665

Val Asp Asn Asn Ser His Ile Ile Tyr Ser Gly Gln Leu Thr Asp
    1670                1675                1680

Thr Asn Ile Asn Ile Thr Leu Phe Ile Pro Leu Asp Asp Val Pro
    1685                1690                1695

Leu Asn Gln Asp Tyr His Ala Lys Val Tyr Met Thr Phe Lys Lys
    1700                1705                1710

Ser Pro Ser Asp Gly Thr Trp Trp Gly Pro His Phe Val Arg Asp
    1715                1720                1725

Asp Lys Gly Ile Val Thr Ile Asn Pro Lys Ser Ile Leu Thr His
    1730                1735                1740

Phe Glu Ser Val Asn Val Leu Asn Asn Ile Ser Ser Glu Pro Met
    1745                1750                1755
```

-continued

```
Asp Phe Ser Gly Ala Asn Ser Leu Tyr Phe Trp Glu Leu Phe Tyr
    1760            1765            1770

Tyr Thr Pro Met Leu Val Ala Gln Arg Leu Leu His Glu Gln Asn
    1775            1780            1785

Phe Asp Glu Ala Asn Arg Trp Leu Lys Tyr Val Trp Ser Pro Ser
    1790            1795            1800

Gly Tyr Ile Val His Gly Gln Ile Gln Asn Tyr Gln Trp Asn Val
    1805            1810            1815

Arg Pro Leu Leu Glu Asp Thr Ser Trp Asn Ser Asp Pro Leu Asp
    1820            1825            1830

Ser Val Asp Pro Asp Ala Val Ala Gln His Asp Pro Met His Tyr
    1835            1840            1845

Lys Val Ser Thr Phe Met Arg Thr Leu Asp Leu Leu Ile Ala Arg
    1850            1855            1860

Gly Asp His Ala Tyr Arg Gln Leu Glu Arg Asp Thr Leu Asn Glu
    1865            1870            1875

Ala Lys Met Trp Tyr Met Gln Ala Leu His Leu Leu Gly Asp Lys
    1880            1885            1890

Pro Tyr Leu Pro Leu Ser Thr Thr Trp Ser Asp Pro Arg Leu Asp
    1895            1900            1905

Arg Ala Ala Asp Ile Thr Thr Gln Asn Ala His Asp Ser Ala Ile
    1910            1915            1920

Val Ala Leu Arg Gln Asn Ile Pro Thr Pro Ala Pro Leu Ser Leu
    1925            1930            1935

Arg Ser Ala Asn Thr Leu Thr Asp Leu Phe Leu Pro Gln Ile Asn
    1940            1945            1950

Glu Val Met Met Asn Tyr Trp Gln Thr Leu Ala Gln Arg Val Tyr
    1955            1960            1965

Asn Leu Arg His Asn Leu Ser Ile Asp Gly Gln Pro Leu Tyr Leu
    1970            1975            1980

Pro Ile Tyr Ala Thr Pro Ala Asp Pro Lys Ala Leu Leu Ser Ala
    1985            1990            1995

Ala Val Ala Thr Ser Gln Gly Gly Gly Lys Leu Pro Glu Ser Phe
    2000            2005            2010

Met Ser Leu Trp Arg Phe Pro His Met Leu Glu Asn Ala Arg Gly
    2015            2020            2025

Met Val Ser Gln Leu Thr Gln Phe Gly Ser Thr Leu Gln Asn Ile
    2030            2035            2040

Ile Glu Arg Gln Asp Ala Glu Ala Leu Asn Ala Leu Leu Gln Asn
    2045            2050            2055

Gln Ala Ala Glu Leu Ile Leu Thr Asn Leu Ser Ile Gln Asp Lys
    2060            2065            2070

Thr Ile Glu Glu Leu Asp Ala Glu Lys Thr Val Leu Glu Lys Ser
    2075            2080            2085

Lys Ala Gly Ala Gln Ser Arg Phe Asp Ser Tyr Gly Lys Leu Tyr
    2090            2095            2100

Asp Glu Asn Ile Asn Ala Gly Glu Asn Gln Ala Met Thr Leu Arg
    2105            2110            2115

Ala Ser Ala Ala Gly Leu Thr Thr Ala Val Gln Ala Ser Arg Leu
    2120            2125            2130

Ala Gly Ala Ala Ala Asp Leu Val Pro Asn Ile Phe Gly Phe Ala
    2135            2140            2145

Gly Gly Gly Ser Arg Trp Gly Ala Ile Ala Glu Ala Thr Gly Tyr
```

```
                    2150                2155                2160
Val Met Glu Phe Ser Ala Asn Val Met Asn Thr Glu Ala Asp Lys
    2165                2170                2175

Ile Ser Gln Ser Glu Thr Tyr Arg Arg Arg Gln Glu Trp Glu
    2180                2185                2190

Ile Gln Arg Asn Asn Ala Glu Ala Glu Leu Lys Gln Ile Asp Ala
    2195                2200                2205

Gln Leu Lys Ser Leu Ala Val Arg Arg Glu Ala Ala Val Leu Gln
    2210                2215                2220

Lys Thr Ser Leu Lys Thr Gln Gln Glu Gln Thr Gln Ser Gln Leu
    2225                2230                2235

Ala Phe Leu Gln Arg Lys Phe Ser Asn Gln Ala Leu Tyr Asn Trp
    2240                2245                2250

Leu Arg Gly Arg Leu Ala Ala Ile Tyr Phe Gln Phe Tyr Asp Leu
    2255                2260                2265

Ala Val Ala Arg Cys Leu Met Ala Glu Gln Ala Tyr Arg Trp Glu
    2270                2275                2280

Leu Asn Asp Asp Ser Ala Arg Phe Ile Lys Pro Gly Ala Trp Gln
    2285                2290                2295

Gly Thr Tyr Ala Gly Leu Leu Ala Gly Glu Thr Leu Met Leu Ser
    2300                2305                2310

Leu Ala Gln Met Glu Asp Ala His Leu Lys Arg Asp Lys Arg Ala
    2315                2320                2325

Leu Glu Val Glu Arg Thr Val Ser Leu Ala Glu Val Tyr Ala Gly
    2330                2335                2340

Leu Pro Lys Asp Asn Gly Pro Phe Ser Leu Ala Gln Glu Ile Asp
    2345                2350                2355

Lys Leu Val Ser Gln Gly Ser Gly Ser Ala Gly Ser Gly Asn Asn
    2360                2365                2370

Asn Leu Ala Phe Gly Ala Gly Thr Asp Thr Lys Thr Ser Leu Gln
    2375                2380                2385

Ala Ser Val Ser Phe Ala Asp Leu Lys Ile Arg Glu Asp Tyr Pro
    2390                2395                2400

Ala Ser Leu Gly Lys Ile Arg Arg Ile Lys Gln Ile Ser Val Thr
    2405                2410                2415

Leu Pro Ala Leu Leu Gly Pro Tyr Gln Asp Val Gln Ala Ile Leu
    2420                2425                2430

Ser Tyr Gly Asp Lys Ala Gly Leu Ala Asn Gly Cys Glu Ala Leu
    2435                2440                2445

Ala Val Ser His Gly Met Asn Asp Ser Gly Gln Phe Gln Leu Asp
    2450                2455                2460

Phe Asn Asp Gly Lys Phe Leu Pro Phe Glu Gly Ile Ala Ile Asp
    2465                2470                2475

Gln Gly Thr Leu Thr Leu Ser Phe Pro Asn Ala Ser Met Pro Glu
    2480                2485                2490

Lys Gly Lys Gln Ala Thr Met Leu Lys Thr Leu Asn Asp Ile Ile
    2495                2500                2505

Leu His Ile Arg Tyr Thr Ile Lys
    2510                2515

<210> SEQ ID NO 3
<211> LENGTH: 7500
<212> TYPE: DNA
<213> ORGANISM: Photorhabdus luminescens
```

```
<220> FEATURE:
<221> NAME/KEY: CDS
<222> LOCATION: (1)..(7500)

<400> SEQUENCE: 3 atg aac aca ctc aaa tcc gaa tat caa caa gcg tta gga gca ggt ttt        48
Met Asn Thr Leu Lys Ser Glu Tyr Gln Gln Ala Leu Gly Ala Gly Phe
1               5                   10                  15 aat aat cta acc gat atc tgc cat ctc tct ttt gac gaa ctg cgc aaa        96
Asn Asn Leu Thr Asp Ile Cys His Leu Ser Phe Asp Glu Leu Arg Lys
            20                  25                  30 aaa gtg aag gat aaa ctc tca tgg tca cag acc cag agc tta tat ctt       144
Lys Val Lys Asp Lys Leu Ser Trp Ser Gln Thr Gln Ser Leu Tyr Leu
        35                  40                  45 gaa gca cag cag gtg caa aag gat aac ctt ctg cat gaa gcc cgt att       192
Glu Ala Gln Gln Val Gln Lys Asp Asn Leu Leu His Glu Ala Arg Ile
    50                  55                  60 ctg aaa cgc gca aac cct cat tta caa agt gcg gtc cat ctt gcc ctg       240
Leu Lys Arg Ala Asn Pro His Leu Gln Ser Ala Val His Leu Ala Leu
65                  70                  75                  80 aca gca cct cat gca gac cag caa ggt tat aat agc cga ttt ggc aat       288
Thr Ala Pro His Ala Asp Gln Gln Gly Tyr Asn Ser Arg Phe Gly Asn
                85                  90                  95 cgc gcc agc aaa tat gca gcc cct ggc gca att tcc tcc atg ttt tct       336
Arg Ala Ser Lys Tyr Ala Ala Pro Gly Ala Ile Ser Ser Met Phe Ser
            100                 105                 110 ctt gcg gct tat ctg act gaa ctt tat cgt cag gca cga aat tta cat       384
Leu Ala Ala Tyr Leu Thr Glu Leu Tyr Arg Gln Ala Arg Asn Leu His
        115                 120                 125 gca gaa ggt tcc att tat cat ctg gat acg cgt cgc cca gat cta aaa       432
Ala Glu Gly Ser Ile Tyr His Leu Asp Thr Arg Arg Pro Asp Leu Lys
    130                 135                 140 tca ttg gtg ctc agc cag aaa aat atg aat acg gag att tcc acg ctt       480
Ser Leu Val Leu Ser Gln Lys Asn Met Asn Thr Glu Ile Ser Thr Leu
145                 150                 155                 160 tct ctg tct aat aac atg ttg cta aac agt att aag act cag cct aat       528
Ser Leu Ser Asn Asn Met Leu Leu Asn Ser Ile Lys Thr Gln Pro Asn
                165                 170                 175 ctg aac agc cac gct aaa gtg atg gaa aag tta tca act ttc cgc act       576
Leu Asn Ser His Ala Lys Val Met Glu Lys Leu Ser Thr Phe Arg Thr
            180                 185                 190 tct ggc tca atg cca tat cac gat gct tat gaa agt gta cgt aag att       624
Ser Gly Ser Met Pro Tyr His Asp Ala Tyr Glu Ser Val Arg Lys Ile
        195                 200                 205 att caa tta caa gct cct gtg ttt gaa caa tcc agt aca tta aca gat       672
Ile Gln Leu Gln Ala Pro Val Phe Glu Gln Ser Ser Thr Leu Thr Asp
    210                 215                 220 acg cca atc acc aaa ctg atg tat caa atc tcc ttg ctg ggg att aat       720
Thr Pro Ile Thr Lys Leu Met Tyr Gln Ile Ser Leu Leu Gly Ile Asn
225                 230                 235                 240 gcc tct gtc tca ccg gag ctg ttt act att ctg acg caa aag ata aaa       768
Ala Ser Val Ser Pro Glu Leu Phe Thr Ile Leu Thr Gln Lys Ile Lys
                245                 250                 255 cca gca acc aat gct gat aac act aat gaa cta aaa aaa ctt tat aag       816
Pro Ala Thr Asn Ala Asp Asn Thr Asn Glu Leu Lys Lys Leu Tyr Lys
            260                 265                 270 aag aat ttt ggt gaa att aaa tct att caa atg gca agg gca gaa tac       864
Lys Asn Phe Gly Glu Ile Lys Ser Ile Gln Met Ala Arg Ala Glu Tyr
        275                 280                 285 ctg aaa agt tat tat aat ctg aca gac aaa gaa ctt aac cag ttt agt       912
```

```
                                    -continued

Leu Lys Ser Tyr Tyr Asn Leu Thr Asp Lys Glu Leu Asn Gln Phe Ser
    290                 295                 300 aaa aag att aaa caa ata gat agc ctg tgg aat ata gga gac gag att        960
Lys Lys Ile Lys Gln Ile Asp Ser Leu Trp Asn Ile Gly Asp Glu Ile
305                 310                 315                 320 acc caa tac cat cta ttg aaa ttc aat aaa gct att aat cta tct cga       1008
Thr Gln Tyr His Leu Leu Lys Phe Asn Lys Ala Ile Asn Leu Ser Arg
                325                 330                 335 tca acc gag cta tca cca ata atc ctt aac agc att gcc atc gat atc       1056
Ser Thr Glu Leu Ser Pro Ile Ile Leu Asn Ser Ile Ala Ile Asp Ile
            340                 345                 350 ctt aaa aaa aca cct cca gag gat gac tct gac aac cct ttt agg gac       1104
Leu Lys Lys Thr Pro Pro Glu Asp Asp Ser Asp Asn Pro Phe Arg Asp
        355                 360                 365 gac cct gat tac ctt gaa agc ttt caa gac ctt gac ctt agt gac gaa       1152
Asp Pro Asp Tyr Leu Glu Ser Phe Gln Asp Leu Asp Leu Ser Asp Glu
    370                 375                 380 cca gat ata gac gaa gat gta tta aga gaa gct tta cgt gtt aaa gac       1200
Pro Asp Ile Asp Glu Asp Val Leu Arg Glu Ala Leu Arg Val Lys Asp
385                 390                 395                 400 tat atg caa cgt tat ggt att gat gct gag act gca tta ata ctg tgc       1248
Tyr Met Gln Arg Tyr Gly Ile Asp Ala Glu Thr Ala Leu Ile Leu Cys
                405                 410                 415 aaa gca ccc att tca gaa aat cct tct cat ccc gat cta tcc aaa tta       1296
Lys Ala Pro Ile Ser Glu Asn Pro Ser His Pro Asp Leu Ser Lys Leu
            420                 425                 430 cta gca gac atc cat caa tta act att gat gaa tta ggg gta cta ctg       1344
Leu Ala Asp Ile His Gln Leu Thr Ile Asp Glu Leu Gly Val Leu Leu
        435                 440                 445 gtt gcc ata gat gaa gga aaa acc gat tta tct cag att act cat gac       1392
Val Ala Ile Asp Glu Gly Lys Thr Asp Leu Ser Gln Ile Thr His Asp
    450                 455                 460 aat tta gcg gtt cta att agc aaa ctc tat tcc gtt acc aat tgg ctg       1440
Asn Leu Ala Val Leu Ile Ser Lys Leu Tyr Ser Val Thr Asn Trp Leu
465                 470                 475                 480 cgt aca cgg aaa tgg agt gta tat cag tta ttt gta atg acg acc gat       1488
Arg Thr Arg Lys Trp Ser Val Tyr Gln Leu Phe Val Met Thr Thr Asp
                485                 490                 495 aaa tat aac aaa acc tta acc ccg gaa ata aac aac ctt ctg gat acc       1536
Lys Tyr Asn Lys Thr Leu Thr Pro Glu Ile Asn Asn Leu Leu Asp Thr
            500                 505                 510 gtc tac aat ggc ttg cag aac ttt tac aag gat aat ttg cta aaa ata       1584
Val Tyr Asn Gly Leu Gln Asn Phe Tyr Lys Asp Asn Leu Leu Lys Ile
        515                 520                 525 aaa gat aat cta ttg aaa gcc aaa gaa agt tta cca gaa gac aaa gat       1632
Lys Asp Asn Leu Leu Lys Ala Lys Glu Ser Leu Pro Glu Asp Lys Asp
    530                 535                 540 aat ttg ccg aaa gcc gag caa tat ctg ttg gaa gcc gag aaa tat ctg       1680
Asn Leu Pro Lys Ala Glu Gln Tyr Leu Leu Glu Ala Glu Lys Tyr Leu
545                 550                 555                 560 cta gca gcc gag aaa tat ctg cta gca gcc gag aaa tat cta ttg gaa       1728
Leu Ala Ala Glu Lys Tyr Leu Leu Ala Ala Glu Lys Tyr Leu Leu Glu
                565                 570                 575 gcc aat aaa aat ccg cta gaa gcc aaa aag gct ctg aaa gaa tac gag       1776
Ala Asn Lys Asn Pro Leu Glu Ala Lys Lys Ala Leu Lys Glu Tyr Glu
            580                 585                 590 aaa aat cag gag gca tac gag aaa aat ctg aaa gaa cac gag aaa tat       1824
Lys Asn Gln Glu Ala Tyr Glu Lys Asn Leu Lys Glu His Glu Lys Tyr
        595                 600                 605
```

-continued

| | | |
|---|---|---|
| ctg ttg aaa gcc gga gaa aat ctg cca gca atc aaa gag aat ttg cta<br>Leu Leu Lys Ala Gly Glu Asn Leu Pro Ala Ile Lys Glu Asn Leu Leu<br>610                         615                    620 | 1872 |
| aaa atc aag gaa aat ctg cca aaa gcc ata tct cct tat atc gcc gcc<br>Lys Ile Lys Glu Asn Leu Pro Lys Ala Ile Ser Pro Tyr Ile Ala Ala<br>625                   630                 635               640 | 1920 |
| gct ctg caa ttg cca tct gag aat gtt gct ctc tcc gtg ctg gct tgg<br>Ala Leu Gln Leu Pro Ser Glu Asn Val Ala Leu Ser Val Leu Ala Trp<br>                         645                   650               655 | 1968 |
| gca gat aaa cta aac tct ggc aaa gaa aac aaa atg acg gca gat tca<br>Ala Asp Lys Leu Asn Ser Gly Lys Glu Asn Lys Met Thr Ala Asp Ser<br>         660                   665                 670 | 2016 |
| ttc tgg aac tgg tta cgg aaa aaa ccc att gaa act caa tcg aaa aca<br>Phe Trp Asn Trp Leu Arg Lys Lys Pro Ile Glu Thr Gln Ser Lys Thr<br>675                       680                 685 | 2064 |
| act gaa gca act gaa gca act gaa gca act gaa gca act gaa gca act<br>Thr Glu Ala Thr Glu Ala Thr Glu Ala Thr Glu Ala Thr Glu Ala Thr<br>         690                   695                 700 | 2112 |
| gaa gca act gaa aaa act aca cta att caa caa gct gtc caa tat tgc<br>Glu Ala Thr Glu Lys Thr Thr Leu Ile Gln Gln Ala Val Gln Tyr Cys<br>705                       710                 715               720 | 2160 |
| cag tgc cta gca caa ctg gcg ctg att tat cgc tct acc ggt ctt agc<br>Gln Cys Leu Ala Gln Leu Ala Leu Ile Tyr Arg Ser Thr Gly Leu Ser<br>                         725                   730               735 | 2208 |
| gaa agc act tta cgt ctg ttt gtg aca aat cca caa atc ttt ggt ctt<br>Glu Ser Thr Leu Arg Leu Phe Val Thr Asn Pro Gln Ile Phe Gly Leu<br>         740                   745                 750 | 2256 |
| acc gcg aaa aca acg tca aca cac aat gta tta tca ctg att atg ctg<br>Thr Ala Lys Thr Thr Ser Thr His Asn Val Leu Ser Leu Ile Met Leu<br>755                       760                 765 | 2304 |
| acg cgt ttt act gac tgg gtt aac tca cta ggt gaa aac gcc tct tct<br>Thr Arg Phe Thr Asp Trp Val Asn Ser Leu Gly Glu Asn Ala Ser Ser<br>         770                   775                 780 | 2352 |
| gta ctg acc gag ttt gaa aaa gga aca tta acg gca gaa cta ttg gct<br>Val Leu Thr Glu Phe Glu Lys Gly Thr Leu Thr Ala Glu Leu Leu Ala<br>785                       790                 795               800 | 2400 |
| aac gcc atg aat ctt gat aaa aat cta cta gag caa gcc agt act caa<br>Asn Ala Met Asn Leu Asp Lys Asn Leu Leu Glu Gln Ala Ser Thr Gln<br>                         805                   810               815 | 2448 |
| gca caa gct gat ttc tcc aat tgg cca tct atc gac aac cta ttg cag<br>Ala Gln Ala Asp Phe Ser Asn Trp Pro Ser Ile Asp Asn Leu Leu Gln<br>         820                   825                 830 | 2496 |
| tgg att aac atc tcg cgt caa ttg aac atc tcg cca caa ggc gtt tct<br>Trp Ile Asn Ile Ser Arg Gln Leu Asn Ile Ser Pro Gln Gly Val Ser<br>835                       840                 845 | 2544 |
| gaa ctg gcg aaa ata tta gac ata gaa tct tct act aat tat gcc caa<br>Glu Leu Ala Lys Ile Leu Asp Ile Glu Ser Ser Thr Asn Tyr Ala Gln<br>         850                   855                 860 | 2592 |
| tgg gaa aat gtc gct tca ata tta acc gcc gga cta gat acc caa aaa<br>Trp Glu Asn Val Ala Ser Ile Leu Thr Ala Gly Leu Asp Thr Gln Lys<br>865                       870                 875               880 | 2640 |
| gcc aat acc cta cat gca ttt ctg ggt gag tct cgc agt act gcg tta<br>Ala Asn Thr Leu His Ala Phe Leu Gly Glu Ser Arg Ser Thr Ala Leu<br>                         885                   890               895 | 2688 |
| agt aca tac tat att tat tct cat aac caa aaa gat cga gaa gaa aga<br>Ser Thr Tyr Tyr Ile Tyr Ser His Asn Gln Lys Asp Arg Glu Glu Arg<br>         900                   905                 910 | 2736 |
| aaa cat acg gta att aaa gac cgt gat gat cta tat caa tac ctg ttg<br>Lys His Thr Val Ile Lys Asp Arg Asp Asp Leu Tyr Gln Tyr Leu Leu<br>915                       920                 925 | 2784 |

-continued

```
atc gat aac caa gtc tcc gcc gcc atc aaa acc acg gag att gct gaa       2832
Ile Asp Asn Gln Val Ser Ala Ala Ile Lys Thr Thr Glu Ile Ala Glu
930                 935                 940 gct atc gct agt atc caa ctg tat att aac cgc gca ttg aaa aat atg       2880
Ala Ile Ala Ser Ile Gln Leu Tyr Ile Asn Arg Ala Leu Lys Asn Met
945                 950                 955                 960 gag gga gat acc gac aca agt gtc act agc cgt tta ttc ttc act aac       2928
Glu Gly Asp Thr Asp Thr Ser Val Thr Ser Arg Leu Phe Phe Thr Asn
                965                 970                 975 tgg gat aaa tac aac aaa cgc tac agc acc tgg gct ggt att act aag       2976
Trp Asp Lys Tyr Asn Lys Arg Tyr Ser Thr Trp Ala Gly Ile Thr Lys
            980                 985                 990 ctc ctt tac tac cct gaa aac tat atc gat ccg aca ctg cgg atc ggc       3024
Leu Leu Tyr Tyr Pro Glu Asn Tyr Ile Asp Pro Thr Leu Arg Ile Gly
        995                 1000                1005 cag aca aaa atg atg gat acg cta ctg caa tcc atc agc caa agt          3069
Gln Thr Lys Met Met Asp Thr Leu Leu Gln Ser Ile Ser Gln Ser
    1010                1015                1020 caa ttg aat acc gat acc gta gaa gat gcc ttt aaa tct tat cta          3114
Gln Leu Asn Thr Asp Thr Val Glu Asp Ala Phe Lys Ser Tyr Leu
    1025                1030                1035 acg tca ttc gaa caa gtg gct aat ctg gaa gtc atc agc gcc tat          3159
Thr Ser Phe Glu Gln Val Ala Asn Leu Glu Val Ile Ser Ala Tyr
    1040                1045                1050 cat gac aat att aat aat gac caa gga ttg acc tat ttt atc gga          3204
His Asp Asn Ile Asn Asn Asp Gln Gly Leu Thr Tyr Phe Ile Gly
    1055                1060                1065 cgc agt aaa aca gaa gtg aat caa tat tat tgg cgc agt gta gat          3249
Arg Ser Lys Thr Glu Val Asn Gln Tyr Tyr Trp Arg Ser Val Asp
    1070                1075                1080 cac aat aaa ttc agc gaa ggt aaa ttc ccc gct aat gcc tgg agc          3294
His Asn Lys Phe Ser Glu Gly Lys Phe Pro Ala Asn Ala Trp Ser
    1085                1090                1095 gag tgg cac aaa att gac tgc cca att aat ccc tac gaa gat act          3339
Glu Trp His Lys Ile Asp Cys Pro Ile Asn Pro Tyr Glu Asp Thr
    1100                1105                1110 atc cgc ccg gta gtc tac caa tcc cgc ctg tat att atc tgg ctg          3384
Ile Arg Pro Val Val Tyr Gln Ser Arg Leu Tyr Ile Ile Trp Leu
    1115                1120                1125 gaa cag aag aag gta act aat cga gca gaa gga gaa gct atc aaa          3429
Glu Gln Lys Lys Val Thr Asn Arg Ala Glu Gly Glu Ala Ile Lys
    1130                1135                1140 caa gga agc aaa acg acc aca agc tat cat tat gaa ctg aaa ttg          3474
Gln Gly Ser Lys Thr Thr Thr Ser Tyr His Tyr Glu Leu Lys Leu
    1145                1150                1155 gca cat att cgt tat gac ggc acc tgg aat aca cca att acc ttt          3519
Ala His Ile Arg Tyr Asp Gly Thr Trp Asn Thr Pro Ile Thr Phe
    1160                1165                1170 gat gta gat gaa aaa ata tct ggt cta aat tta gaa ctg aat aaa          3564
Asp Val Asp Glu Lys Ile Ser Gly Leu Asn Leu Glu Leu Asn Lys
    1175                1180                1185 gcg tta ggg ctc tat tgt gca agt tat caa ggc aaa gat aaa ttg          3609
Ala Leu Gly Leu Tyr Cys Ala Ser Tyr Gln Gly Lys Asp Lys Leu
    1190                1195                1200 ctg gtt atg ttt tat aaa aaa cag gag caa tta aat aat tac aca          3654
Leu Val Met Phe Tyr Lys Lys Gln Glu Gln Leu Asn Asn Tyr Thr
    1205                1210                1215 gaa aaa aca gga aac aca tac aca gca cca ata aaa ggg cta tat          3699
Glu Lys Thr Gly Asn Thr Tyr Thr Ala Pro Ile Lys Gly Leu Tyr
```

```
                     1220              1225               1230
atc act tcc aat atg tct cct gag gaa atg aca ccc gaa agt tac        3744
Ile Thr Ser Asn Met Ser Pro Glu Glu Met Thr Pro Glu Ser Tyr
    1235             1240               1245 aga ctt aat gct cat aaa cag ttt gat acc aac aat gtc gta aga        3789
Arg Leu Asn Ala His Lys Gln Phe Asp Thr Asn Asn Val Val Arg
    1250             1255               1260 gtc aat aac cgc tat gca gaa agc tac gaa atc cct tca tca gta        3834
Val Asn Asn Arg Tyr Ala Glu Ser Tyr Glu Ile Pro Ser Ser Val
    1265             1270               1275 aac agt aat aat ggt tat gat tgg gga gag ggc tat ctg agt atg        3879
Asn Ser Asn Asn Gly Tyr Asp Trp Gly Glu Gly Tyr Leu Ser Met
    1280             1285               1290 gta tac ggc ggg agc att ctg att acc cgt gac cca agc gat aac        3924
Val Tyr Gly Gly Ser Ile Leu Ile Thr Arg Asp Pro Ser Asp Asn
    1295             1300               1305 tca aaa atc caa atc tca cca aag tta aga att att cat aat gga        3969
Ser Lys Ile Gln Ile Ser Pro Lys Leu Arg Ile Ile His Asn Gly
    1310             1315               1320 tat gaa ggt cga caa cgt aat caa tgc aat ttg atg aag aaa tac        4014
Tyr Glu Gly Arg Gln Arg Asn Gln Cys Asn Leu Met Lys Lys Tyr
    1325             1330               1335 ggc aag ctc ggt gat aaa ttc att att tat act acg cta ggt att        4059
Gly Lys Leu Gly Asp Lys Phe Ile Ile Tyr Thr Thr Leu Gly Ile
    1340             1345               1350 aac ccc aat aat tta tca aat aaa aaa ctt atc tac cct gtt tat        4104
Asn Pro Asn Asn Leu Ser Asn Lys Lys Leu Ile Tyr Pro Val Tyr
    1355             1360               1365 caa tat gaa gga aat gaa agt aag ctt agt caa gga aga ctt ctg        4149
Gln Tyr Glu Gly Asn Glu Ser Lys Leu Ser Gln Gly Arg Leu Leu
    1370             1375               1380 ttt tat cgg gat agc acc act aac ttt aca aga gcc tgg ttc cct        4194
Phe Tyr Arg Asp Ser Thr Thr Asn Phe Thr Arg Ala Trp Phe Pro
    1385             1390               1395 aac ctt tct tct gac tca aaa gaa atg tcc ata acc act ggc ggt        4239
Asn Leu Ser Ser Asp Ser Lys Glu Met Ser Ile Thr Thr Gly Gly
    1400             1405               1410 aac att agt ggt aat tat ggt tat att gat aac aaa cat agt gac        4284
Asn Ile Ser Gly Asn Tyr Gly Tyr Ile Asp Asn Lys His Ser Asp
    1415             1420               1425 aac aaa cca ttc gaa gaa tat ttc tat atg gac gac cac ggc ggt        4329
Asn Lys Pro Phe Glu Glu Tyr Phe Tyr Met Asp Asp His Gly Gly
    1430             1435               1440 att gac act gac gtt tcg gag cca ata ttt att aat aca aaa att        4374
Ile Asp Thr Asp Val Ser Glu Pro Ile Phe Ile Asn Thr Lys Ile
    1445             1450               1455 cag cct tca aat gtt aaa atc ata gtg aaa aca gtg aag gat gat        4419
Gln Pro Ser Asn Val Lys Ile Ile Val Lys Thr Val Lys Asp Asp
    1460             1465               1470 gga aaa tta gac agt aaa cca tat ata gca gaa gac aaa gtt tca        4464
Gly Lys Leu Asp Ser Lys Pro Tyr Ile Ala Glu Asp Lys Val Ser
    1475             1480               1485 gtt aaa ccg aca cca aac ttt gaa gaa atg tgt tat cag ttt aat        4509
Val Lys Pro Thr Pro Asn Phe Glu Glu Met Cys Tyr Gln Phe Asn
    1490             1495               1500 aat ctc gat caa ata gat gtc tcc act cta gta ttt aaa aat aat        4554
Asn Leu Asp Gln Ile Asp Val Ser Thr Leu Val Phe Lys Asn Asn
    1505             1510               1515 gaa gca agt att gat atc acc ttt aca gca tct gct gac gca ttt        4599
```

|   |   |   |   |   |   |   |   |   |   |   |   |   |   |   |   |
|---|---|---|---|---|---|---|---|---|---|---|---|---|---|---|---|
| Glu | Ala | Ser | Ile | Asp | Ile | Thr | Phe | Thr | Ala | Ser | Ala | Asp | Ala | Phe | |
| 1520 | | | | | 1525 | | | | | 1530 | | | | | |

| gaa | agt | ggt | aaa | gaa | caa | cgt | aat | cta | ggt | gaa | gaa | cat | ttc | agt | 4644 |
|---|---|---|---|---|---|---|---|---|---|---|---|---|---|---|---|
| Glu | Ser | Gly | Lys | Glu | Gln | Arg | Asn | Leu | Gly | Glu | Glu | His | Phe | Ser | |
| 1535 | | | | | 1540 | | | | | 1545 | | | | | |

| att | cgt | att | atc | aaa | aaa | gcg | aat | gtt | aat | gat | gtc | ctg | acc | ctt | 4689 |
|---|---|---|---|---|---|---|---|---|---|---|---|---|---|---|---|
| Ile | Arg | Ile | Ile | Lys | Lys | Ala | Asn | Val | Asn | Asp | Val | Leu | Thr | Leu | |
| | 1550 | | | | | 1555 | | | | | 1560 | | | | |

| cac | cac | gat | cca | agt | ggg | gca | caa | tat | atg | caa | tgg | gga | gcc | tat | 4734 |
|---|---|---|---|---|---|---|---|---|---|---|---|---|---|---|---|
| His | His | Asp | Pro | Ser | Gly | Ala | Gln | Tyr | Met | Gln | Trp | Gly | Ala | Tyr | |
| 1565 | | | | | 1570 | | | | | 1575 | | | | | |

| cgt | act | cgc | ctt | aat | acc | ctg | ttt | gcc | cgt | aaa | tta | att | agc | cgc | 4779 |
|---|---|---|---|---|---|---|---|---|---|---|---|---|---|---|---|
| Arg | Thr | Arg | Leu | Asn | Thr | Leu | Phe | Ala | Arg | Lys | Leu | Ile | Ser | Arg | |
| 1580 | | | | | 1585 | | | | | 1590 | | | | | |

| gcc | aat | gcg | ggg | atc | gac | act | att | ttg | agt | atg | gaa | act | cag | aat | 4824 |
|---|---|---|---|---|---|---|---|---|---|---|---|---|---|---|---|
| Ala | Asn | Ala | Gly | Ile | Asp | Thr | Ile | Leu | Ser | Met | Glu | Thr | Gln | Asn | |
| 1595 | | | | | 1600 | | | | | 1605 | | | | | |

| att | caa | gag | cca | caa | tta | ggc | aaa | ggc | ttt | tat | gtt | aat | ttc | act | 4869 |
|---|---|---|---|---|---|---|---|---|---|---|---|---|---|---|---|
| Ile | Gln | Glu | Pro | Gln | Leu | Gly | Lys | Gly | Phe | Tyr | Val | Asn | Phe | Thr | |
| 1610 | | | | | 1615 | | | | | 1620 | | | | | |

| ctt | cct | aaa | tat | gat | caa | aac | aca | cat | ggt | aat | gaa | cgc | cag | ttt | 4914 |
|---|---|---|---|---|---|---|---|---|---|---|---|---|---|---|---|
| Leu | Pro | Lys | Tyr | Asp | Gln | Asn | Thr | His | Gly | Asn | Glu | Arg | Gln | Phe | |
| 1625 | | | | | 1630 | | | | | 1635 | | | | | |

| aaa | att | cat | ata | ggg | aat | att | gct | ggt | gat | aat | aca | atg | cgg | cca | 4959 |
|---|---|---|---|---|---|---|---|---|---|---|---|---|---|---|---|
| Lys | Ile | His | Ile | Gly | Asn | Ile | Ala | Gly | Asp | Asn | Thr | Met | Arg | Pro | |
| 1640 | | | | | 1645 | | | | | 1650 | | | | | |

| tat | tac | caa | gga | ata | ttg | gct | gac | acc | gaa | acc | agt | gtc | gtt | ctt | 5004 |
|---|---|---|---|---|---|---|---|---|---|---|---|---|---|---|---|
| Tyr | Tyr | Gln | Gly | Ile | Leu | Ala | Asp | Thr | Glu | Thr | Ser | Val | Val | Leu | |
| 1655 | | | | | 1660 | | | | | 1665 | | | | | |

| ttt | gtc | cct | tat | gag | aaa | caa | tct | tat | acc | aat | gaa | ggt | gtt | aga | 5049 |
|---|---|---|---|---|---|---|---|---|---|---|---|---|---|---|---|
| Phe | Val | Pro | Tyr | Glu | Lys | Gln | Ser | Tyr | Thr | Asn | Glu | Gly | Val | Arg | |
| 1670 | | | | | 1675 | | | | | 1680 | | | | | |

| tta | gga | gtt | gaa | tac | aaa | aaa | gta | tct | tac | cta | ggc | gtc | tgg | gaa | 5094 |
|---|---|---|---|---|---|---|---|---|---|---|---|---|---|---|---|
| Leu | Gly | Val | Glu | Tyr | Lys | Lys | Val | Ser | Tyr | Leu | Gly | Val | Trp | Glu | |
| 1685 | | | | | 1690 | | | | | 1695 | | | | | |

| ccc | gct | ttc | ttc | tat | ttc | aat | gaa | att | caa | cag | aag | ttt | att | ctg | 5139 |
|---|---|---|---|---|---|---|---|---|---|---|---|---|---|---|---|
| Pro | Ala | Phe | Phe | Tyr | Phe | Asn | Glu | Ile | Gln | Gln | Lys | Phe | Ile | Leu | |
| 1700 | | | | | 1705 | | | | | 1710 | | | | | |

| att | aat | gat | gcc | gat | cat | aac | tca | gca | atg | act | caa | tct | ggt | gaa | 5184 |
|---|---|---|---|---|---|---|---|---|---|---|---|---|---|---|---|
| Ile | Asn | Asp | Ala | Asp | His | Asn | Ser | Ala | Met | Thr | Gln | Ser | Gly | Glu | |
| 1715 | | | | | 1720 | | | | | 1725 | | | | | |

| aaa | aca | gga | att | aaa | aaa | tac | aaa | ggc | ttt | ctt | gac | gtt | tct | att | 5229 |
|---|---|---|---|---|---|---|---|---|---|---|---|---|---|---|---|
| Lys | Thr | Gly | Ile | Lys | Lys | Tyr | Lys | Gly | Phe | Leu | Asp | Val | Ser | Ile | |
| 1730 | | | | | 1735 | | | | | 1740 | | | | | |

| ctt | atc | gat | cat | cag | cac | aca | gaa | cca | atg | gac | ttc | aac | ggc | gcc | 5274 |
|---|---|---|---|---|---|---|---|---|---|---|---|---|---|---|---|
| Leu | Ile | Asp | His | Gln | His | Thr | Glu | Pro | Met | Asp | Phe | Asn | Gly | Ala | |
| 1745 | | | | | 1750 | | | | | 1755 | | | | | |

| aac | agc | ctc | tac | ttc | tgg | gaa | ctg | ttc | tac | tat | acc | ccg | atg | ctg | 5319 |
|---|---|---|---|---|---|---|---|---|---|---|---|---|---|---|---|
| Asn | Ser | Leu | Tyr | Phe | Trp | Glu | Leu | Phe | Tyr | Tyr | Thr | Pro | Met | Leu | |
| 1760 | | | | | 1765 | | | | | 1770 | | | | | |

| atc | gct | caa | cgt | ttg | cta | cac | gag | caa | aat | ttc | gat | gaa | gct | aac | 5364 |
|---|---|---|---|---|---|---|---|---|---|---|---|---|---|---|---|
| Ile | Ala | Gln | Arg | Leu | Leu | His | Glu | Gln | Asn | Phe | Asp | Glu | Ala | Asn | |
| 1775 | | | | | 1780 | | | | | 1785 | | | | | |

| cgt | tgg | ctg | aaa | tat | gtc | tgg | aat | cca | tct | ggt | cat | att | gcc | aat | 5409 |
|---|---|---|---|---|---|---|---|---|---|---|---|---|---|---|---|
| Arg | Trp | Leu | Lys | Tyr | Val | Trp | Asn | Pro | Ser | Gly | His | Ile | Ala | Asn | |
| 1790 | | | | | 1795 | | | | | 1800 | | | | | |

| ggt | caa | aaa | cag | cac | ccc | cac | aac | tgg | aat | gtc | cgc | cca | tta | caa | 5454 |
|---|---|---|---|---|---|---|---|---|---|---|---|---|---|---|---|
| Gly | Gln | Lys | Gln | His | Pro | His | Asn | Trp | Asn | Val | Arg | Pro | Leu | Gln | |
| 1805 | | | | | 1810 | | | | | 1815 | | | | | |

-continued

| | | | | | | | | | | | | | | |
|---|---|---|---|---|---|---|---|---|---|---|---|---|---|---|
| gag | gac | acc | agt | tgg | aac | gat | gat | cca | ttg | gat | aca | ttt | gat | ccc | 5499 |
| Glu | Asp | Thr | Ser | Trp | Asn | Asp | Asp | Pro | Leu | Asp | Thr | Phe | Asp | Pro | |
| | 1820 | | | | 1825 | | | | | 1830 | | | | | |
| gat | gcc | atc | gct | caa | cat | gat | ccg | atg | cac | tac | aaa | gtc | gcc | acc | 5544 |
| Asp | Ala | Ile | Ala | Gln | His | Asp | Pro | Met | His | Tyr | Lys | Val | Ala | Thr | |
| 1835 | | | | | 1840 | | | | | 1845 | | | | | |
| ttt | atg | tgc | gcc | ctt | gat | cta | ttg | atc | gaa | cag | gga | gat | tac | gcc | 5589 |
| Phe | Met | Cys | Ala | Leu | Asp | Leu | Leu | Ile | Glu | Gln | Gly | Asp | Tyr | Ala | |
| 1850 | | | | | 1855 | | | | | 1860 | | | | | |
| tat | cgc | cag | ttg | gaa | cgg | gac | aca | ctc | gcc | gaa | gcc | aaa | atg | tgg | 5634 |
| Tyr | Arg | Gln | Leu | Glu | Arg | Asp | Thr | Leu | Ala | Glu | Ala | Lys | Met | Trp | |
| 1865 | | | | | 1870 | | | | | 1875 | | | | | |
| tat | atg | cag | gca | ctg | cat | cta | tta | ggc | gat | aaa | cct | cat | tta | tta | 5679 |
| Tyr | Met | Gln | Ala | Leu | His | Leu | Leu | Gly | Asp | Lys | Pro | His | Leu | Leu | |
| 1880 | | | | | 1885 | | | | | 1890 | | | | | |
| ctc | agt | tca | aca | tgg | agt | gat | cca | gag | cta | aaa | gaa | gcc | gca | gat | 5724 |
| Leu | Ser | Ser | Thr | Trp | Ser | Asp | Pro | Glu | Leu | Lys | Glu | Ala | Ala | Asp | |
| 1895 | | | | | 1900 | | | | | 1905 | | | | | |
| ctt | gaa | aaa | caa | cag | gca | cat | gcc | aaa | gca | ata | gca | gat | tta | cga | 5769 |
| Leu | Glu | Lys | Gln | Gln | Ala | His | Ala | Lys | Ala | Ile | Ala | Asp | Leu | Arg | |
| 1910 | | | | | 1915 | | | | | 1920 | | | | | |
| caa | ggc | cag | cct | aaa | gat | gga | agc | aac | aca | gat | ctt | ttc | ctg | cca | 5814 |
| Gln | Gly | Gln | Pro | Lys | Asp | Gly | Ser | Asn | Thr | Asp | Leu | Phe | Leu | Pro | |
| 1925 | | | | | 1930 | | | | | 1935 | | | | | |
| cag | gtc | aac | gaa | gtg | atg | ttg | agc | tat | tgg | cag | aaa | ctg | gaa | caa | 5859 |
| Gln | Val | Asn | Glu | Val | Met | Leu | Ser | Tyr | Trp | Gln | Lys | Leu | Glu | Gln | |
| 1940 | | | | | 1945 | | | | | 1950 | | | | | |
| cgg | tta | tat | aac | ctg | cgc | cat | aac | ctc | tct | att | gat | ggt | caa | cct | 5904 |
| Arg | Leu | Tyr | Asn | Leu | Arg | His | Asn | Leu | Ser | Ile | Asp | Gly | Gln | Pro | |
| 1955 | | | | | 1960 | | | | | 1965 | | | | | |
| tta | cat | ttg | cct | att | ttc | gcg | aca | ccg | gca | gat | cca | aaa | gcg | ctg | 5949 |
| Leu | His | Leu | Pro | Ile | Phe | Ala | Thr | Pro | Ala | Asp | Pro | Lys | Ala | Leu | |
| 1970 | | | | | 1975 | | | | | 1980 | | | | | |
| ctc | agc | gcc | gct | gtc | gcc | agt | tca | caa | ggt | gga | agc | aat | ctt | ccg | 5994 |
| Leu | Ser | Ala | Ala | Val | Ala | Ser | Ser | Gln | Gly | Gly | Ser | Asn | Leu | Pro | |
| 1985 | | | | | 1990 | | | | | 1995 | | | | | |
| tca | gag | ttt | ata | tca | gtt | tgg | cgt | ttc | cca | cat | atg | ctg | gaa | aac | 6039 |
| Ser | Glu | Phe | Ile | Ser | Val | Trp | Arg | Phe | Pro | His | Met | Leu | Glu | Asn | |
| | 2000 | | | | 2005 | | | | | 2010 | | | | | |
| gcc | cgc | agt | atg | gtc | agt | caa | ctc | acc | caa | ttc | ggc | tcc | aca | tta | 6084 |
| Ala | Arg | Ser | Met | Val | Ser | Gln | Leu | Thr | Gln | Phe | Gly | Ser | Thr | Leu | |
| | 2015 | | | | 2020 | | | | | 2025 | | | | | |
| caa | aat | att | atc | gaa | cgt | cag | gat | gcg | gaa | gca | tta | aac | acg | ctg | 6129 |
| Gln | Asn | Ile | Ile | Glu | Arg | Gln | Asp | Ala | Glu | Ala | Leu | Asn | Thr | Leu | |
| | 2030 | | | | 2035 | | | | | 2040 | | | | | |
| tta | cag | aat | caa | gcg | gcg | gaa | ctg | ata | ttg | acc | aat | ctc | agc | ata | 6174 |
| Leu | Gln | Asn | Gln | Ala | Ala | Glu | Leu | Ile | Leu | Thr | Asn | Leu | Ser | Ile | |
| | 2045 | | | | 2050 | | | | | 2055 | | | | | |
| cag | gac | aaa | acc | att | gaa | gag | ctg | gat | gtt | gaa | aaa | act | gtg | cta | 6219 |
| Gln | Asp | Lys | Thr | Ile | Glu | Glu | Leu | Asp | Val | Glu | Lys | Thr | Val | Leu | |
| | 2060 | | | | 2065 | | | | | 2070 | | | | | |
| gaa | aaa | acc | cgc | gcc | gga | gct | aaa | tcg | cgt | ttt | gat | agc | tac | agc | 6264 |
| Glu | Lys | Thr | Arg | Ala | Gly | Ala | Lys | Ser | Arg | Phe | Asp | Ser | Tyr | Ser | |
| | 2075 | | | | 2080 | | | | | 2085 | | | | | |
| aaa | ttc | tac | gat | gaa | gat | atc | aac | gca | ggt | gaa | aaa | cag | gcg | atg | 6309 |
| Lys | Phe | Tyr | Asp | Glu | Asp | Ile | Asn | Ala | Gly | Glu | Lys | Gln | Ala | Met | |
| | 2090 | | | | 2095 | | | | | 2100 | | | | | |
| gcg | ttg | cga | gcc | tcc | gtc | gca | ggc | atc | tct | act | gca | ctt | caa | gca | 6354 |
| Ala | Leu | Arg | Ala | Ser | Val | Ala | Gly | Ile | Ser | Thr | Ala | Leu | Gln | Ala | |
| | 2105 | | | | 2110 | | | | | 2115 | | | | | |

-continued

| | | |
|---|---|---|
| tca cat ctg gca ggc gca gcg ctt gat ttg gct ccc aac atc ttt<br>Ser His Leu Ala Gly Ala Ala Leu Asp Leu Ala Pro Asn Ile Phe<br>     2120                 2125                 2130 | | 6399 |
| ggc ttc gct gat ggc ggt agc cat tgg gga gca att gcc caa gcc<br>Gly Phe Ala Asp Gly Gly Ser His Trp Gly Ala Ile Ala Gln Ala<br>     2135                 2140                 2145 | | 6444 |
| aca agt aat gtc atg gaa ttc tcc gcc agt gtc atg agc acc gaa<br>Thr Ser Asn Val Met Glu Phe Ser Ala Ser Val Met Ser Thr Glu<br>     2150                 2155                 2160 | | 6489 |
| gcg gat aaa atc agc cag tct gaa gcc tac cgt cgg cgt cga cag<br>Ala Asp Lys Ile Ser Gln Ser Glu Ala Tyr Arg Arg Arg Arg Gln<br>     2165                 2170                 2175 | | 6534 |
| gag tgg aaa atc cag cgt aac aac gct gat gca gag ttg aaa caa<br>Glu Trp Lys Ile Gln Arg Asn Asn Ala Asp Ala Glu Leu Lys Gln<br>     2180                 2185                 2190 | | 6579 |
| atc gat gct caa ctt caa tca tta gtc gta cgc cgt gaa gcc gcc<br>Ile Asp Ala Gln Leu Gln Ser Leu Val Val Arg Arg Glu Ala Ala<br>     2195                 2200                 2205 | | 6624 |
| gtg ttg cag aaa acc agc ctg aaa acc caa caa gag cag acg cac<br>Val Leu Gln Lys Thr Ser Leu Lys Thr Gln Gln Glu Gln Thr His<br>     2210                 2215                 2220 | | 6669 |
| gca caa ctg acc ttc ctg caa cat aag ttc agc aat cag gca tta<br>Ala Gln Leu Thr Phe Leu Gln His Lys Phe Ser Asn Gln Ala Leu<br>     2225                 2230                 2235 | | 6714 |
| tac aac tgg ctg cgt ggt cgg ctg tcc gcc att tac ttc cag ttc<br>Tyr Asn Trp Leu Arg Gly Arg Leu Ser Ala Ile Tyr Phe Gln Phe<br>     2240                 2245                 2250 | | 6759 |
| tat gat tta gcg gta gcc cgt tgc ctg atg gct gaa atg gcc tat<br>Tyr Asp Leu Ala Val Ala Arg Cys Leu Met Ala Glu Met Ala Tyr<br>     2255                 2260                 2265 | | 6804 |
| cgt tgg gag act aac gat gcc gca gca cgc ttt atc aag ccc ggc<br>Arg Trp Glu Thr Asn Asp Ala Ala Ala Arg Phe Ile Lys Pro Gly<br>     2270                 2275                 2280 | | 6849 |
| gcc tgg cag gga acc cat gcc ggt ctg ctg gcg ggt gaa acc tta<br>Ala Trp Gln Gly Thr His Ala Gly Leu Leu Ala Gly Glu Thr Leu<br>     2285                 2290                 2295 | | 6894 |
| atg ctg aat cta gca cag atg gaa gat gcc cac ctg aaa cag gag<br>Met Leu Asn Leu Ala Gln Met Glu Asp Ala His Leu Lys Gln Glu<br>     2300                 2305                 2310 | | 6939 |
| caa cgc gta ctg gag gta gaa cgt acc gtt tca cta gca gaa gtt<br>Gln Arg Val Leu Glu Val Glu Arg Thr Val Ser Leu Ala Glu Val<br>     2315                 2320                 2325 | | 6984 |
| tat aaa gag aaa ggt caa ttt tct ctg acc aag aaa att gca gaa<br>Tyr Lys Glu Lys Gly Gln Phe Ser Leu Thr Lys Lys Ile Ala Glu<br>     2330                 2335                 2340 | | 7029 |
| ctg gtg aat aag aaa cca gac act acc agt agc aga aat aac aca<br>Leu Val Asn Lys Lys Pro Asp Thr Thr Ser Ser Arg Asn Asn Thr<br>     2345                 2350                 2355 | | 7074 |
| ctg aat ttt ggt gaa gga aat gcc aaa act tct cta caa gcg tct<br>Leu Asn Phe Gly Glu Gly Asn Ala Lys Thr Ser Leu Gln Ala Ser<br>     2360                 2365                 2370 | | 7119 |
| att tcg tta gct gac tta caa att cgt cac gat tac cca gaa aac<br>Ile Ser Leu Ala Asp Leu Gln Ile Arg His Asp Tyr Pro Glu Asn<br>     2375                 2380                 2385 | | 7164 |
| agt gga gcc ggt aac gtc cgc cgg att aaa cag atc agt gtc acc<br>Ser Gly Ala Gly Asn Val Arg Arg Ile Lys Gln Ile Ser Val Thr<br>     2390                 2395                 2400 | | 7209 |
| ctg ccg gca ctg tta gga cct tat cag gat gtg caa gcg att ctg<br>Leu Pro Ala Leu Leu Gly Pro Tyr Gln Asp Val Gln Ala Ile Leu | | 7254 |

|     |     |     |     |     |     |     |     |     |     |      |
|-----|-----|-----|-----|-----|-----|-----|-----|-----|-----|------|
|     |     |     | 2405|     |     |     | 2410|     |     | 2415 |
| tct | tat | ggc | gga | gat | gcc | acc | ggg | tta | gcc | aaa ggt tgt aaa gcg | 7299 |
| Ser | Tyr | Gly | Gly | Asp | Ala | Thr | Gly | Leu | Ala | Lys Gly Cys Lys Ala |
|     | 2420|     |     |     | 2425|     |     |     | 2430|      |
| ctg | gca | gtt | tct | cac | gga | atg | aat | gac | agc | ggt cag ttc caa ttg | 7344 |
| Leu | Ala | Val | Ser | His | Gly | Met | Asn | Asp | Ser | Gly Gln Phe Gln Leu |
|     | 2435|     |     |     | 2440|     |     |     | 2445|      |
| gat | ttc | aac | gat | ggc | aaa | ttc | ctg | cca | ttt | gaa gga atc gaa atc | 7389 |
| Asp | Phe | Asn | Asp | Gly | Lys | Phe | Leu | Pro | Phe | Glu Gly Ile Glu Ile |
|     | 2450|     |     |     | 2455|     |     |     | 2460|      |
| gat | aaa | ggt | acg | ctg | aca | tta | agc | ttc | ccg | aat gca acc gaa aaa | 7434 |
| Asp | Lys | Gly | Thr | Leu | Thr | Leu | Ser | Phe | Pro | Asn Ala Thr Glu Lys |
|     | 2465|     |     |     | 2470|     |     |     | 2475|      |
| caa | aaa | acc | atg | ctg | gag | agt | cta | agc | gac | atc att ctg cat att | 7479 |
| Gln | Lys | Thr | Met | Leu | Glu | Ser | Leu | Ser | Asp | Ile Ile Leu His Ile |
|     | 2480|     |     |     | 2485|     |     |     | 2490|      |
| cgc | tac | acc | att | cgc | caa | taa |     |     |     |      | 7500 |
| Arg | Tyr | Thr | Ile | Arg | Gln |     |     |     |     |      |
|     | 2495|     |     |     |     |     |     |     |     |      |

<210> SEQ ID NO 4
<211> LENGTH: 2499
<212> TYPE: PRT
<213> ORGANISM: Photorhabdus luminescens

<400> SEQUENCE: 4

Met Asn Thr Leu Lys Ser Glu Tyr Gln Gln Ala Leu Gly Ala Gly Phe
1               5                   10                  15

Asn Asn Leu Thr Asp Ile Cys His Leu Ser Phe Asp Glu Leu Arg Lys
                20                  25                  30

Lys Val Lys Asp Lys Leu Ser Trp Ser Gln Thr Gln Ser Leu Tyr Leu
            35                  40                  45

Glu Ala Gln Gln Val Gln Lys Asp Asn Leu Leu His Glu Ala Arg Ile
        50                  55                  60

Leu Lys Arg Ala Asn Pro His Leu Gln Ser Ala Val His Leu Ala Leu
65                  70                  75                  80

Thr Ala Pro His Ala Asp Gln Gln Gly Tyr Asn Ser Arg Phe Gly Asn
                85                  90                  95

Arg Ala Ser Lys Tyr Ala Ala Pro Gly Ala Ile Ser Ser Met Phe Ser
            100                 105                 110

Leu Ala Ala Tyr Leu Thr Glu Leu Tyr Arg Gln Ala Arg Asn Leu His
        115                 120                 125

Ala Glu Gly Ser Ile Tyr His Leu Asp Thr Arg Arg Pro Asp Leu Lys
    130                 135                 140

Ser Leu Val Leu Ser Gln Lys Asn Met Asn Thr Glu Ile Ser Thr Leu
145                 150                 155                 160

Ser Leu Ser Asn Asn Met Leu Leu Asn Ser Ile Lys Thr Gln Pro Asn
                165                 170                 175

Leu Asn Ser His Ala Lys Val Met Glu Lys Leu Ser Thr Phe Arg Thr
            180                 185                 190

Ser Gly Ser Met Pro Tyr His Asp Ala Tyr Glu Ser Val Arg Lys Ile
        195                 200                 205

Ile Gln Leu Gln Ala Pro Val Phe Glu Gln Ser Ser Thr Leu Thr Asp
    210                 215                 220

Thr Pro Ile Thr Lys Leu Met Tyr Gln Ile Ser Leu Leu Gly Ile Asn
225                 230                 235                 240

-continued

```
Ala Ser Val Ser Pro Glu Leu Phe Thr Ile Leu Thr Gln Lys Ile Lys
            245                 250                 255

Pro Ala Thr Asn Ala Asp Asn Thr Asn Glu Leu Lys Lys Leu Tyr Lys
            260                 265                 270

Lys Asn Phe Gly Glu Ile Lys Ser Ile Gln Met Ala Arg Ala Glu Tyr
            275                 280                 285

Leu Lys Ser Tyr Tyr Asn Leu Thr Asp Lys Glu Leu Asn Gln Phe Ser
            290                 295                 300

Lys Lys Ile Lys Gln Ile Asp Ser Leu Trp Asn Ile Gly Asp Glu Ile
305                 310                 315                 320

Thr Gln Tyr His Leu Leu Lys Phe Asn Lys Ala Ile Asn Leu Ser Arg
                325                 330                 335

Ser Thr Glu Leu Ser Pro Ile Ile Leu Asn Ser Ile Ala Ile Asp Ile
            340                 345                 350

Leu Lys Lys Thr Pro Pro Glu Asp Asp Ser Asp Asn Pro Phe Arg Asp
            355                 360                 365

Asp Pro Asp Tyr Leu Glu Ser Phe Gln Asp Leu Asp Leu Ser Asp Glu
            370                 375                 380

Pro Asp Ile Asp Glu Asp Val Leu Arg Glu Ala Leu Arg Val Lys Asp
385                 390                 395                 400

Tyr Met Gln Arg Tyr Gly Ile Asp Ala Glu Thr Ala Leu Ile Leu Cys
                405                 410                 415

Lys Ala Pro Ile Ser Glu Asn Pro Ser His Pro Asp Leu Ser Lys Leu
            420                 425                 430

Leu Ala Asp Ile His Gln Leu Thr Ile Asp Glu Leu Gly Val Leu Leu
            435                 440                 445

Val Ala Ile Asp Glu Gly Lys Thr Asp Leu Ser Gln Ile Thr His Asp
450                 455                 460

Asn Leu Ala Val Leu Ile Ser Lys Leu Tyr Ser Val Thr Asn Trp Leu
465                 470                 475                 480

Arg Thr Arg Lys Trp Ser Val Tyr Gln Leu Phe Val Met Thr Thr Asp
                485                 490                 495

Lys Tyr Asn Lys Thr Leu Thr Pro Glu Ile Asn Asn Leu Leu Asp Thr
            500                 505                 510

Val Tyr Asn Gly Leu Gln Asn Phe Tyr Lys Asp Asn Leu Leu Lys Ile
            515                 520                 525

Lys Asp Asn Leu Leu Lys Ala Lys Glu Ser Leu Pro Glu Asp Lys Asp
530                 535                 540

Asn Leu Pro Lys Ala Glu Gln Tyr Leu Leu Glu Ala Glu Lys Tyr Leu
545                 550                 555                 560

Leu Ala Ala Glu Lys Tyr Leu Leu Ala Glu Lys Tyr Leu Leu Glu
                565                 570                 575

Ala Asn Lys Asn Pro Leu Glu Ala Lys Lys Ala Leu Lys Glu Tyr Glu
            580                 585                 590

Lys Asn Gln Glu Ala Tyr Glu Lys Asn Leu Lys Glu His Glu Lys Tyr
            595                 600                 605

Leu Leu Lys Ala Gly Glu Asn Leu Pro Ala Ile Lys Glu Asn Leu Leu
            610                 615                 620

Lys Ile Lys Glu Asn Leu Pro Lys Ala Ile Ser Pro Tyr Ile Ala Ala
625                 630                 635                 640

Ala Leu Gln Leu Pro Ser Glu Asn Val Ala Leu Ser Val Leu Ala Trp
            645                 650                 655

Ala Asp Lys Leu Asn Ser Gly Lys Glu Asn Lys Met Thr Ala Asp Ser
```

```
                    660                 665                 670
Phe Trp Asn Trp Leu Arg Lys Lys Pro Ile Glu Thr Gln Ser Lys Thr
                675                 680                 685
Thr Glu Ala Thr Glu Ala Thr Glu Ala Thr Glu Ala Thr Glu Ala Thr
            690                 695                 700
Glu Ala Thr Glu Lys Thr Thr Leu Ile Gln Gln Ala Val Gln Tyr Cys
705                 710                 715                 720
Gln Cys Leu Ala Gln Leu Ala Leu Ile Tyr Arg Ser Thr Gly Leu Ser
                725                 730                 735
Glu Ser Thr Leu Arg Leu Phe Val Thr Asn Pro Gln Ile Phe Gly Leu
            740                 745                 750
Thr Ala Lys Thr Thr Ser Thr His Asn Val Leu Ser Leu Ile Met Leu
                755                 760                 765
Thr Arg Phe Thr Asp Trp Val Asn Ser Leu Gly Glu Asn Ala Ser Ser
            770                 775                 780
Val Leu Thr Glu Phe Glu Lys Gly Thr Leu Thr Ala Glu Leu Leu Ala
785                 790                 795                 800
Asn Ala Met Asn Leu Asp Lys Asn Leu Leu Glu Gln Ala Ser Thr Gln
                805                 810                 815
Ala Gln Ala Asp Phe Ser Asn Trp Pro Ser Ile Asp Asn Leu Leu Gln
            820                 825                 830
Trp Ile Asn Ile Ser Arg Gln Leu Asn Ile Ser Pro Gln Gly Val Ser
            835                 840                 845
Glu Leu Ala Lys Ile Leu Asp Ile Glu Ser Ser Thr Asn Tyr Ala Gln
        850                 855                 860
Trp Glu Asn Val Ala Ser Ile Leu Thr Ala Gly Leu Asp Thr Gln Lys
865                 870                 875                 880
Ala Asn Thr Leu His Ala Phe Leu Gly Glu Ser Arg Ser Thr Ala Leu
                885                 890                 895
Ser Thr Tyr Tyr Ile Tyr Ser His Asn Gln Lys Asp Arg Glu Glu Arg
            900                 905                 910
Lys His Thr Val Ile Lys Asp Arg Asp Asp Leu Tyr Gln Tyr Leu Leu
        915                 920                 925
Ile Asp Asn Gln Val Ser Ala Ala Ile Lys Thr Thr Glu Ile Ala Glu
    930                 935                 940
Ala Ile Ala Ser Ile Gln Leu Tyr Ile Asn Arg Ala Leu Lys Asn Met
945                 950                 955                 960
Glu Gly Asp Thr Asp Thr Ser Val Thr Ser Arg Leu Phe Phe Thr Asn
                965                 970                 975
Trp Asp Lys Tyr Asn Lys Arg Tyr Ser Thr Trp Ala Gly Ile Thr Lys
            980                 985                 990
Leu Leu Tyr Tyr Pro Glu Asn Tyr  Ile Asp Pro Thr Leu  Arg Ile Gly
        995                 1000                1005
Gln Thr  Lys Met Met Asp Thr  Leu Leu Gln Ser Ile  Ser Gln Ser
    1010                1015                1020
Gln Leu  Asn Thr Asp Thr Val  Glu Asp Ala Phe Lys  Ser Tyr Leu
    1025                1030                1035
Thr Ser  Phe Glu Gln Val Ala  Asn Leu Glu Val Ile  Ser Ala Tyr
    1040                1045                1050
His Asp  Asn Ile Asn Asn Asp  Gln Gly Leu Thr Tyr  Phe Ile Gly
    1055                1060                1065
Arg Ser  Lys Thr Glu Val Asn  Gln Tyr Tyr Trp Arg  Ser Val Asp
    1070                1075                1080
```

-continued

His Asn Lys Phe Ser Glu Gly Lys Phe Pro Ala Asn Ala Trp Ser
    1085                1090                1095

Glu Trp His Lys Ile Asp Cys Pro Ile Asn Pro Tyr Glu Asp Thr
    1100                1105                1110

Ile Arg Pro Val Val Tyr Gln Ser Arg Leu Tyr Ile Ile Trp Leu
    1115                1120                1125

Glu Gln Lys Lys Val Thr Asn Arg Ala Glu Gly Glu Ala Ile Lys
    1130                1135                1140

Gln Gly Ser Lys Thr Thr Thr Ser Tyr His Tyr Glu Leu Lys Leu
    1145                1150                1155

Ala His Ile Arg Tyr Asp Gly Thr Trp Asn Thr Pro Ile Thr Phe
    1160                1165                1170

Asp Val Asp Glu Lys Ile Ser Gly Leu Asn Leu Glu Leu Asn Lys
    1175                1180                1185

Ala Leu Gly Leu Tyr Cys Ala Ser Tyr Gln Gly Lys Asp Lys Leu
    1190                1195                1200

Leu Val Met Phe Tyr Lys Lys Gln Glu Gln Leu Asn Asn Tyr Thr
    1205                1210                1215

Glu Lys Thr Gly Asn Thr Tyr Thr Ala Pro Ile Lys Gly Leu Tyr
    1220                1225                1230

Ile Thr Ser Asn Met Ser Pro Glu Glu Met Thr Pro Glu Ser Tyr
    1235                1240                1245

Arg Leu Asn Ala His Lys Gln Phe Asp Thr Asn Asn Val Val Arg
    1250                1255                1260

Val Asn Asn Arg Tyr Ala Glu Ser Tyr Glu Ile Pro Ser Ser Val
    1265                1270                1275

Asn Ser Asn Asn Gly Tyr Asp Trp Gly Glu Gly Tyr Leu Ser Met
    1280                1285                1290

Val Tyr Gly Gly Ser Ile Leu Ile Thr Arg Asp Pro Ser Asp Asn
    1295                1300                1305

Ser Lys Ile Gln Ile Ser Pro Lys Leu Arg Ile Ile His Asn Gly
    1310                1315                1320

Tyr Glu Gly Arg Gln Arg Asn Gln Cys Asn Leu Met Lys Lys Tyr
    1325                1330                1335

Gly Lys Leu Gly Asp Lys Phe Ile Ile Tyr Thr Thr Leu Gly Ile
    1340                1345                1350

Asn Pro Asn Asn Leu Ser Asn Lys Lys Leu Ile Tyr Pro Val Tyr
    1355                1360                1365

Gln Tyr Glu Gly Asn Glu Ser Lys Leu Ser Gln Gly Arg Leu Leu
    1370                1375                1380

Phe Tyr Arg Asp Ser Thr Thr Asn Phe Thr Arg Ala Trp Phe Pro
    1385                1390                1395

Asn Leu Ser Ser Asp Ser Lys Glu Met Ser Ile Thr Thr Gly Gly
    1400                1405                1410

Asn Ile Ser Gly Asn Tyr Gly Tyr Ile Asp Asn Lys His Ser Asp
    1415                1420                1425

Asn Lys Pro Phe Glu Glu Tyr Phe Tyr Met Asp Asp His Gly Gly
    1430                1435                1440

Ile Asp Thr Asp Val Ser Glu Pro Ile Phe Ile Asn Thr Lys Ile
    1445                1450                1455

Gln Pro Ser Asn Val Lys Ile Ile Val Lys Thr Val Lys Asp Asp
    1460                1465                1470

-continued

```
Gly Lys Leu Asp Ser Lys Pro Tyr Ile Ala Glu Asp Lys Val Ser
    1475            1480                1485

Val Lys Pro Thr Pro Asn Phe Glu Glu Met Cys Tyr Gln Phe Asn
    1490            1495                1500

Asn Leu Asp Gln Ile Asp Val Ser Thr Leu Val Phe Lys Asn Asn
    1505            1510                1515

Glu Ala Ser Ile Asp Ile Thr Phe Thr Ala Ser Ala Asp Ala Phe
    1520            1525                1530

Glu Ser Gly Lys Glu Gln Arg Asn Leu Gly Glu Glu His Phe Ser
    1535            1540                1545

Ile Arg Ile Ile Lys Lys Ala Asn Val Asn Asp Val Leu Thr Leu
    1550            1555                1560

His His Asp Pro Ser Gly Ala Gln Tyr Met Gln Trp Gly Ala Tyr
    1565            1570                1575

Arg Thr Arg Leu Asn Thr Leu Phe Ala Arg Lys Leu Ile Ser Arg
    1580            1585                1590

Ala Asn Ala Gly Ile Asp Thr Ile Leu Ser Met Glu Thr Gln Asn
    1595            1600                1605

Ile Gln Glu Pro Gln Leu Gly Lys Gly Phe Tyr Val Asn Phe Thr
    1610            1615                1620

Leu Pro Lys Tyr Asp Gln Asn Thr His Gly Asn Glu Arg Gln Phe
    1625            1630                1635

Lys Ile His Ile Gly Asn Ile Ala Gly Asp Asn Thr Met Arg Pro
    1640            1645                1650

Tyr Tyr Gln Gly Ile Leu Ala Asp Thr Glu Thr Ser Val Val Leu
    1655            1660                1665

Phe Val Pro Tyr Glu Lys Gln Ser Tyr Thr Asn Glu Gly Val Arg
    1670            1675                1680

Leu Gly Val Glu Tyr Lys Lys Val Ser Tyr Leu Gly Val Trp Glu
    1685            1690                1695

Pro Ala Phe Phe Tyr Phe Asn Glu Ile Gln Gln Lys Phe Ile Leu
    1700            1705                1710

Ile Asn Asp Ala Asp His Asn Ser Ala Met Thr Gln Ser Gly Glu
    1715            1720                1725

Lys Thr Gly Ile Lys Lys Tyr Lys Gly Phe Leu Asp Val Ser Ile
    1730            1735                1740

Leu Ile Asp His Gln His Thr Glu Pro Met Asp Phe Asn Gly Ala
    1745            1750                1755

Asn Ser Leu Tyr Phe Trp Glu Leu Phe Tyr Tyr Thr Pro Met Leu
    1760            1765                1770

Ile Ala Gln Arg Leu Leu His Glu Gln Asn Phe Asp Glu Ala Asn
    1775            1780                1785

Arg Trp Leu Lys Tyr Val Trp Asn Pro Ser Gly His Ile Ala Asn
    1790            1795                1800

Gly Gln Lys Gln His Pro His Asn Trp Asn Val Arg Pro Leu Gln
    1805            1810                1815

Glu Asp Thr Ser Trp Asn Asp Asp Pro Leu Asp Thr Phe Asp Pro
    1820            1825                1830

Asp Ala Ile Ala Gln His Asp Pro Met His Tyr Lys Val Ala Thr
    1835            1840                1845

Phe Met Cys Ala Leu Asp Leu Leu Ile Glu Gln Gly Asp Tyr Ala
    1850            1855                1860

Tyr Arg Gln Leu Glu Arg Asp Thr Leu Ala Glu Ala Lys Met Trp
```

-continued

```
            1865                1870               1875
Tyr Met Gln Ala Leu His Leu Leu Gly Asp Lys Pro His Leu Leu
    1880                1885               1890

Leu Ser Ser Thr Trp Ser Asp Pro Glu Leu Lys Glu Ala Ala Asp
    1895                1900               1905

Leu Glu Lys Gln Gln Ala His Ala Lys Ala Ile Ala Asp Leu Arg
    1910                1915               1920

Gln Gly Gln Pro Lys Asp Gly Ser Asn Thr Asp Leu Phe Leu Pro
    1925                1930               1935

Gln Val Asn Glu Val Met Leu Ser Tyr Trp Gln Lys Leu Glu Gln
    1940                1945               1950

Arg Leu Tyr Asn Leu Arg His Asn Leu Ser Ile Asp Gly Gln Pro
    1955                1960               1965

Leu His Leu Pro Ile Phe Ala Thr Pro Ala Asp Pro Lys Ala Leu
    1970                1975               1980

Leu Ser Ala Ala Val Ala Ser Ser Gln Gly Gly Ser Asn Leu Pro
    1985                1990               1995

Ser Glu Phe Ile Ser Val Trp Arg Phe Pro His Met Leu Glu Asn
    2000                2005               2010

Ala Arg Ser Met Val Ser Gln Leu Thr Gln Phe Gly Ser Thr Leu
    2015                2020               2025

Gln Asn Ile Ile Glu Arg Gln Asp Ala Glu Ala Leu Asn Thr Leu
    2030                2035               2040

Leu Gln Asn Gln Ala Ala Glu Leu Ile Leu Thr Asn Leu Ser Ile
    2045                2050               2055

Gln Asp Lys Thr Ile Glu Glu Leu Asp Val Glu Lys Thr Val Leu
    2060                2065               2070

Glu Lys Thr Arg Ala Gly Ala Lys Ser Arg Phe Asp Ser Tyr Ser
    2075                2080               2085

Lys Phe Tyr Asp Glu Asp Ile Asn Ala Gly Glu Lys Gln Ala Met
    2090                2095               2100

Ala Leu Arg Ala Ser Val Ala Gly Ile Ser Thr Ala Leu Gln Ala
    2105                2110               2115

Ser His Leu Ala Gly Ala Ala Leu Asp Leu Ala Pro Asn Ile Phe
    2120                2125               2130

Gly Phe Ala Asp Gly Gly Ser His Trp Gly Ala Ile Ala Gln Ala
    2135                2140               2145

Thr Ser Asn Val Met Glu Phe Ser Ala Ser Val Met Ser Thr Glu
    2150                2155               2160

Ala Asp Lys Ile Ser Gln Ser Glu Ala Tyr Arg Arg Arg Arg Gln
    2165                2170               2175

Glu Trp Lys Ile Gln Arg Asn Asn Ala Asp Ala Glu Leu Lys Gln
    2180                2185               2190

Ile Asp Ala Gln Leu Gln Ser Leu Val Val Arg Arg Glu Ala Ala
    2195                2200               2205

Val Leu Gln Lys Thr Ser Leu Lys Thr Gln Gln Glu Gln Thr His
    2210                2215               2220

Ala Gln Leu Thr Phe Leu Gln His Lys Phe Ser Asn Gln Ala Leu
    2225                2230               2235

Tyr Asn Trp Leu Arg Gly Arg Leu Ser Ala Ile Tyr Phe Gln Phe
    2240                2245               2250

Tyr Asp Leu Ala Val Ala Arg Cys Leu Met Ala Glu Met Ala Tyr
    2255                2260               2265
```

-continued

```
Arg Trp Glu Thr Asn Asp Ala Ala Arg Phe Ile Lys Pro Gly
    2270            2275            2280

Ala Trp Gln Gly Thr His Ala Gly Leu Leu Ala Gly Glu Thr Leu
    2285            2290            2295

Met Leu Asn Leu Ala Gln Met Glu Asp Ala His Leu Lys Gln Glu
    2300            2305            2310

Gln Arg Val Leu Glu Val Glu Arg Thr Val Ser Leu Ala Glu Val
    2315            2320            2325

Tyr Lys Glu Lys Gly Gln Phe Ser Leu Thr Lys Lys Ile Ala Glu
    2330            2335            2340

Leu Val Asn Lys Lys Pro Asp Thr Thr Ser Ser Arg Asn Asn Thr
    2345            2350            2355

Leu Asn Phe Gly Glu Gly Asn Ala Lys Thr Ser Leu Gln Ala Ser
    2360            2365            2370

Ile Ser Leu Ala Asp Leu Gln Ile Arg His Asp Tyr Pro Glu Asn
    2375            2380            2385

Ser Gly Ala Gly Asn Val Arg Arg Ile Lys Gln Ile Ser Val Thr
    2390            2395            2400

Leu Pro Ala Leu Leu Gly Pro Tyr Gln Asp Val Gln Ala Ile Leu
    2405            2410            2415

Ser Tyr Gly Gly Asp Ala Thr Gly Leu Ala Lys Gly Cys Lys Ala
    2420            2425            2430

Leu Ala Val Ser His Gly Met Asn Asp Ser Gly Gln Phe Gln Leu
    2435            2440            2445

Asp Phe Asn Asp Gly Lys Phe Leu Pro Phe Glu Gly Ile Glu Ile
    2450            2455            2460

Asp Lys Gly Thr Leu Thr Leu Ser Phe Pro Asn Ala Thr Glu Lys
    2465            2470            2475

Gln Lys Thr Met Leu Glu Ser Leu Ser Asp Ile Ile Leu His Ile
    2480            2485            2490

Arg Tyr Thr Ile Arg Gln
    2495
```

<210> SEQ ID NO 5
<211> LENGTH: 6534
<212> TYPE: DNA
<213> ORGANISM: Photorhabdus luminescens
<220> FEATURE:
<221> NAME/KEY: CDS
<222> LOCATION: (1)..(6531)

<400> SEQUENCE: 5

```
atg agc aca atc acg cca gaa cac cct gaa atg gca caa cag gca caa     48
Met Ser Thr Ile Thr Pro Glu His Pro Glu Met Ala Gln Gln Ala Gln
1               5                   10                  15 aaa gca aac cga ctg cat gag gcg agt atc ctc aaa cgt gct aac ccc     96
Lys Ala Asn Arg Leu His Glu Ala Ser Ile Leu Lys Arg Ala Asn Pro
            20                  25                  30 caa tta caa aat gcg gta cat ctt gct tta acc aca ccc cat gct gac    144
Gln Leu Gln Asn Ala Val His Leu Ala Leu Thr Thr Pro His Ala Asp
        35                  40                  45 cag caa ggt tat aac agt aaa ttt ggt ggc cgc gcc agc cag tat gtc    192
Gln Gln Gly Tyr Asn Ser Lys Phe Gly Gly Arg Ala Ser Gln Tyr Val
    50                  55                  60 gct ccc ggc gca gtt gct tcc atg ttc tct ccc gcc gct tat ctg acc    240
Ala Pro Gly Ala Val Ala Ser Met Phe Ser Pro Ala Ala Tyr Leu Thr
65                  70                  75                  80
```

```
gaa ctt tat cgt cag gca cag gat tta cat aaa aaa gag tcc att tat       288
Glu Leu Tyr Arg Gln Ala Gln Asp Leu His Lys Lys Glu Ser Ile Tyr
             85                  90                  95 cat ctg gat aaa cgc cgc cct gat tta aaa tca ctg aca ctc agc cag       336
His Leu Asp Lys Arg Arg Pro Asp Leu Lys Ser Leu Thr Leu Ser Gln
        100                 105                 110 caa aat atg gat gat gaa gtt tct aca ctt tct cta tct aat aag gtg       384
Gln Asn Met Asp Asp Glu Val Ser Thr Leu Ser Leu Ser Asn Lys Val
            115                 120                 125 ttg ctg gaa ggg atc aag acg ctg acc ggg ctg gaa ggc cat act aac       432
Leu Leu Glu Gly Ile Lys Thr Leu Thr Gly Leu Glu Gly His Thr Asn
130                 135                 140 gtg atg aaa gcg cta tca acc ttt cgc tct tct ggc tct ctg cca tat       480
Val Met Lys Ala Leu Ser Thr Phe Arg Ser Ser Gly Ser Leu Pro Tyr
145                 150                 155                 160 cac gat gct tac gaa agt gta cgt aag gtt att caa tta caa gct ccg       528
His Asp Ala Tyr Glu Ser Val Arg Lys Val Ile Gln Leu Gln Ala Pro
                165                 170                 175 ata ttc gac caa gtt ggt cca tcc cca gaa aca gat atc gcc aat ctg       576
Ile Phe Asp Gln Val Gly Pro Ser Pro Glu Thr Asp Ile Ala Asn Leu
            180                 185                 190 aca tat caa gct tcc ctg ctg gga att aat gct tct gtc ttg cct gaa       624
Thr Tyr Gln Ala Ser Leu Leu Gly Ile Asn Ala Ser Val Leu Pro Glu
        195                 200                 205 ttg ttt aag act ctg aca gaa gag atc acc gaa gtt aat gca aat gag       672
Leu Phe Lys Thr Leu Thr Glu Glu Ile Thr Glu Val Asn Ala Asn Glu
210                 215                 220 aag ttt aag aaa aac ttt ggg gat aga gag cca tca gaa ctt ctc act       720
Lys Phe Lys Lys Asn Phe Gly Asp Arg Glu Pro Ser Glu Leu Leu Thr
225                 230                 235                 240 ctg gat gcc ttg aaa cac tat tac aat tta acc aat gaa gaa tta gaa       768
Leu Asp Ala Leu Lys His Tyr Tyr Asn Leu Thr Asn Glu Glu Leu Glu
                245                 250                 255 cag ttt tta aat cac gta tta ata gaa agt aac tct act tac aca aat       816
Gln Phe Leu Asn His Val Leu Ile Glu Ser Asn Ser Thr Tyr Thr Asn
            260                 265                 270 aac caa ctt att aat ata agc att gat aca tca ggt aag ata caa ttg       864
Asn Gln Leu Ile Asn Ile Ser Ile Asp Thr Ser Gly Lys Ile Gln Leu
        275                 280                 285 agc cgc ata aca cga aca cct gac tta aat tat aac aac ctc aat tac       912
Ser Arg Ile Thr Arg Thr Pro Asp Leu Asn Tyr Asn Asn Leu Asn Tyr
290                 295                 300 atg aat tta tat cct att caa aac aga cgt ttt tat gtt gat att agc       960
Met Asn Leu Tyr Pro Ile Gln Asn Arg Arg Phe Tyr Val Asp Ile Ser
305                 310                 315                 320 tat aag aaa aaa gct ggg caa gtt agt att aga ctc agc aag ccc cag      1008
Tyr Lys Lys Lys Ala Gly Gln Val Ser Ile Arg Leu Ser Lys Pro Gln
                325                 330                 335 tct aaa tat ctc aaa ggt ata tat aaa gcg acc ata gaa aac acg aac      1056
Ser Lys Tyr Leu Lys Gly Ile Tyr Lys Ala Thr Ile Glu Asn Thr Asn
            340                 345                 350 tat tct tcc cca aca ttt gaa tta acc gac aaa gat att caa aaa gaa      1104
Tyr Ser Ser Pro Thr Phe Glu Leu Thr Asp Lys Asp Ile Gln Lys Glu
        355                 360                 365 ttt act ctt cta agt tat cgt tat aaa gaa aat agt gat tcg aat ata      1152
Phe Thr Leu Leu Ser Tyr Arg Tyr Lys Glu Asn Ser Asp Ser Asn Ile
370                 375                 380 tct gac tca tct tat gcc aag ttc aaa att cag gat tat tca cct gca      1200
Ser Asp Ser Ser Tyr Ala Lys Phe Lys Ile Gln Asp Tyr Ser Pro Ala
```

```
                385                 390                 395                 400
att ttt ctg tta aaa ctt aat aaa acc att cgt ttg tcc cac gca aca      1248
Ile Phe Leu Leu Lys Leu Asn Lys Thr Ile Arg Leu Ser His Ala Thr
                        405                 410                 415 aaa ctt ctg cca aca gta ctg gaa aaa att gtc ttc aat atc aat cag      1296
Lys Leu Leu Pro Thr Val Leu Glu Lys Ile Val Phe Asn Ile Asn Gln
                420                 425                 430 aaa cta gat atc aat gca gaa ata tta aag aaa ata ttt cgc gtt aaa      1344
Lys Leu Asp Ile Asn Ala Glu Ile Leu Lys Lys Ile Phe Arg Val Lys
            435                 440                 445 tac tat atg caa cgt tac ggt att gat gct gag act gca ttg gta ctg      1392
Tyr Tyr Met Gln Arg Tyr Gly Ile Asp Ala Glu Thr Ala Leu Val Leu
        450                 455                 460 tgc aaa gta tca act aat ata att aat cct tct agt tcc gat cta atc      1440
Cys Lys Val Ser Thr Asn Ile Ile Asn Pro Ser Ser Ser Asp Leu Ile
465                 470                 475                 480 aaa tta cta gca aat att cat cag tta act gtt aat gag ctg aat tta      1488
Lys Leu Leu Ala Asn Ile His Gln Leu Thr Val Asn Glu Leu Asn Leu
                        485                 490                 495 ctg ctg gtt gcc ata ggt gaa gga tca acc aat cta tct gag ctc agt      1536
Leu Leu Val Ala Ile Gly Glu Gly Ser Thr Asn Leu Ser Glu Leu Ser
                500                 505                 510 gat aac aat cta tct gtt ctg att gat aaa ctt tat agc att acc cag      1584
Asp Asn Asn Leu Ser Val Leu Ile Asp Lys Leu Tyr Ser Ile Thr Gln
            515                 520                 525 tgg ttg cgt aca cgg aaa tgg aat atg tac ctg ctg ttt atg atg act      1632
Trp Leu Arg Thr Arg Lys Trp Asn Met Tyr Leu Leu Phe Met Met Thr
        530                 535                 540 acc acc gac tat aac caa acc ctg acg ccg gaa att cag aac ctg cta      1680
Thr Thr Asp Tyr Asn Gln Thr Leu Thr Pro Glu Ile Gln Asn Leu Leu
545                 550                 555                 560 gat gct gtt tac aat ggt ttg caa aac ttt aac agt aaa aac gaa gca      1728
Asp Ala Val Tyr Asn Gly Leu Gln Asn Phe Asn Ser Lys Asn Glu Ala
                        565                 570                 575 aat ctt ctg ttg aag atc tcg cct tac atc gcc gcc gct ctg caa ttg      1776
Asn Leu Leu Leu Lys Ile Ser Pro Tyr Ile Ala Ala Ala Leu Gln Leu
                580                 585                 590 ccg tct gaa aat acc gct tat tat ata ctc aac tgg gca gat caa cta      1824
Pro Ser Glu Asn Thr Ala Tyr Tyr Ile Leu Asn Trp Ala Asp Gln Leu
            595                 600                 605 aaa cct ggc tct ggt gca atg aca gca aca aaa ttc tgg gaa tgg ttg      1872
Lys Pro Gly Ser Gly Ala Met Thr Ala Thr Lys Phe Trp Glu Trp Leu
        610                 615                 620 caa gct tca cat aat cca gag caa tca acc gct ata aca gaa gaa caa      1920
Gln Ala Ser His Asn Pro Glu Gln Ser Thr Ala Ile Thr Glu Glu Gln
625                 630                 635                 640 gca gtc caa tat tgc caa tgc ctg gca caa ttg gca ctg att tat cgt      1968
Ala Val Gln Tyr Cys Gln Cys Leu Ala Gln Leu Ala Leu Ile Tyr Arg
                        645                 650                 655 tcc acc ggc ctt agc gaa agc act tta cgt ctg ttt gtc aca aaa cca      2016
Ser Thr Gly Leu Ser Glu Ser Thr Leu Arg Leu Phe Val Thr Lys Pro
                660                 665                 670 caa ctc ttt ggc ttt acc gaa gga aca gcg tca aca cac aat gca tta      2064
Gln Leu Phe Gly Phe Thr Glu Gly Thr Ala Ser Thr His Asn Ala Leu
            675                 680                 685 tca ctg ata aag ctg aca cgt ttt act gac tgg gtt aac tct ctg ggt      2112
Ser Leu Ile Lys Leu Thr Arg Phe Thr Asp Trp Val Asn Ser Leu Gly
        690                 695                 700 gaa aaa gcc tct tct gta ctg acc gaa ttt gag aag gga aca tta aca      2160
```

```
                                              -continued

Glu Lys Ala Ser Ser Val Leu Thr Glu Phe Glu Lys Gly Thr Leu Thr
705                 710                 715                 720 gca gaa cta ttg gct aac gcc ctg agt ctt gat aaa aat cta ctg gag   2208
Ala Glu Leu Leu Ala Asn Ala Leu Ser Leu Asp Lys Asn Leu Leu Glu
                725                 730                 735 caa gcc agt aat caa gca caa gtt aat ttc acc gac tgg ccg tct atc   2256
Gln Ala Ser Asn Gln Ala Gln Val Asn Phe Thr Asp Trp Pro Ser Ile
            740                 745                 750 gat acc atc cag caa tgg att aac att gcg cgt caa ttg aat atc tct   2304
Asp Thr Ile Gln Gln Trp Ile Asn Ile Ala Arg Gln Leu Asn Ile Ser
        755                 760                 765 cca caa gac gtt tct gca cta gcg caa gta ctc acc aca gaa tcc tcc   2352
Pro Gln Asp Val Ser Ala Leu Ala Gln Val Leu Thr Thr Glu Ser Ser
    770                 775                 780 gat aac tat gcc gaa tgg gaa aac gtc gcg gcg aca tta acc gcc gga   2400
Asp Asn Tyr Ala Glu Trp Glu Asn Val Ala Ala Thr Leu Thr Ala Gly
785                 790                 795                 800 ctg gac acc caa aaa gcc aac gcc ctg cac acc ttt ctg gat gaa tct   2448
Leu Asp Thr Gln Lys Ala Asn Ala Leu His Thr Phe Leu Asp Glu Ser
                805                 810                 815 cgt agt gct gca tta agc gag tac tat atc cgt aaa gtc gct aac gca   2496
Arg Ser Ala Ala Leu Ser Glu Tyr Tyr Ile Arg Lys Val Ala Asn Ala
            820                 825                 830 ggt gca aaa gtt aaa aac cat gat gat ctg tac cag tat tta ttg att   2544
Gly Ala Lys Val Lys Asn His Asp Asp Leu Tyr Gln Tyr Leu Leu Ile
        835                 840                 845 gat aac caa gtt tcc gcc gcc atc aaa acc acc ccg att gca gaa gct   2592
Asp Asn Gln Val Ser Ala Ala Ile Lys Thr Thr Pro Ile Ala Glu Ala
    850                 855                 860 atc gcc agc atc caa ctg tat att aac cgg gca ctg aaa aat atg gag   2640
Ile Ala Ser Ile Gln Leu Tyr Ile Asn Arg Ala Leu Lys Asn Met Glu
865                 870                 875                 880 gaa aac gcg gtt tcg cag gtc gtc act cga cca ttc ttt acc gat tgg   2688
Glu Asn Ala Val Ser Gln Val Val Thr Arg Pro Phe Phe Thr Asp Trp
                885                 890                 895 gac aaa tac aat aaa cgc tac agc acc tgg gcc agc att gct aaa ctc   2736
Asp Lys Tyr Asn Lys Arg Tyr Ser Thr Trp Ala Ser Ile Ala Lys Leu
            900                 905                 910 att tac tac cct gag aat tac atc gat ccg aca ata cgc atc ggg cga   2784
Ile Tyr Tyr Pro Glu Asn Tyr Ile Asp Pro Thr Ile Arg Ile Gly Arg
        915                 920                 925 aca aaa atg atg gat aca ttg ctg caa tcc atc agc cag agt caa tta   2832
Thr Lys Met Met Asp Thr Leu Leu Gln Ser Ile Ser Gln Ser Gln Leu
    930                 935                 940 aat acc gat acg gta gaa gac gcc ttt atg tct tat ctg acg tcg ttc   2880
Asn Thr Asp Thr Val Glu Asp Ala Phe Met Ser Tyr Leu Thr Ser Phe
945                 950                 955                 960 gaa cag ata gct aat ctg gaa gtc gtc agc gcc tat cat gac aat gcc   2928
Glu Gln Ile Ala Asn Leu Glu Val Val Ser Ala Tyr His Asp Asn Ala
                965                 970                 975 aaa gat gat caa aga tta acc tat ttt atc ggg cac agt aaa acc gaa   2976
Lys Asp Asp Gln Arg Leu Thr Tyr Phe Ile Gly His Ser Lys Thr Glu
            980                 985                 990 gtt aat caa tat tac tgg cgt aac  gtg gat cac aat aaa  ttc agc gac   3024
Val Asn Gln Tyr Tyr Trp Arg Asn  Val Asp His Asn Lys  Phe Ser Asp
        995                 1000                1005 gat aaa  ttc cct gcc aat gcc  tgg agt gag tgg cac  aaa att gat     3069
Asp Lys  Phe Pro Ala Asn Ala  Trp Ser Glu Trp His  Lys Ile Asp
    1010                1015                1020
```

-continued

| | | |
|---|---|---|
| tgt cca ata aat ccc tat cag ggc act atc cat ccg gta att ttc<br>Cys Pro Ile Asn Pro Tyr Gln Gly Thr Ile His Pro Val Ile Phe<br>1025                          1030                         1035 | 3114 |
| caa tcc cga ctg tat ctg atc tgg ttg gag cag aag aaa att gct<br>Gln Ser Arg Leu Tyr Leu Ile Trp Leu Glu Gln Lys Lys Ile Ala<br>      1040                         1045                        1050 | 3159 |
| aaa cag gca gat aat aat caa acc gtt gaa gat tat tat tat gaa<br>Lys Gln Ala Asp Asn Asn Gln Thr Val Glu Asp Tyr Tyr Tyr Glu<br>1055                          1060                         1065 | 3204 |
| cta aaa cta gca cat atc cgt tat gac ggt act tgg aat aca cca<br>Leu Lys Leu Ala His Ile Arg Tyr Asp Gly Thr Trp Asn Thr Pro<br>1070                          1075                        1080 | 3249 |
| gta gcc ttt aat atc aat gac aaa gta tct gct gtt tta aaa atg<br>Val Ala Phe Asn Ile Asn Asp Lys Val Ser Ala Val Leu Lys Met<br>      1085                         1090                        1095 | 3294 |
| tca aat cca cca gca act tcg gaa tta tta gag tca cca gag tca<br>Ser Asn Pro Pro Ala Thr Ser Glu Leu Leu Glu Ser Pro Glu Ser<br>1100                          1105                         1110 | 3339 |
| tta aaa cta gga ttc tat tgt aca aat cat caa gac aat aaa ttg<br>Leu Lys Leu Gly Phe Tyr Cys Thr Asn His Gln Asp Asn Lys Leu<br>1115                          1120                         1125 | 3384 |
| ctg gta atg ttt tat cgc aaa cga gat gaa ctg gat gaa tat aag<br>Leu Val Met Phe Tyr Arg Lys Arg Asp Glu Leu Asp Glu Tyr Lys<br>1130                          1135                         1140 | 3429 |
| aga aca tta aaa gag tta gca gaa gca gaa aaa aag gta aaa gaa<br>Arg Thr Leu Lys Glu Leu Ala Glu Ala Glu Lys Lys Val Lys Glu<br>1145                          1150                         1155 | 3474 |
| ata gca aaa aaa att gat cgc gaa gat gga ata tca gta tct gat<br>Ile Ala Lys Lys Ile Asp Arg Glu Asp Gly Ile Ser Val Ser Asp<br>1160                          1165                         1170 | 3519 |
| cat caa gaa aaa caa aca gca gaa aag aaa tta aaa gaa tta ata<br>His Gln Glu Lys Gln Thr Ala Glu Lys Lys Leu Lys Glu Leu Ile<br>1175                          1180                         1185 | 3564 |
| caa gag tta atg caa gga gtg tat atc tcc tcc aat atg tta ttg<br>Gln Glu Leu Met Gln Gly Val Tyr Ile Ser Ser Asn Met Leu Leu<br>1190                          1195                         1200 | 3609 |
| gaa aat ata gaa tct gaa cag tac aaa aat att tat gaa ctc acc<br>Glu Asn Ile Glu Ser Glu Gln Tyr Lys Asn Ile Tyr Glu Leu Thr<br>1205                          1210                         1215 | 3654 |
| tat agt aaa ttt gat att aac aat atc ata aag gtg aat agc tgg<br>Tyr Ser Lys Phe Asp Ile Asn Asn Ile Ile Lys Val Asn Ser Trp<br>1220                          1225                         1230 | 3699 |
| aat cct gtt acc gat gag gtt aac gac gat aat atc ctg act gtt<br>Asn Pro Val Thr Asp Glu Val Asn Asp Asp Asn Ile Leu Thr Val<br>1235                          1240                         1245 | 3744 |
| cac aat gat aca aac ggg gcg caa tat atg cag tcg gga ggt tat<br>His Asn Asp Thr Asn Gly Ala Gln Tyr Met Gln Ser Gly Gly Tyr<br>1250                          1255                         1260 | 3789 |
| cgt act cgc ctt aat acg ctg ttt gcc cgt aaa tta att agt cgc<br>Arg Thr Arg Leu Asn Thr Leu Phe Ala Arg Lys Leu Ile Ser Arg<br>1265                          1270                         1275 | 3834 |
| gcc acg gcc gga ata gat act att tta aat ata gag acg cag aaa<br>Ala Thr Ala Gly Ile Asp Thr Ile Leu Asn Ile Glu Thr Gln Lys<br>1280                          1285                         1290 | 3879 |
| ctg cca gaa cct cag tta ggg aaa gga ttt ttt act aat ctc att<br>Leu Pro Glu Pro Gln Leu Gly Lys Gly Phe Phe Thr Asn Leu Ile<br>1295                          1300                         1305 | 3924 |
| ctt cct aaa tat gac caa aat gta cat ggc agc gaa cgt tgg ttt<br>Leu Pro Lys Tyr Asp Gln Asn Val His Gly Ser Glu Arg Trp Phe<br>1310                          1315                         1320 | 3969 |

```
aaa att cat ata aga aat gat aat aaa atg atg aac tta tac cac      4014
Lys Ile His Ile Arg Asn Asp Asn Lys Met Met Asn Leu Tyr His
    1325                1330                1335 aaa gga aca cta act gat act gaa act agc gtc act ctt ttt atc      4059
Lys Gly Thr Leu Thr Asp Thr Glu Thr Ser Val Thr Leu Phe Ile
    1340                1345                1350 cct tgg tct aat aca caa gaa cgc gtc gaa ata gca gta gaa tat      4104
Pro Trp Ser Asn Thr Gln Glu Arg Val Glu Ile Ala Val Glu Tyr
    1355                1360                1365 aat aag aag ttc tat aag gat caa caa aac tgg gaa act gct tta      4149
Asn Lys Lys Phe Tyr Lys Asp Gln Gln Asn Trp Glu Thr Ala Leu
    1370                1375                1380 ttt cat ttt aat gaa act aat cag aaa ttt atg ttg gtt aat gat      4194
Phe His Phe Asn Glu Thr Asn Gln Lys Phe Met Leu Val Asn Asp
    1385                1390                1395 gct gat aat aag caa gta gta ata aac gat act gat gca atc gtc      4239
Ala Asp Asn Lys Gln Val Val Ile Asn Asp Thr Asp Ala Ile Val
    1400                1405                1410 aat aaa tat aaa ggc ttt ctt gat gtt tcc att ctt atc gat cag      4284
Asn Lys Tyr Lys Gly Phe Leu Asp Val Ser Ile Leu Ile Asp Gln
    1415                1420                1425 cac acg gaa cca atg gat ttc agc ggt gct aac agc ctc tat ttt      4329
His Thr Glu Pro Met Asp Phe Ser Gly Ala Asn Ser Leu Tyr Phe
    1430                1435                1440 tgg gaa cta ttc tac tat gcc cca atg ctg att gct cag cgc ctg      4374
Trp Glu Leu Phe Tyr Tyr Ala Pro Met Leu Ile Ala Gln Arg Leu
    1445                1450                1455 cta cac gaa caa cac ttc gat gaa gcc aac cgt tgg ttg aaa tat      4419
Leu His Glu Gln His Phe Asp Glu Ala Asn Arg Trp Leu Lys Tyr
    1460                1465                1470 atc tgg aat cca tct ggt tat att gag cat ggt cag att cag cac      4464
Ile Trp Asn Pro Ser Gly Tyr Ile Glu His Gly Gln Ile Gln His
    1475                1480                1485 tac cgc tgg aat gtc cgc cca tta ttg gaa gat atc agt tgg aac      4509
Tyr Arg Trp Asn Val Arg Pro Leu Leu Glu Asp Ile Ser Trp Asn
    1490                1495                1500 gat gat cca ctg aat tca gtc gat ccc gat gcc ata gca caa tat      4554
Asp Asp Pro Leu Asn Ser Val Asp Pro Asp Ala Ile Ala Gln Tyr
    1505                1510                1515 gat cca atg cac tat aaa gtc gtt act ttt atg cgc acc ctt gat      4599
Asp Pro Met His Tyr Lys Val Val Thr Phe Met Arg Thr Leu Asp
    1520                1525                1530 ctg ttg ctg gac cgt gga gat tac gcc tat cgt cag tta gaa cgg      4644
Leu Leu Leu Asp Arg Gly Asp Tyr Ala Tyr Arg Gln Leu Glu Arg
    1535                1540                1545 gac acg ctt aat gaa gct aag atg tgg tat atg caa gca ctg cat      4689
Asp Thr Leu Asn Glu Ala Lys Met Trp Tyr Met Gln Ala Leu His
    1550                1555                1560 ctg tta ggc gat aaa cct cat cta tct ttc agt tca acg tgg cgt      4734
Leu Leu Gly Asp Lys Pro His Leu Ser Phe Ser Ser Thr Trp Arg
    1565                1570                1575 aaa ccg agt tta ggt gac gct gcc aga acg gaa aaa cag gag gaa      4779
Lys Pro Ser Leu Gly Asp Ala Ala Arg Thr Glu Lys Gln Glu Glu
    1580                1585                1590 caa gcc cat gca atg act gcc ctg cga caa ggt gat att agt cgg      4824
Gln Ala His Ala Met Thr Ala Leu Arg Gln Gly Asp Ile Ser Arg
    1595                1600                1605 cac aac cac ccg aca gat ctt ttc ttg cca cag gtc aat gaa gtg      4869
His Asn His Pro Thr Asp Leu Phe Leu Pro Gln Val Asn Glu Val
```

```
                   1610                1615                 1620
atg caa  aac tac tgg cag  aaa ctg gag  caa cgg  ctg tac aac ctg         4914
Met Gln  Asn Tyr Trp Gln  Lys Leu Glu  Gln Arg  Leu Tyr Asn Leu
    1625              1630                 1635 cgc cat  aat ctc tct atc  gac ggc caa  ctg cta  cat ctg cct att         4959
Arg His  Asn Leu Ser Ile  Asp Gly Gln  Leu Leu  His Leu Pro Ile
    1640              1645                 1650 tac gct  aca ccg gca gat  cca aaa gcg  tta ctc  agt gcc gct gtt         5004
Tyr Ala  Thr Pro Ala Asp  Pro Lys Ala  Leu Leu  Ser Ala Ala Val
    1655              1660                 1665 gcc aac  tca caa ggc gga  agc aag tta  cca atg  tca ttt atg tca         5049
Ala Asn  Ser Gln Gly Gly  Ser Lys Leu  Pro Met  Ser Phe Met Ser
    1670              1675                 1680 ctg tgg  cgt ttc cca cag  atg ttg gaa  aac gcg  cgc ggt atg gta         5094
Leu Trp  Arg Phe Pro Gln  Met Leu Glu  Asn Ala  Arg Gly Met Val
    1685              1690                 1695 agc cag  tta aca cag ttc  ggc tcc acg  tta caa  aat att atc gaa         5139
Ser Gln  Leu Thr Gln Phe  Gly Ser Thr  Leu Gln  Asn Ile Ile Glu
    1700              1705                 1710 cgt cag  gat gcg gaa gcc  tta aac acg  cta ttg  cag aat caa gcg         5184
Arg Gln  Asp Ala Glu Ala  Leu Asn Thr  Leu Leu  Gln Asn Gln Ala
    1715              1720                 1725 gca gaa  ctg ata ttg act  aat ctc agc  ata cag  gac aaa acc ctg         5229
Ala Glu  Leu Ile Leu Thr  Asn Leu Ser  Ile Gln  Asp Lys Thr Leu
    1730              1735                 1740 gaa gag  ctg gat gcg gaa  aaa atc gta  ctg gag  aaa tcc aaa gct         5274
Glu Glu  Leu Asp Ala Glu  Lys Ile Val  Leu Glu  Lys Ser Lys Ala
    1745              1750                 1755 gga gcg  caa tca cgc ttt  aac agc tac  aaa aag  cta tac gat gaa         5319
Gly Ala  Gln Ser Arg Phe  Asn Ser Tyr  Lys Lys  Leu Tyr Asp Glu
    1760              1765                 1770 aat atc  aat gcg ggt gaa  aac cgg gta  ata gca  ttg cat tcc tcc         5364
Asn Ile  Asn Ala Gly Glu  Asn Arg Val  Ile Ala  Leu His Ser Ser
    1775              1780                 1785 gtt gct  ggc ctt agc act  gcc ctg caa  gca tcg  cgt ctg gca ggc         5409
Val Ala  Gly Leu Ser Thr  Ala Leu Gln  Ala Ser  Arg Leu Ala Gly
    1790              1795                 1800 gcc gcc  ctt gat ctg gcg  ccc aac att  ttc ggc  ttc gct gat ggc         5454
Ala Ala  Leu Asp Leu Ala  Pro Asn Ile  Phe Gly  Phe Ala Asp Gly
    1805              1810                 1815 ggc agc  cgt tgg ggg gca  att gcc gaa  gcg aca  ggt aat gtc atg         5499
Gly Ser  Arg Trp Gly Ala  Ile Ala Glu  Ala Thr  Gly Asn Val Met
    1820              1825                 1830 gaa ttc  tcc gca aat gtt  atg aac acc  gaa gcg  gat aaa atc agc         5544
Glu Phe  Ser Ala Asn Val  Met Asn Thr  Glu Ala  Asp Lys Ile Ser
    1835              1840                 1845 cag tct  gaa acc tat cgc  cgt cgc cgt  cag gag  tgg gaa atc caa         5589
Gln Ser  Glu Thr Tyr Arg  Arg Arg Arg  Gln Glu  Trp Glu Ile Gln
    1850              1855                 1860 cgt aac  aat gcc gaa gca  gag ata aaa  caa atc  gat gcc caa ctt         5634
Arg Asn  Asn Ala Glu Ala  Glu Ile Lys  Gln Ile  Asp Ala Gln Leu
    1865              1870                 1875 caa tcg  ttg gca gta cgc  cgt gaa gct  gcg gtg  ttg cag aaa acc         5679
Gln Ser  Leu Ala Val Arg  Arg Glu Ala  Ala Val  Leu Gln Lys Thr
    1880              1885                 1890 agc ctg  aaa acc caa cag  gaa cag act  cag gcg  caa ttg act ttc         5724
Ser Leu  Lys Thr Gln Gln  Glu Gln Thr  Gln Ala  Gln Leu Thr Phe
    1895              1900                 1905 cta caa  cgt aaa ttc agt  aat caa gcg  ttg tac  cac tgg cta cgt         5769
```

-continued

```
Leu Gln Arg Lys Phe Ser Asn Gln Ala Leu Tyr His Trp Leu Arg
    1910                1915                1920 ggt cgg cta gct gct atc tac ttc caa ttt tac gat ttg gcc gta        5814
Gly Arg Leu Ala Ala Ile Tyr Phe Gln Phe Tyr Asp Leu Ala Val
    1925                1930                1935 acc cgt tgt ctg atg gca gaa atg gct tat cgt tgg gag act cat        5859
Thr Arg Cys Leu Met Ala Glu Met Ala Tyr Arg Trp Glu Thr His
    1940                1945                1950 aat acc aca gca agc ttt atc aaa ccc ggc gcc tgg cag ggg acg        5904
Asn Thr Thr Ala Ser Phe Ile Lys Pro Gly Ala Trp Gln Gly Thr
    1955                1960                1965 cac gct ggt ctg ctc gcc ggt gaa acc ttg atg ctg aat ctg gca        5949
His Ala Gly Leu Leu Ala Gly Glu Thr Leu Met Leu Asn Leu Ala
    1970                1975                1980 caa atg gag gat gct tat ttg aga tgg gat caa cgc gct ctg gaa        5994
Gln Met Glu Asp Ala Tyr Leu Arg Trp Asp Gln Arg Ala Leu Glu
    1985                1990                1995 gtg gaa cgt act att tca ctg gcg caa ctc tat gga aca cta cca        6039
Val Glu Arg Thr Ile Ser Leu Ala Gln Leu Tyr Gly Thr Leu Pro
    2000                2005                2010 gaa aaa tca ttt aat ttg gca aca cgt att tct gcc cta cta aca        6084
Glu Lys Ser Phe Asn Leu Ala Thr Arg Ile Ser Ala Leu Leu Thr
    2015                2020                2025 ggt agt aca act gaa ccc gtt gag gag cat ccc gtt aca tta gaa        6129
Gly Ser Thr Thr Glu Pro Val Glu Glu His Pro Val Thr Leu Glu
    2030                2035                2040 aac ggt caa cta agc gcc aaa atc tct ctg tca ggt ctg tca cta        6174
Asn Gly Gln Leu Ser Ala Lys Ile Ser Leu Ser Gly Leu Ser Leu
    2045                2050                2055 cat aat gac tac cca gaa ggc aat ggc gta ggc aac att cgg cgc        6219
His Asn Asp Tyr Pro Glu Gly Asn Gly Val Gly Asn Ile Arg Arg
    2060                2065                2070 att aaa cag atc agt gtc acc ctg cca gct ctg tta ggg cca tac        6264
Ile Lys Gln Ile Ser Val Thr Leu Pro Ala Leu Leu Gly Pro Tyr
    2075                2080                2085 caa aat gta caa gcc att ttg gcc tac gag gga agt gaa atc gga        6309
Gln Asn Val Gln Ala Ile Leu Ala Tyr Glu Gly Ser Glu Ile Gly
    2090                2095                2100 tta gct gag agc tgt aaa tca ctg gca att tct cat ggg gtt aat        6354
Leu Ala Glu Ser Cys Lys Ser Leu Ala Ile Ser His Gly Val Asn
    2105                2110                2115 gac agt ggt caa ttc cag ttg gat ttc aac aat ggt aaa ttc ctg        6399
Asp Ser Gly Gln Phe Gln Leu Asp Phe Asn Asn Gly Lys Phe Leu
    2120                2125                2130 ccg ttt gaa ggg ata gcg att aac gat acc ggc aca tta aca ctc        6444
Pro Phe Glu Gly Ile Ala Ile Asn Asp Thr Gly Thr Leu Thr Leu
    2135                2140                2145 aat ttc ccg aat gcg acc ggc aaa cag caa gcc atg tta caa gca        6489
Asn Phe Pro Asn Ala Thr Gly Lys Gln Gln Ala Met Leu Gln Ala
    2150                2155                2160 ttg agc gat att att ctg cat att cgc tac acc atc cgc caa taa        6534
Leu Ser Asp Ile Ile Leu His Ile Arg Tyr Thr Ile Arg Gln
    2165                2170                2175
```

<210> SEQ ID NO 6
<211> LENGTH: 2177
<212> TYPE: PRT
<213> ORGANISM: Photorhabdus luminescens

<400> SEQUENCE: 6

-continued

```
Met Ser Thr Ile Thr Pro Glu His Pro Glu Met Ala Gln Gln Ala Gln
1               5                   10                  15

Lys Ala Asn Arg Leu His Glu Ala Ser Ile Leu Lys Arg Ala Asn Pro
                20                  25                  30

Gln Leu Gln Asn Ala Val His Leu Ala Leu Thr Thr Pro His Ala Asp
            35                  40                  45

Gln Gln Gly Tyr Asn Ser Lys Phe Gly Gly Arg Ala Ser Gln Tyr Val
        50                  55                  60

Ala Pro Gly Ala Val Ala Ser Met Phe Ser Pro Ala Ala Tyr Leu Thr
65                  70                  75                  80

Glu Leu Tyr Arg Gln Ala Gln Asp Leu His Lys Lys Glu Ser Ile Tyr
                85                  90                  95

His Leu Asp Lys Arg Arg Pro Asp Leu Lys Ser Leu Thr Leu Ser Gln
            100                 105                 110

Gln Asn Met Asp Asp Glu Val Ser Thr Leu Ser Leu Ser Asn Lys Val
        115                 120                 125

Leu Leu Glu Gly Ile Lys Thr Leu Thr Gly Leu Gly His Thr Asn
130                 135                 140

Val Met Lys Ala Leu Ser Thr Phe Arg Ser Ser Gly Ser Leu Pro Tyr
145                 150                 155                 160

His Asp Ala Tyr Glu Ser Val Arg Lys Val Ile Gln Leu Gln Ala Pro
                165                 170                 175

Ile Phe Asp Gln Val Gly Pro Ser Pro Glu Thr Asp Ile Ala Asn Leu
            180                 185                 190

Thr Tyr Gln Ala Ser Leu Leu Gly Ile Asn Ala Ser Val Leu Pro Glu
        195                 200                 205

Leu Phe Lys Thr Leu Thr Glu Glu Ile Thr Glu Val Asn Ala Asn Glu
210                 215                 220

Lys Phe Lys Lys Asn Phe Gly Asp Arg Glu Pro Ser Glu Leu Leu Thr
225                 230                 235                 240

Leu Asp Ala Leu Lys His Tyr Tyr Asn Leu Thr Asn Glu Glu Leu Glu
                245                 250                 255

Gln Phe Leu Asn His Val Leu Ile Glu Ser Asn Ser Thr Tyr Thr Asn
            260                 265                 270

Asn Gln Leu Ile Asn Ile Ser Ile Asp Thr Ser Gly Lys Ile Gln Leu
        275                 280                 285

Ser Arg Ile Thr Arg Thr Pro Asp Leu Asn Tyr Asn Asn Leu Asn Tyr
290                 295                 300

Met Asn Leu Tyr Pro Ile Gln Asn Arg Arg Phe Tyr Val Asp Ile Ser
305                 310                 315                 320

Tyr Lys Lys Lys Ala Gly Gln Val Ser Ile Arg Leu Ser Lys Pro Gln
                325                 330                 335

Ser Lys Tyr Leu Lys Gly Ile Tyr Lys Ala Thr Ile Glu Asn Thr Asn
            340                 345                 350

Tyr Ser Ser Pro Thr Phe Glu Leu Thr Asp Lys Asp Ile Gln Lys Glu
        355                 360                 365

Phe Thr Leu Leu Ser Tyr Arg Tyr Lys Glu Asn Ser Asp Ser Asn Ile
370                 375                 380

Ser Asp Ser Ser Tyr Ala Lys Phe Lys Ile Gln Asp Tyr Ser Pro Ala
385                 390                 395                 400

Ile Phe Leu Leu Lys Leu Asn Lys Thr Ile Arg Leu Ser His Ala Thr
                405                 410                 415

Lys Leu Leu Pro Thr Val Leu Glu Lys Ile Val Phe Asn Ile Asn Gln
```

-continued

```
                420             425             430
Lys Leu Asp Ile Asn Ala Glu Ile Leu Lys Lys Ile Phe Arg Val Lys
            435                 440                 445

Tyr Tyr Met Gln Arg Tyr Gly Ile Asp Ala Glu Thr Ala Leu Val Leu
        450                 455                 460

Cys Lys Val Ser Thr Asn Ile Ile Asn Pro Ser Ser Ser Asp Leu Ile
465                 470                 475                 480

Lys Leu Leu Ala Asn Ile His Gln Leu Thr Val Asn Glu Leu Asn Leu
                485                 490                 495

Leu Leu Val Ala Ile Gly Glu Gly Ser Thr Asn Leu Ser Glu Leu Ser
            500                 505                 510

Asp Asn Asn Leu Ser Val Leu Ile Asp Lys Leu Tyr Ser Ile Thr Gln
        515                 520                 525

Trp Leu Arg Thr Arg Lys Trp Asn Met Tyr Leu Leu Phe Met Met Thr
    530                 535                 540

Thr Thr Asp Tyr Asn Gln Thr Leu Thr Pro Glu Ile Gln Asn Leu Leu
545                 550                 555                 560

Asp Ala Val Tyr Asn Gly Leu Gln Asn Phe Asn Ser Lys Asn Glu Ala
                565                 570                 575

Asn Leu Leu Lys Ile Ser Pro Tyr Ile Ala Ala Leu Gln Leu
            580                 585                 590

Pro Ser Glu Asn Thr Ala Tyr Tyr Ile Leu Asn Trp Ala Asp Gln Leu
        595                 600                 605

Lys Pro Gly Ser Gly Ala Met Thr Ala Thr Lys Phe Trp Glu Trp Leu
    610                 615                 620

Gln Ala Ser His Asn Pro Glu Gln Ser Thr Ala Ile Thr Glu Glu Gln
625                 630                 635                 640

Ala Val Gln Tyr Cys Gln Cys Leu Ala Gln Leu Ala Leu Ile Tyr Arg
                645                 650                 655

Ser Thr Gly Leu Ser Glu Ser Thr Leu Arg Leu Phe Val Thr Lys Pro
            660                 665                 670

Gln Leu Phe Gly Phe Thr Glu Gly Thr Ala Ser Thr His Asn Ala Leu
        675                 680                 685

Ser Leu Ile Lys Leu Thr Arg Phe Thr Asp Trp Val Asn Ser Leu Gly
    690                 695                 700

Glu Lys Ala Ser Ser Val Leu Thr Glu Phe Glu Lys Gly Thr Leu Thr
705                 710                 715                 720

Ala Glu Leu Leu Ala Asn Ala Leu Ser Leu Asp Lys Asn Leu Leu Glu
                725                 730                 735

Gln Ala Ser Asn Gln Ala Gln Val Asn Phe Thr Asp Trp Pro Ser Ile
            740                 745                 750

Asp Thr Ile Gln Gln Trp Ile Asn Ile Ala Arg Gln Leu Asn Ile Ser
        755                 760                 765

Pro Gln Asp Val Ser Ala Leu Ala Gln Val Leu Thr Thr Glu Ser Ser
    770                 775                 780

Asp Asn Tyr Ala Glu Trp Glu Asn Val Ala Ala Thr Leu Thr Ala Gly
785                 790                 795                 800

Leu Asp Thr Gln Lys Ala Asn Ala Leu His Thr Phe Leu Asp Glu Ser
                805                 810                 815

Arg Ser Ala Ala Leu Ser Glu Tyr Tyr Ile Arg Lys Val Ala Asn Ala
            820                 825                 830

Gly Ala Lys Val Lys Asn His Asp Asp Leu Tyr Gln Tyr Leu Leu Ile
        835                 840                 845
```

-continued

Asp Asn Gln Val Ser Ala Ala Ile Lys Thr Thr Pro Ile Ala Glu Ala
    850                 855                 860

Ile Ala Ser Ile Gln Leu Tyr Ile Asn Arg Ala Leu Lys Asn Met Glu
865                 870                 875                 880

Glu Asn Ala Val Ser Gln Val Val Thr Arg Pro Phe Phe Thr Asp Trp
                885                 890                 895

Asp Lys Tyr Asn Lys Arg Tyr Ser Thr Trp Ala Ser Ile Ala Lys Leu
            900                 905                 910

Ile Tyr Tyr Pro Glu Asn Tyr Ile Asp Pro Thr Ile Arg Ile Gly Arg
        915                 920                 925

Thr Lys Met Met Asp Thr Leu Leu Gln Ser Ile Ser Gln Ser Gln Leu
    930                 935                 940

Asn Thr Asp Thr Val Glu Asp Ala Phe Met Ser Tyr Leu Thr Ser Phe
945                 950                 955                 960

Glu Gln Ile Ala Asn Leu Glu Val Val Ser Ala Tyr His Asp Asn Ala
                965                 970                 975

Lys Asp Asp Gln Arg Leu Thr Tyr Phe Ile Gly His Ser Lys Thr Glu
            980                 985                 990

Val Asn Gln Tyr Tyr Trp Arg Asn Val Asp His Asn Lys Phe Ser Asp
        995                 1000                1005

Asp Lys Phe Pro Ala Asn Ala Trp Ser Glu Trp His Lys Ile Asp
    1010                1015                1020

Cys Pro Ile Asn Pro Tyr Gln Gly Thr Ile His Pro Val Ile Phe
    1025                1030                1035

Gln Ser Arg Leu Tyr Leu Ile Trp Leu Glu Gln Lys Lys Ile Ala
    1040                1045                1050

Lys Gln Ala Asp Asn Asn Gln Thr Val Glu Asp Tyr Tyr Tyr Glu
    1055                1060                1065

Leu Lys Leu Ala His Ile Arg Tyr Asp Gly Thr Trp Asn Thr Pro
    1070                1075                1080

Val Ala Phe Asn Ile Asn Asp Lys Val Ser Ala Val Leu Lys Met
    1085                1090                1095

Ser Asn Pro Pro Ala Thr Ser Glu Leu Leu Glu Ser Pro Glu Ser
    1100                1105                1110

Leu Lys Leu Gly Phe Tyr Cys Thr Asn His Gln Asp Asn Lys Leu
    1115                1120                1125

Leu Val Met Phe Tyr Arg Lys Arg Asp Glu Leu Asp Glu Tyr Lys
    1130                1135                1140

Arg Thr Leu Lys Glu Leu Ala Glu Ala Glu Lys Lys Val Lys Glu
    1145                1150                1155

Ile Ala Lys Lys Ile Asp Arg Glu Asp Gly Ile Ser Val Ser Asp
    1160                1165                1170

His Gln Glu Lys Gln Thr Ala Glu Lys Lys Leu Lys Glu Leu Ile
    1175                1180                1185

Gln Glu Leu Met Gln Gly Val Tyr Ile Ser Ser Asn Met Leu Leu
    1190                1195                1200

Glu Asn Ile Glu Ser Glu Gln Tyr Lys Asn Ile Tyr Glu Leu Thr
    1205                1210                1215

Tyr Ser Lys Phe Asp Ile Asn Asn Ile Ile Lys Val Asn Ser Trp
    1220                1225                1230

Asn Pro Val Thr Asp Glu Val Asn Asp Asp Asn Ile Leu Thr Val
    1235                1240                1245

```
His Asn Asp Thr Asn Gly Ala Gln Tyr Met Gln Ser Gly Gly Tyr
1250              1255                 1260

Arg Thr Arg Leu Asn Thr Leu Phe Ala Arg Lys Leu Ile Ser Arg
1265              1270                 1275

Ala Thr Ala Gly Ile Asp Thr Ile Leu Asn Ile Glu Thr Gln Lys
1280              1285                 1290

Leu Pro Glu Pro Gln Leu Gly Lys Gly Phe Phe Thr Asn Leu Ile
1295              1300                 1305

Leu Pro Lys Tyr Asp Gln Asn Val His Gly Ser Glu Arg Trp Phe
1310              1315                 1320

Lys Ile His Ile Arg Asn Asp Asn Lys Met Met Asn Leu Tyr His
1325              1330                 1335

Lys Gly Thr Leu Thr Asp Thr Glu Thr Ser Val Thr Leu Phe Ile
1340              1345                 1350

Pro Trp Ser Asn Thr Gln Glu Arg Val Glu Ile Ala Val Glu Tyr
1355              1360                 1365

Asn Lys Lys Phe Tyr Lys Asp Gln Gln Asn Trp Glu Thr Ala Leu
1370              1375                 1380

Phe His Phe Asn Glu Thr Asn Gln Lys Phe Met Leu Val Asn Asp
1385              1390                 1395

Ala Asp Asn Lys Gln Val Val Ile Asn Asp Thr Asp Ala Ile Val
1400              1405                 1410

Asn Lys Tyr Lys Gly Phe Leu Asp Val Ser Ile Leu Ile Asp Gln
1415              1420                 1425

His Thr Glu Pro Met Asp Phe Ser Gly Ala Asn Ser Leu Tyr Phe
1430              1435                 1440

Trp Glu Leu Phe Tyr Tyr Ala Pro Met Leu Ile Ala Gln Arg Leu
1445              1450                 1455

Leu His Glu Gln His Phe Asp Glu Ala Asn Arg Trp Leu Lys Tyr
1460              1465                 1470

Ile Trp Asn Pro Ser Gly Tyr Ile Glu His Gly Gln Ile Gln His
1475              1480                 1485

Tyr Arg Trp Asn Val Arg Pro Leu Leu Glu Asp Ile Ser Trp Asn
1490              1495                 1500

Asp Asp Pro Leu Asn Ser Val Asp Pro Asp Ala Ile Ala Gln Tyr
1505              1510                 1515

Asp Pro Met His Tyr Lys Val Val Thr Phe Met Arg Thr Leu Asp
1520              1525                 1530

Leu Leu Leu Asp Arg Gly Asp Tyr Ala Tyr Arg Gln Leu Glu Arg
1535              1540                 1545

Asp Thr Leu Asn Glu Ala Lys Met Trp Tyr Met Gln Ala Leu His
1550              1555                 1560

Leu Leu Gly Asp Lys Pro His Leu Ser Phe Ser Ser Thr Trp Arg
1565              1570                 1575

Lys Pro Ser Leu Gly Asp Ala Ala Arg Thr Glu Lys Gln Glu Glu
1580              1585                 1590

Gln Ala His Ala Met Thr Ala Leu Arg Gln Gly Asp Ile Ser Arg
1595              1600                 1605

His Asn His Pro Thr Asp Leu Phe Leu Pro Gln Val Asn Glu Val
1610              1615                 1620

Met Gln Asn Tyr Trp Gln Lys Leu Glu Gln Arg Leu Tyr Asn Leu
1625              1630                 1635

Arg His Asn Leu Ser Ile Asp Gly Gln Leu Leu His Leu Pro Ile
```

-continued

```
           1640                1645                1650

Tyr Ala Thr Pro Ala Asp Pro Lys Ala Leu Leu Ser Ala Ala Val
    1655                1660                1665

Ala Asn Ser Gln Gly Gly Ser Lys Leu Pro Met Ser Phe Met Ser
    1670                1675                1680

Leu Trp Arg Phe Pro Gln Met Leu Glu Asn Ala Arg Gly Met Val
    1685                1690                1695

Ser Gln Leu Thr Gln Phe Gly Ser Thr Leu Gln Asn Ile Ile Glu
    1700                1705                1710

Arg Gln Asp Ala Glu Ala Leu Asn Thr Leu Leu Gln Asn Gln Ala
    1715                1720                1725

Ala Glu Leu Ile Leu Thr Asn Leu Ser Ile Gln Asp Lys Thr Leu
    1730                1735                1740

Glu Glu Leu Asp Ala Glu Lys Ile Val Leu Glu Lys Ser Lys Ala
    1745                1750                1755

Gly Ala Gln Ser Arg Phe Asn Ser Tyr Lys Lys Leu Tyr Asp Glu
    1760                1765                1770

Asn Ile Asn Ala Gly Glu Asn Arg Val Ile Ala Leu His Ser Ser
    1775                1780                1785

Val Ala Gly Leu Ser Thr Ala Leu Gln Ala Ser Arg Leu Ala Gly
    1790                1795                1800

Ala Ala Leu Asp Leu Ala Pro Asn Ile Phe Gly Phe Ala Asp Gly
    1805                1810                1815

Gly Ser Arg Trp Gly Ala Ile Ala Glu Ala Thr Gly Asn Val Met
    1820                1825                1830

Glu Phe Ser Ala Asn Val Met Asn Thr Glu Ala Asp Lys Ile Ser
    1835                1840                1845

Gln Ser Glu Thr Tyr Arg Arg Arg Gln Glu Trp Glu Ile Gln
    1850                1855                1860

Arg Asn Asn Ala Glu Ala Glu Ile Lys Gln Ile Asp Ala Gln Leu
    1865                1870                1875

Gln Ser Leu Ala Val Arg Arg Glu Ala Ala Val Leu Gln Lys Thr
    1880                1885                1890

Ser Leu Lys Thr Gln Gln Glu Gln Thr Gln Ala Gln Leu Thr Phe
    1895                1900                1905

Leu Gln Arg Lys Phe Ser Asn Gln Ala Leu Tyr His Trp Leu Arg
    1910                1915                1920

Gly Arg Leu Ala Ala Ile Tyr Phe Gln Phe Tyr Asp Leu Ala Val
    1925                1930                1935

Thr Arg Cys Leu Met Ala Glu Met Ala Tyr Arg Trp Glu Thr His
    1940                1945                1950

Asn Thr Thr Ala Ser Phe Ile Lys Pro Gly Ala Trp Gln Gly Thr
    1955                1960                1965

His Ala Gly Leu Leu Ala Gly Glu Thr Leu Met Leu Asn Leu Ala
    1970                1975                1980

Gln Met Glu Asp Ala Tyr Leu Arg Trp Asp Gln Arg Ala Leu Glu
    1985                1990                1995

Val Glu Arg Thr Ile Ser Leu Ala Gln Leu Tyr Gly Thr Leu Pro
    2000                2005                2010

Glu Lys Ser Phe Asn Leu Ala Thr Arg Ile Ser Ala Leu Leu Thr
    2015                2020                2025

Gly Ser Thr Thr Glu Pro Val Glu Glu His Pro Val Thr Leu Glu
    2030                2035                2040
```

```
Asn Gly Gln Leu Ser Ala Lys Ile Ser Leu Ser Gly Leu Ser Leu
    2045                2050                2055

His Asn Asp Tyr Pro Glu Gly Asn Gly Val Gly Asn Ile Arg Arg
    2060                2065                2070

Ile Lys Gln Ile Ser Val Thr Leu Pro Ala Leu Leu Gly Pro Tyr
    2075                2080                2085

Gln Asn Val Gln Ala Ile Leu Ala Tyr Glu Gly Ser Glu Ile Gly
    2090                2095                2100

Leu Ala Glu Ser Cys Lys Ser Leu Ala Ile Ser His Gly Val Asn
    2105                2110                2115

Asp Ser Gly Gln Phe Gln Leu Asp Phe Asn Asn Gly Lys Phe Leu
    2120                2125                2130

Pro Phe Glu Gly Ile Ala Ile Asn Asp Thr Gly Thr Leu Thr Leu
    2135                2140                2145

Asn Phe Pro Asn Ala Thr Gly Lys Gln Gln Ala Met Leu Gln Ala
    2150                2155                2160

Leu Ser Asp Ile Ile Leu His Ile Arg Tyr Thr Ile Arg Gln
    2165                2170                2175

<210> SEQ ID NO 7
<211> LENGTH: 7146
<212> TYPE: DNA
<213> ORGANISM: Photorhabdus luminescens
<220> FEATURE:
<221> NAME/KEY: CDS
<222> LOCATION: (1)..(7143)

<400> SEQUENCE: 7
```

| | | | | | | | | | | | | | | | | |
|---|---|---|---|---|---|---|---|---|---|---|---|---|---|---|---|---|
| atg | aac | tca | tac | gtg | aaa | gag | ata | cct | gat | gta | tta | caa | agc | caa | tat | 48 |
| Met | Asn | Ser | Tyr | Val | Lys | Glu | Ile | Pro | Asp | Val | Leu | Gln | Ser | Gln | Tyr | |
| 1 | | | | 5 | | | | | 10 | | | | | 15 | | |
| ggt | att | aat | tgt | ctg | aca | gat | att | tgc | cac | tat | tct | ttt | aat | gaa | ttt | 96 |
| Gly | Ile | Asn | Cys | Leu | Thr | Asp | Ile | Cys | His | Tyr | Ser | Phe | Asn | Glu | Phe | |
| | | 20 | | | | | 25 | | | | | 30 | | | | |
| cgt | cag | caa | gtc | tct | gat | cat | ctc | tcc | tgg | tca | gag | acc | aac | cgc | tta | 144 |
| Arg | Gln | Gln | Val | Ser | Asp | His | Leu | Ser | Trp | Ser | Glu | Thr | Asn | Arg | Leu | |
| | 35 | | | | | 40 | | | | | 45 | | | | | |
| tat | cgt | gat | gca | caa | cag | gaa | caa | aaa | gag | aat | caa | tta | tat | gaa | gct | 192 |
| Tyr | Arg | Asp | Ala | Gln | Gln | Glu | Gln | Lys | Glu | Asn | Gln | Leu | Tyr | Glu | Ala | |
| 50 | | | | | 55 | | | | | 60 | | | | | | |
| cgt | att | ctt | aaa | cgc | gct | aac | ccg | cag | ttg | caa | aat | gca | gtg | cac | ctc | 240 |
| Arg | Ile | Leu | Lys | Arg | Ala | Asn | Pro | Gln | Leu | Gln | Asn | Ala | Val | His | Leu | |
| 65 | | | | | 70 | | | | | 75 | | | | | 80 | |
| ggt | att | acc | ctc | cct | cat | gct | gaa | tta | cga | ggc | tat | aat | agt | gaa | ttc | 288 |
| Gly | Ile | Thr | Leu | Pro | His | Ala | Glu | Leu | Arg | Gly | Tyr | Asn | Ser | Glu | Phe | |
| | | | | 85 | | | | | 90 | | | | | 95 | | |
| ggt | ggc | cga | gcc | agc | caa | tat | gtg | gcg | ccg | ggt | tcg | gtt | tcc | tct | atg | 336 |
| Gly | Gly | Arg | Ala | Ser | Gln | Tyr | Val | Ala | Pro | Gly | Ser | Val | Ser | Ser | Met | |
| | | | | 100 | | | | | 105 | | | | | 110 | | |
| ttc | tcc | ccc | gca | gct | tat | tta | act | gaa | ctc | tat | cgt | gaa | gca | cgt | aat | 384 |
| Phe | Ser | Pro | Ala | Ala | Tyr | Leu | Thr | Glu | Leu | Tyr | Arg | Glu | Ala | Arg | Asn | |
| | | | 115 | | | | | 120 | | | | | 125 | | | |
| tta | cat | gcc | agc | gac | tcc | gtt | tat | cat | ctg | gat | gaa | cgc | cgc | cca | gac | 432 |
| Leu | His | Ala | Ser | Asp | Ser | Val | Tyr | His | Leu | Asp | Glu | Arg | Arg | Pro | Asp | |
| | | 130 | | | | | 135 | | | | | 140 | | | | |
| ctc | caa | tca | atg | acg | ctc | agc | cag | caa | aat | atg | gat | acc | gaa | ctt | tcc | 480 |
| Leu | Gln | Ser | Met | Thr | Leu | Ser | Gln | Gln | Asn | Met | Asp | Thr | Glu | Leu | Ser | |
| 145 | | | | | 150 | | | | | 155 | | | | | 160 | |

```
act ctt tct ctg tct aat gaa att ttg ttg aaa gga att aaa gct aat      528
Thr Leu Ser Leu Ser Asn Glu Ile Leu Leu Lys Gly Ile Lys Ala Asn
            165                 170                 175 cag tct aat ctg gac agc gat act aag gtg atg gaa atg tta tcc act      576
Gln Ser Asn Leu Asp Ser Asp Thr Lys Val Met Glu Met Leu Ser Thr
        180                 185                 190 ttc cgt cct tcc ggc acg ata cct tat cat gat gct tac gaa aat gta      624
Phe Arg Pro Ser Gly Thr Ile Pro Tyr His Asp Ala Tyr Glu Asn Val
    195                 200                 205 cgt aaa gct atc caa tta caa gat ccg aaa ctt gaa caa ttt cag aaa      672
Arg Lys Ala Ile Gln Leu Gln Asp Pro Lys Leu Glu Gln Phe Gln Lys
210                 215                 220 tca ccg gcg gtc gcc gga tta atg cat caa gct tca tta tta gga att      720
Ser Pro Ala Val Ala Gly Leu Met His Gln Ala Ser Leu Leu Gly Ile
225                 230                 235                 240 aat aac tct atc tca cca gaa ctg ttt aat att ctg aca gaa gag att      768
Asn Asn Ser Ile Ser Pro Glu Leu Phe Asn Ile Leu Thr Glu Glu Ile
            245                 250                 255 acc gaa gct aac gca gag gca att tat aaa cag aat ttt ggc gat att      816
Thr Glu Ala Asn Ala Glu Ala Ile Tyr Lys Gln Asn Phe Gly Asp Ile
        260                 265                 270 gac cct gcc tgc ctg gca atg ccg gaa tat ctg aaa agt tat tat aat      864
Asp Pro Ala Cys Leu Ala Met Pro Glu Tyr Leu Lys Ser Tyr Tyr Asn
    275                 280                 285 ttt agt gat gaa gaa ctc agt caa ttt att cgc aaa tat cca gat aat      912
Phe Ser Asp Glu Glu Leu Ser Gln Phe Ile Arg Lys Tyr Pro Asp Asn
290                 295                 300 gaa cta aat act cag aaa ata cat tta cta aaa atc aat aaa att att      960
Glu Leu Asn Thr Gln Lys Ile His Leu Leu Lys Ile Asn Lys Ile Ile
305                 310                 315                 320 tta tta tcg caa gcc gtg aat ctg ccg ttt tta aag tta gat gaa att     1008
Leu Leu Ser Gln Ala Val Asn Leu Pro Phe Leu Lys Leu Asp Glu Ile
            325                 330                 335 att cca gaa cag aac att acc ccg aca gta tta ggg aaa atc ttt cta     1056
Ile Pro Glu Gln Asn Ile Thr Pro Thr Val Leu Gly Lys Ile Phe Leu
        340                 345                 350 gtt aaa tat tat atg cag aaa tac aat att ggt acg gaa act gcc tta     1104
Val Lys Tyr Tyr Met Gln Lys Tyr Asn Ile Gly Thr Glu Thr Ala Leu
    355                 360                 365 ata tta tgt aat gat tcc att tca caa tac tcc tat agt aat caa cct     1152
Ile Leu Cys Asn Asp Ser Ile Ser Gln Tyr Ser Tyr Ser Asn Gln Pro
370                 375                 380 agc caa ttt gat cgc cta ttt aat acc tcg cca ctc aat gga caa tat     1200
Ser Gln Phe Asp Arg Leu Phe Asn Thr Ser Pro Leu Asn Gly Gln Tyr
385                 390                 395                 400 ttc gtt atc gaa gac act aat att gac cta agt ctg aac agt acc gat     1248
Phe Val Ile Glu Asp Thr Asn Ile Asp Leu Ser Leu Asn Ser Thr Asp
            405                 410                 415 aac tgg cac aaa gca gta ctt aaa cgt gct ttt aat gtc gat gat att     1296
Asn Trp His Lys Ala Val Leu Lys Arg Ala Phe Asn Val Asp Asp Ile
        420                 425                 430 tcc ctc tat cgt tta ctc cat att gcc aat cat aac aat acc gat gga     1344
Ser Leu Tyr Arg Leu Leu His Ile Ala Asn His Asn Asn Thr Asp Gly
    435                 440                 445 aaa att gct aat aat ata aaa aat ctt tcc aat ctt tat atg act aaa     1392
Lys Ile Ala Asn Asn Ile Lys Asn Leu Ser Asn Leu Tyr Met Thr Lys
450                 455                 460 cta ctg gca gat att cat caa tta acg att gat gaa ctg tat tta cta     1440
Leu Leu Ala Asp Ile His Gln Leu Thr Ile Asp Glu Leu Tyr Leu Leu
465                 470                 475                 480
```

```
                                                                          -continued ctg ata act att ggt gaa gat aaa ata aat tta tat gat att gat gat           1488
Leu Ile Thr Ile Gly Glu Asp Lys Ile Asn Leu Tyr Asp Ile Asp Asp
            485                 490                 495 aaa gag ctg gag aaa ctc ata aac aga ctc gat acc cta agc aat tgg           1536
Lys Glu Leu Glu Lys Leu Ile Asn Arg Leu Asp Thr Leu Ser Asn Trp
        500                 505                 510 ctg cat aca caa aag tgg agt atc tat cag tta ttt ttg atg acc acc           1584
Leu His Thr Gln Lys Trp Ser Ile Tyr Gln Leu Phe Leu Met Thr Thr
    515                 520                 525 acc aac tat gac aaa aca cta acg cct gaa att caa aac tta ctc gat           1632
Thr Asn Tyr Asp Lys Thr Leu Thr Pro Glu Ile Gln Asn Leu Leu Asp
530                 535                 540 acg gtc tac aat ggc tta cag aac ttc gat aaa aat aaa acc aaa ctt           1680
Thr Val Tyr Asn Gly Leu Gln Asn Phe Asp Lys Asn Lys Thr Lys Leu
545                 550                 555                 560 ctg gca gcc atc gcg cct tat att gct gca aca cta caa tta cca tct           1728
Leu Ala Ala Ile Ala Pro Tyr Ile Ala Ala Thr Leu Gln Leu Pro Ser
                565                 570                 575 gaa aat gtc gca cat tct att ctt ctc tgg gct gat aag ata aaa cca           1776
Glu Asn Val Ala His Ser Ile Leu Leu Trp Ala Asp Lys Ile Lys Pro
            580                 585                 590 agc gaa aat aaa ata acg gca gaa aaa ttt tgg atc tgg tta caa aat           1824
Ser Glu Asn Lys Ile Thr Ala Glu Lys Phe Trp Ile Trp Leu Gln Asn
        595                 600                 605 aga gat act aca gaa ttg tca aaa ccg cca gaa atg cag gaa caa att           1872
Arg Asp Thr Thr Glu Leu Ser Lys Pro Pro Glu Met Gln Glu Gln Ile
    610                 615                 620 att cag tac tgc cac tgt ctg gca caa ttg aca atg att tat cgt tct           1920
Ile Gln Tyr Cys His Cys Leu Ala Gln Leu Thr Met Ile Tyr Arg Ser
625                 630                 635                 640 tcc ggc att aat gaa aac gct ttc cgt cta ttt atc gaa aag cca act           1968
Ser Gly Ile Asn Glu Asn Ala Phe Arg Leu Phe Ile Glu Lys Pro Thr
                645                 650                 655 att ttt ggc atc cct gat gaa ccg aat aaa gcg aca cca gcc cat aat           2016
Ile Phe Gly Ile Pro Asp Glu Pro Asn Lys Ala Thr Pro Ala His Asn
            660                 665                 670 gca cca aca tta atc atc cta acc cgc ttt gcc aat tgg gtt aat tct           2064
Ala Pro Thr Leu Ile Ile Leu Thr Arg Phe Ala Asn Trp Val Asn Ser
        675                 680                 685 cta ggt gaa aaa gcc tcc cct att cta acg gct ttt gaa aat aaa acc           2112
Leu Gly Glu Lys Ala Ser Pro Ile Leu Thr Ala Phe Glu Asn Lys Thr
    690                 695                 700 tta act gcg gaa aaa tta gct aac gcc atg aat ctt gat gct aat tta           2160
Leu Thr Ala Glu Lys Leu Ala Asn Ala Met Asn Leu Asp Ala Asn Leu
705                 710                 715                 720 ctg gaa caa gcc agt att caa gca caa aat tat aag cag gtt act aaa           2208
Leu Glu Gln Ala Ser Ile Gln Ala Gln Asn Tyr Lys Gln Val Thr Lys
                725                 730                 735 gaa aat aca ttc tcc aat tgg caa tcc atc gac att att ctg caa tgg           2256
Glu Asn Thr Phe Ser Asn Trp Gln Ser Ile Asp Ile Ile Leu Gln Trp
            740                 745                 750 act aat ata gcc agt aat tta aat atc tcc cca caa ggt att tcc cct           2304
Thr Asn Ile Ala Ser Asn Leu Asn Ile Ser Pro Gln Gly Ile Ser Pro
        755                 760                 765 cta ata gca ttg gat tat ata aaa ccg gct caa aaa aca ccg act tat           2352
Leu Ile Ala Leu Asp Tyr Ile Lys Pro Ala Gln Lys Thr Pro Thr Tyr
    770                 775                 780 gcc caa tgg gaa aat gca gct ata gca tta act gcc ggg tta gac act           2400
Ala Gln Trp Glu Asn Ala Ala Ile Ala Leu Thr Ala Gly Leu Asp Thr
```

-continued

```
            785                 790                 795                 800
caa caa act cat act cta cac gta ttt ctg gac gaa tct cgc agt acc        2448
Gln Gln Thr His Thr Leu His Val Phe Leu Asp Glu Ser Arg Ser Thr
                805                 810                 815 gca tta agc aac tat tat att ggc aag gtt gct aat cgg gca gca tca        2496
Ala Leu Ser Asn Tyr Tyr Ile Gly Lys Val Ala Asn Arg Ala Ala Ser
                820                 825                 830 att aaa agc cgt gac gat tta tac caa tac tta ctg att gat aat caa        2544
Ile Lys Ser Arg Asp Asp Leu Tyr Gln Tyr Leu Leu Ile Asp Asn Gln
            835                 840                 845 gtt tcc gct gaa ata aaa act aca cgt att gcc gaa gcc att gcc agt        2592
Val Ser Ala Glu Ile Lys Thr Thr Arg Ile Ala Glu Ala Ile Ala Ser
850                 855                 860 atc caa ttg tat gtc aac cga gcg ctg gaa aat ata gaa atc cat gcc        2640
Ile Gln Leu Tyr Val Asn Arg Ala Leu Glu Asn Ile Glu Ile His Ala
865                 870                 875                 880 gtt tct gat gtt att acc cgt caa ttt ttt atc gat tgg gat aaa tat        2688
Val Ser Asp Val Ile Thr Arg Gln Phe Phe Ile Asp Trp Asp Lys Tyr
                885                 890                 895 aat aaa cgt tac agt act tgg gct ggc gtt tca caa tta gtt tac tat        2736
Asn Lys Arg Tyr Ser Thr Trp Ala Gly Val Ser Gln Leu Val Tyr Tyr
                900                 905                 910 ccc gaa aat tat atc gac ccg acg atg cgt atc gga caa acg aaa atg        2784
Pro Glu Asn Tyr Ile Asp Pro Thr Met Arg Ile Gly Gln Thr Lys Met
            915                 920                 925 atg gat acg tta ttg caa tcc gtc agc cag agc caa tta aat gcc gat        2832
Met Asp Thr Leu Leu Gln Ser Val Ser Gln Ser Gln Leu Asn Ala Asp
930                 935                 940 acg gta gaa gat gca ttt aaa tct tac ctg acc tcg ttt gaa caa gtc        2880
Thr Val Glu Asp Ala Phe Lys Ser Tyr Leu Thr Ser Phe Glu Gln Val
945                 950                 955                 960 gct aat ttg gaa gtc att agt gct tat cat gat aac gtt aat aat gac        2928
Ala Asn Leu Glu Val Ile Ser Ala Tyr His Asp Asn Val Asn Asn Asp
                965                 970                 975 caa gga ctg acc tat ttt atc ggg aac agc aaa aca gaa gtt aat caa        2976
Gln Gly Leu Thr Tyr Phe Ile Gly Asn Ser Lys Thr Glu Val Asn Gln
            980                 985                 990 tat tac tgg cgc agc gtc gat cac agt aaa ttc aac gac ggt aaa ttc        3024
Tyr Tyr Trp Arg Ser Val Asp His Ser Lys Phe Asn Asp Gly Lys Phe
            995                 1000                1005 gct gct  aat gcc tgg agt gaa  tgg cac aaa att gac  tgc gca att         3069
Ala Ala  Asn Ala Trp Ser Glu  Trp His Lys Ile Asp  Cys Ala Ile
1010                 1015                 1020 aat ccc tac caa agc acc att cgc cca gtt atc tat  aaa tcc cga          3114
Asn Pro Tyr Gln Ser Thr Ile Arg Pro Val Ile Tyr  Lys Ser Arg
1025                 1030                 1035 tta tat  ctg att tgg ctg gaa  caa aaa gaa aca gct  aaa caa aag        3159
Leu Tyr  Leu Ile Trp Leu Glu  Gln Lys Glu Thr Ala  Lys Gln Lys
1040                 1045                 1050 gag gat  aat aaa gtc act aca  gac tat cac tat gaa  tta aaa ttg        3204
Glu Asp  Asn Lys Val Thr Thr  Asp Tyr His Tyr Glu  Leu Lys Leu
1055                 1060                 1065 gct cat  att cgt tat gat ggt  acc tgg aat gtg cca  atc acc ttt        3249
Ala His  Ile Arg Tyr Asp Gly  Thr Trp Asn Val Pro  Ile Thr Phe
1070                 1075                 1080 gat gta  gat gaa aaa ata cta  gct tta gaa ctg aca  aaa tct caa        3294
Asp Val  Asp Glu Lys Ile Leu  Ala Leu Glu Leu Thr  Lys Ser Gln
1085                 1090                 1095 gca cct  gga ctc tat tgc gca  ggt tat caa ggg gaa  gat aca cta        3339
```

```
Ala Pro Gly Leu Tyr Cys Ala Gly Tyr Gln Gly Glu Asp Thr Leu
    1100            1105            1110 tta atc atg ttt tat aga aaa aaa gag aaa ttg gat gat tat aaa       3384
Leu Ile Met Phe Tyr Arg Lys Lys Glu Lys Leu Asp Asp Tyr Lys
    1115            1120            1125 act gca cca atg caa gga ttt tat att ttc tcc gat atg tct tcc       3429
Thr Ala Pro Met Gln Gly Phe Tyr Ile Phe Ser Asp Met Ser Ser
    1130            1135            1140 aaa gat atg acc aat gaa caa tgc aat tct tat cga gat aac ggt       3474
Lys Asp Met Thr Asn Glu Gln Cys Asn Ser Tyr Arg Asp Asn Gly
    1145            1150            1155 tat aca cat ttc gat act aat tct gat act aat agc gtc ata aga       3519
Tyr Thr His Phe Asp Thr Asn Ser Asp Thr Asn Ser Val Ile Arg
    1160            1165            1170 ata aat aat cgc tat gca gag gat tat gaa att cct tca ttg atc       3564
Ile Asn Asn Arg Tyr Ala Glu Asp Tyr Glu Ile Pro Ser Leu Ile
    1175            1180            1185 aat cat agc aat agc cat gat tgg ggg gaa tat aat ctt agc cag       3609
Asn His Ser Asn Ser His Asp Trp Gly Glu Tyr Asn Leu Ser Gln
    1190            1195            1200 gta tat ggc gga aat ata gtt atc aat tac aaa gtt aca tca aat       3654
Val Tyr Gly Gly Asn Ile Val Ile Asn Tyr Lys Val Thr Ser Asn
    1205            1210            1215 gat ttg aaa atc tat att tca cca aaa tta aga ata atc cat gat       3699
Asp Leu Lys Ile Tyr Ile Ser Pro Lys Leu Arg Ile Ile His Asp
    1220            1225            1230 gga aaa gaa ggt cga gag cgc att cag tct aat cta ata aag aaa       3744
Gly Lys Glu Gly Arg Glu Arg Ile Gln Ser Asn Leu Ile Lys Lys
    1235            1240            1245 tac ggc aaa ttg ggt gat aaa ttc att att tat act agt ttg gga       3789
Tyr Gly Lys Leu Gly Asp Lys Phe Ile Ile Tyr Thr Ser Leu Gly
    1250            1255            1260 atc aat ccg aat aat tca tca aat aga ttc atg ttt tac cca gtc       3834
Ile Asn Pro Asn Asn Ser Ser Asn Arg Phe Met Phe Tyr Pro Val
    1265            1270            1275 tat caa tat aat gga aac act agc ggc ctt gct caa ggg aga cta       3879
Tyr Gln Tyr Asn Gly Asn Thr Ser Gly Leu Ala Gln Gly Arg Leu
    1280            1285            1290 tta ttc cat cga gac acg agt tat tca tct aaa gta gcg gct tgg       3924
Leu Phe His Arg Asp Thr Ser Tyr Ser Ser Lys Val Ala Ala Trp
    1295            1300            1305 att cct ggg gca gga cgt tct tta atc aat gaa aat gct aac atc       3969
Ile Pro Gly Ala Gly Arg Ser Leu Ile Asn Glu Asn Ala Asn Ile
    1310            1315            1320 ggt gat gat tgt gct gaa gat tct gtg aat aaa ccg gat gat ctt       4014
Gly Asp Asp Cys Ala Glu Asp Ser Val Asn Lys Pro Asp Asp Leu
    1325            1330            1335 aag caa tac atc tat atg act gac agt aaa ggg act gct act gat       4059
Lys Gln Tyr Ile Tyr Met Thr Asp Ser Lys Gly Thr Ala Thr Asp
    1340            1345            1350 gtt tcc ggg cca gta gat atc aac aca gca att tct tct gaa aag       4104
Val Ser Gly Pro Val Asp Ile Asn Thr Ala Ile Ser Ser Glu Lys
    1355            1360            1365 gtt caa atc aca att aaa gct ggc aaa gaa tac tct ctt aca gcg       4149
Val Gln Ile Thr Ile Lys Ala Gly Lys Glu Tyr Ser Leu Thr Ala
    1370            1375            1380 aat aaa gat gtc tcc gtt cag cca tca cct agc ttt gaa gaa atg       4194
Asn Lys Asp Val Ser Val Gln Pro Ser Pro Ser Phe Glu Glu Met
    1385            1390            1395
```

-continued

| | | | | | | | | | | | |
|---|---|---|---|---|---|---|---|---|---|---|---|
| tgt | tac | caa | ttt | aat | gct | ctc | gaa | ata | gat | ggc | tct | aat | ctg | aat | 4239 |
| Cys | Tyr | Gln | Phe | Asn | Ala | Leu | Glu | Ile | Asp | Gly | Ser | Asn | Leu | Asn | |
| | 1400 | | | | 1405 | | | | | 1410 | | | | | |
| ttt | act | aac | aat | tca | gcc | agt | att | gat | gtc | act | ttt | acc | gca | ctg | 4284 |
| Phe | Thr | Asn | Asn | Ser | Ala | Ser | Ile | Asp | Val | Thr | Phe | Thr | Ala | Leu | |
| 1415 | | | | | 1420 | | | | | 1425 | | | | | |
| gca | gat | gat | gga | cgc | aaa | ttg | ggt | tat | gaa | att | ttc | aat | atc | cct | 4329 |
| Ala | Asp | Asp | Gly | Arg | Lys | Leu | Gly | Tyr | Glu | Ile | Phe | Asn | Ile | Pro | |
| 1430 | | | | | 1435 | | | | | 1440 | | | | | |
| gtt | att | caa | aag | gtt | aaa | acc | gat | aat | gct | cta | act | ctt | ttt | cat | 4374 |
| Val | Ile | Gln | Lys | Val | Lys | Thr | Asp | Asn | Ala | Leu | Thr | Leu | Phe | His | |
| 1445 | | | | | 1450 | | | | | 1455 | | | | | |
| gac | gag | aat | ggc | gct | caa | tat | atg | caa | tgg | gga | gcc | tat | cgc | att | 4419 |
| Asp | Glu | Asn | Gly | Ala | Gln | Tyr | Met | Gln | Trp | Gly | Ala | Tyr | Arg | Ile | |
| 1460 | | | | | 1465 | | | | | 1470 | | | | | |
| cgc | ctt | aat | acg | cta | ttt | gct | cgc | caa | tta | gtt | gaa | cga | gct | aat | 4464 |
| Arg | Leu | Asn | Thr | Leu | Phe | Ala | Arg | Gln | Leu | Val | Glu | Arg | Ala | Asn | |
| 1475 | | | | | 1480 | | | | | 1485 | | | | | |
| act | ggt | att | gat | aca | att | cta | agt | atg | gaa | act | cag | aat | att | cag | 4509 |
| Thr | Gly | Ile | Asp | Thr | Ile | Leu | Ser | Met | Glu | Thr | Gln | Asn | Ile | Gln | |
| | 1490 | | | | 1495 | | | | | 1500 | | | | | |
| gaa | ccg | atg | atg | gga | ata | ggc | gct | tat | ata | gaa | ctc | att | ttg | gat | 4554 |
| Glu | Pro | Met | Met | Gly | Ile | Gly | Ala | Tyr | Ile | Glu | Leu | Ile | Leu | Asp | |
| 1505 | | | | | 1510 | | | | | 1515 | | | | | |
| aaa | tat | aat | cct | gat | atc | cac | ggc | act | aat | aaa | tca | ttt | aag | att | 4599 |
| Lys | Tyr | Asn | Pro | Asp | Ile | His | Gly | Thr | Asn | Lys | Ser | Phe | Lys | Ile | |
| 1520 | | | | | 1525 | | | | | 1530 | | | | | |
| ata | tat | ggt | gat | att | ttt | aaa | gca | ggt | gat | cat | ttt | cct | att | tat | 4644 |
| Ile | Tyr | Gly | Asp | Ile | Phe | Lys | Ala | Gly | Asp | His | Phe | Pro | Ile | Tyr | |
| 1535 | | | | | 1540 | | | | | 1545 | | | | | |
| cag | gga | gca | tta | agc | gat | att | aca | caa | aca | aca | gta | aaa | tta | ttc | 4689 |
| Gln | Gly | Ala | Leu | Ser | Asp | Ile | Thr | Gln | Thr | Thr | Val | Lys | Leu | Phe | |
| 1550 | | | | | 1555 | | | | | 1560 | | | | | |
| tta | cct | cgc | gtt | gat | aac | gct | tat | gga | aat | aaa | aac | aat | ctc | tat | 4734 |
| Leu | Pro | Arg | Val | Asp | Asn | Ala | Tyr | Gly | Asn | Lys | Asn | Asn | Leu | Tyr | |
| 1565 | | | | | 1570 | | | | | 1575 | | | | | |
| gtt | tac | gcg | gcc | tat | caa | aaa | gtg | gaa | aca | aat | ttc | att | cga | ttc | 4779 |
| Val | Tyr | Ala | Ala | Tyr | Gln | Lys | Val | Glu | Thr | Asn | Phe | Ile | Arg | Phe | |
| 1580 | | | | | 1585 | | | | | 1590 | | | | | |
| gtt | aaa | gag | gat | aat | aat | aaa | ccc | gct | aca | ttc | gac | act | acc | tat | 4824 |
| Val | Lys | Glu | Asp | Asn | Asn | Lys | Pro | Ala | Thr | Phe | Asp | Thr | Thr | Tyr | |
| 1595 | | | | | 1600 | | | | | 1605 | | | | | |
| aag | aat | ggg | acc | ttc | cca | ggg | ctt | gca | tca | gcc | aga | gta | ata | caa | 4869 |
| Lys | Asn | Gly | Thr | Phe | Pro | Gly | Leu | Ala | Ser | Ala | Arg | Val | Ile | Gln | |
| 1610 | | | | | 1615 | | | | | 1620 | | | | | |
| act | gtc | tcg | gaa | cca | atg | gat | ttc | agc | ggc | gct | aat | agt | ctc | tac | 4914 |
| Thr | Val | Ser | Glu | Pro | Met | Asp | Phe | Ser | Gly | Ala | Asn | Ser | Leu | Tyr | |
| 1625 | | | | | 1630 | | | | | 1635 | | | | | |
| ttc | tgg | gaa | ctg | ttc | tac | tat | acc | ccg | atg | atg | gtt | gct | caa | cgt | 4959 |
| Phe | Trp | Glu | Leu | Phe | Tyr | Tyr | Thr | Pro | Met | Met | Val | Ala | Gln | Arg | |
| 1640 | | | | | 1645 | | | | | 1650 | | | | | |
| ttg | cta | cat | gaa | caa | aac | ttt | gat | gaa | gcc | aac | cgt | tgg | cta | aaa | 5004 |
| Leu | Leu | His | Glu | Gln | Asn | Phe | Asp | Glu | Ala | Asn | Arg | Trp | Leu | Lys | |
| 1655 | | | | | 1660 | | | | | 1665 | | | | | |
| tat | gtc | tgg | agc | cca | tcc | ggt | tat | att | gtt | cga | ggt | caa | att | aaa | 5049 |
| Tyr | Val | Trp | Ser | Pro | Ser | Gly | Tyr | Ile | Val | Arg | Gly | Gln | Ile | Lys | |
| 1670 | | | | | 1675 | | | | | 1680 | | | | | |
| aac | tac | cac | tgg | aat | gtg | cgc | cca | tta | ctg | gaa | aac | acc | agt | tgg | 5094 |
| Asn | Tyr | His | Trp | Asn | Val | Arg | Pro | Leu | Leu | Glu | Asn | Thr | Ser | Trp | |
| 1685 | | | | | 1690 | | | | | 1695 | | | | | |

-continued

| | |
|---|---|
| aac agt gat cct ttg gat tcc gtc gat cct gac gca gtg gca cag<br>Asn Ser Asp Pro Leu Asp Ser Val Asp Pro Asp Ala Val Ala Gln<br>1700                       1705                      1710 | 5139 |
| cac gat cca atg cac tat aaa gta gcc acc ttt atg cgt act ctc<br>His Asp Pro Met His Tyr Lys Val Ala Thr Phe Met Arg Thr Leu<br>1715                       1720                      1725 | 5184 |
| gat cta ctg atg gca cgc ggc gat cac gcc tat cgc caa ctt gag<br>Asp Leu Leu Met Ala Arg Gly Asp His Ala Tyr Arg Gln Leu Glu<br>1730                       1735                      1740 | 5229 |
| cgg gat acg ctg aac gaa gcc aaa atg tgg tat atg caa gca ctg<br>Arg Asp Thr Leu Asn Glu Ala Lys Met Trp Tyr Met Gln Ala Leu<br>1745                       1750                      1755 | 5274 |
| cac ctg ttg ggc aat aaa ccc tat ctg cct ctg agt tct gta tgg<br>His Leu Leu Gly Asn Lys Pro Tyr Leu Pro Leu Ser Ser Val Trp<br>1760                       1765                      1770 | 5319 |
| aat gat cca cgt ctg gac aat gcc gca gcc act acc aca caa aaa<br>Asn Asp Pro Arg Leu Asp Asn Ala Ala Ala Thr Thr Thr Gln Lys<br>1775                       1780                      1785 | 5364 |
| gca cac gcc tac gca ata acc tct cta cgg caa ggc acg caa aca<br>Ala His Ala Tyr Ala Ile Thr Ser Leu Arg Gln Gly Thr Gln Thr<br>1790                       1795                      1800 | 5409 |
| cca gca tta tta ttg cgc tcc gct aat acc ctg acc gat ctt ttc<br>Pro Ala Leu Leu Leu Arg Ser Ala Asn Thr Leu Thr Asp Leu Phe<br>1805                       1810                      1815 | 5454 |
| ctg cca caa atc aac gac gtt atg ttg agc tac tgg aac aaa ctg<br>Leu Pro Gln Ile Asn Asp Val Met Leu Ser Tyr Trp Asn Lys Leu<br>1820                       1825                      1830 | 5499 |
| gaa ctg cgt ctg tat aac tta cgt cat aat ctc tct atc gat ggt<br>Glu Leu Arg Leu Tyr Asn Leu Arg His Asn Leu Ser Ile Asp Gly<br>1835                       1840                      1845 | 5544 |
| cag cct ctc cac cta ccg att tac gcc aca ccg gcc gat ccg aaa<br>Gln Pro Leu His Leu Pro Ile Tyr Ala Thr Pro Ala Asp Pro Lys<br>1850                       1855                      1860 | 5589 |
| gcg tta ctc agc gcc gcc gtt gct act tct caa ggc ggc ggc aaa<br>Ala Leu Leu Ser Ala Ala Val Ala Thr Ser Gln Gly Gly Gly Lys<br>1865                       1870                      1875 | 5634 |
| cta cca gag tca ttt ata tca ctg tgg cgc ttc ccg cat atg ttg<br>Leu Pro Glu Ser Phe Ile Ser Leu Trp Arg Phe Pro His Met Leu<br>1880                       1885                      1890 | 5679 |
| gaa aat gcc cgt agt atg gtc act cag cta ata cag ttc ggc tcc<br>Glu Asn Ala Arg Ser Met Val Thr Gln Leu Ile Gln Phe Gly Ser<br>1895                       1900                      1905 | 5724 |
| acg ttg caa aat att att gaa cgc caa gat gct gaa tcc tta aat<br>Thr Leu Gln Asn Ile Ile Glu Arg Gln Asp Ala Glu Ser Leu Asn<br>1910                       1915                      1920 | 5769 |
| gct ctg ctg caa aat caa gcc aaa gag ttg att ttg aca acg ctc<br>Ala Leu Leu Gln Asn Gln Ala Lys Glu Leu Ile Leu Thr Thr Leu<br>1925                       1930                      1935 | 5814 |
| agc att caa gac aaa acc atc gaa gaa ata gat gct gaa aaa act<br>Ser Ile Gln Asp Lys Thr Ile Glu Glu Ile Asp Ala Glu Lys Thr<br>1940                       1945                      1950 | 5859 |
| gtg ctg gaa aaa tcc aaa gcc gga gca aaa tcg cgc ttt gac aac<br>Val Leu Glu Lys Ser Lys Ala Gly Ala Lys Ser Arg Phe Asp Asn<br>1955                       1960                      1965 | 5904 |
| tac agc aaa tta tat gac gaa gat gtc aac gcc ggt gag cgt caa<br>Tyr Ser Lys Leu Tyr Asp Glu Asp Val Asn Ala Gly Glu Arg Gln<br>1970                       1975                      1980 | 5949 |
| gct ctg gat atg cga ata gct tcc caa agt att acc tca gga ttg<br>Ala Leu Asp Met Arg Ile Ala Ser Gln Ser Ile Thr Ser Gly Leu | 5994 |

|  |  |  |  |  |  |  |  |  |  |  |  |  |
|---|---|---|---|---|---|---|---|---|---|---|---|---|
| | 1985 | | | | 1990 | | | | 1995 | | | |
| aaa | ggc | ttg | cac | atg | gct | gcc | gcc | gca | ctg | gag | atg | gtg | ccc | aat | 6039 |
| Lys | Gly | Leu | His | Met | Ala | Ala | Ala | Ala | Leu | Glu | Met | Val | Pro | Asn | |
| | 2000 | | | | 2005 | | | | 2010 | | | | | | |
| atc | tac | ggc | ttt | gca | gtc | ggg | ggg | acg | cgc | tat | gga | gca | att | gcc | 6084 |
| Ile | Tyr | Gly | Phe | Ala | Val | Gly | Gly | Thr | Arg | Tyr | Gly | Ala | Ile | Ala | |
| | 2015 | | | | 2020 | | | | 2025 | | | | | | |
| aat | gcc | att | gcg | att | ggt | ggc | ggt | atc | gcc | gca | gaa | ggt | ttg | tta | 6129 |
| Asn | Ala | Ile | Ala | Ile | Gly | Gly | Gly | Ile | Ala | Ala | Glu | Gly | Leu | Leu | |
| | 2030 | | | | 2035 | | | | 2040 | | | | | | |
| att | gaa | gca | gag | aaa | gtc | tcg | caa | tct | gaa | ata | tgg | cgc | cgt | cgc | 6174 |
| Ile | Glu | Ala | Glu | Lys | Val | Ser | Gln | Ser | Glu | Ile | Trp | Arg | Arg | Arg | |
| | 2045 | | | | 2050 | | | | 2055 | | | | | | |
| cgt | caa | gag | tgg | gaa | atc | cag | cgt | aat | aat | gcc | gaa | gca | gag | atg | 6219 |
| Arg | Gln | Glu | Trp | Glu | Ile | Gln | Arg | Asn | Asn | Ala | Glu | Ala | Glu | Met | |
| | 2060 | | | | 2065 | | | | 2070 | | | | | | |
| aaa | caa | atc | gat | gct | caa | ctt | aaa | tca | cta | acg | gta | cgc | cgt | gaa | 6264 |
| Lys | Gln | Ile | Asp | Ala | Gln | Leu | Lys | Ser | Leu | Thr | Val | Arg | Arg | Glu | |
| | 2075 | | | | 2080 | | | | 2085 | | | | | | |
| gcg | gcg | gta | tta | cag | aaa | acc | ggc | cta | aaa | acc | caa | cag | gaa | caa | 6309 |
| Ala | Ala | Val | Leu | Gln | Lys | Thr | Gly | Leu | Lys | Thr | Gln | Gln | Glu | Gln | |
| | 2090 | | | | 2095 | | | | 2100 | | | | | | |
| act | caa | gcg | caa | cta | gct | ttc | ctg | caa | cga | aaa | ttc | agc | aat | caa | 6354 |
| Thr | Gln | Ala | Gln | Leu | Ala | Phe | Leu | Gln | Arg | Lys | Phe | Ser | Asn | Gln | |
| | 2105 | | | | 2110 | | | | 2115 | | | | | | |
| gcg | ctg | tat | aat | tgg | tta | cgt | ggt | cgg | tta | gca | gcc | att | tat | ttc | 6399 |
| Ala | Leu | Tyr | Asn | Trp | Leu | Arg | Gly | Arg | Leu | Ala | Ala | Ile | Tyr | Phe | |
| | 2120 | | | | 2125 | | | | 2130 | | | | | | |
| caa | ttt | tac | gat | tta | gtc | gtc | gcc | cgt | tgt | ttg | atg | gca | gaa | caa | 6444 |
| Gln | Phe | Tyr | Asp | Leu | Val | Val | Ala | Arg | Cys | Leu | Met | Ala | Glu | Gln | |
| | 2135 | | | | 2140 | | | | 2145 | | | | | | |
| gct | tac | cgt | tgg | gaa | act | aat | gat | agc | tct | gca | cgc | ttt | att | aaa | 6489 |
| Ala | Tyr | Arg | Trp | Glu | Thr | Asn | Asp | Ser | Ser | Ala | Arg | Phe | Ile | Lys | |
| | 2150 | | | | 2155 | | | | 2160 | | | | | | |
| ccg | gga | gcc | tgg | cag | gga | acc | tat | gcc | ggc | ctg | ctc | gcc | gga | gaa | 6534 |
| Pro | Gly | Ala | Trp | Gln | Gly | Thr | Tyr | Ala | Gly | Leu | Leu | Ala | Gly | Glu | |
| | 2165 | | | | 2170 | | | | 2175 | | | | | | |
| acc | cta | atg | ttg | aac | ctg | gcg | caa | atg | gaa | gac | gcg | cac | ctg | aaa | 6579 |
| Thr | Leu | Met | Leu | Asn | Leu | Ala | Gln | Met | Glu | Asp | Ala | His | Leu | Lys | |
| | 2180 | | | | 2185 | | | | 2190 | | | | | | |
| caa | gag | caa | cgc | gca | ctg | gaa | gtg | gaa | cgc | acg | gtt | tct | ctg | gcg | 6624 |
| Gln | Glu | Gln | Arg | Ala | Leu | Glu | Val | Glu | Arg | Thr | Val | Ser | Leu | Ala | |
| | 2195 | | | | 2200 | | | | 2205 | | | | | | |
| cag | gtg | tac | caa | tcc | tta | ggg | gag | aaa | agc | ttt | gca | tta | aaa | gat | 6669 |
| Gln | Val | Tyr | Gln | Ser | Leu | Gly | Glu | Lys | Ser | Phe | Ala | Leu | Lys | Asp | |
| | 2210 | | | | 2215 | | | | 2220 | | | | | | |
| aaa | att | gaa | gcg | ttg | cta | caa | gga | gat | aaa | gag | act | tcc | gcc | ggt | 6714 |
| Lys | Ile | Glu | Ala | Leu | Leu | Gln | Gly | Asp | Lys | Glu | Thr | Ser | Ala | Gly | |
| | 2225 | | | | 2230 | | | | 2235 | | | | | | |
| aac | gac | ggc | aat | caa | ttg | aaa | tta | acc | aac | aat | acg | cta | tcc | gcg | 6759 |
| Asn | Asp | Gly | Asn | Gln | Leu | Lys | Leu | Thr | Asn | Asn | Thr | Leu | Ser | Ala | |
| | 2240 | | | | 2245 | | | | 2250 | | | | | | |
| acg | cta | acc | ctg | caa | gat | ctg | aaa | ctc | aaa | gat | gac | tac | ccg | gaa | 6804 |
| Thr | Leu | Thr | Leu | Gln | Asp | Leu | Lys | Leu | Lys | Asp | Asp | Tyr | Pro | Glu | |
| | 2255 | | | | 2260 | | | | 2265 | | | | | | |
| gag | atg | cag | tta | ggt | aaa | aca | cgc | cgc | att | aaa | caa | att | agc | gtc | 6849 |
| Glu | Met | Gln | Leu | Gly | Lys | Thr | Arg | Arg | Ile | Lys | Gln | Ile | Ser | Val | |
| | 2270 | | | | 2275 | | | | 2280 | | | | | | |
| tcc | tta | ccg | gca | tta | ttg | gga | ccg | tat | caa | gat | gtt | cag | gct | gtc | 6894 |

-continued

```
Ser Leu Pro Ala Leu Leu Gly Pro Tyr Gln Asp Val Gln Ala Val
    2285                2290                2295 ctg tct tat ggt ggc gat gcc acc ggg cta gct aaa ggt tgt aaa      6939
Leu Ser Tyr Gly Gly Asp Ala Thr Gly Leu Ala Lys Gly Cys Lys
    2300                2305                2310 gcc ttg gcg gtc tcc cac ggc ctg aat gac aac ggt cag ttt cag      6984
Ala Leu Ala Val Ser His Gly Leu Asn Asp Asn Gly Gln Phe Gln
    2315                2320                2325 ctc gat ttt aac gat ggc aaa ttc ctg ccg ttt gaa ggg atc gat      7029
Leu Asp Phe Asn Asp Gly Lys Phe Leu Pro Phe Glu Gly Ile Asp
    2330                2335                2340 att aat gac aaa ggg aca ttc acg cta agt ttc ccc aat gcc gcc      7074
Ile Asn Asp Lys Gly Thr Phe Thr Leu Ser Phe Pro Asn Ala Ala
    2345                2350                2355 agt aaa caa aaa aat ata tta cag atg ctg acc gat att att ctg      7119
Ser Lys Gln Lys Asn Ile Leu Gln Met Leu Thr Asp Ile Ile Leu
    2360                2365                2370 cac att cgt tac act att ctc gaa taa                               7146
His Ile Arg Tyr Thr Ile Leu Glu
    2375                2380
```

<210> SEQ ID NO 8
<211> LENGTH: 2381
<212> TYPE: PRT
<213> ORGANISM: Photorhabdus luminescens

<400> SEQUENCE: 8

```
Met Asn Ser Tyr Val Lys Glu Ile Pro Asp Val Leu Gln Ser Gln Tyr
1               5                   10                  15

Gly Ile Asn Cys Leu Thr Asp Ile Cys His Tyr Ser Phe Asn Glu Phe
            20                  25                  30

Arg Gln Gln Val Ser Asp His Leu Ser Trp Ser Glu Thr Asn Arg Leu
        35                  40                  45

Tyr Arg Asp Ala Gln Gln Glu Gln Lys Glu Asn Gln Leu Tyr Glu Ala
    50                  55                  60

Arg Ile Leu Lys Arg Ala Asn Pro Gln Leu Gln Asn Ala Val His Leu
65                  70                  75                  80

Gly Ile Thr Leu Pro His Ala Glu Leu Arg Gly Tyr Asn Ser Glu Phe
                85                  90                  95

Gly Gly Arg Ala Ser Gln Tyr Val Ala Pro Gly Ser Val Ser Ser Met
            100                 105                 110

Phe Ser Pro Ala Ala Tyr Leu Thr Glu Leu Tyr Arg Glu Ala Arg Asn
        115                 120                 125

Leu His Ala Ser Asp Ser Val Tyr His Leu Asp Glu Arg Arg Pro Asp
    130                 135                 140

Leu Gln Ser Met Thr Leu Ser Gln Gln Asn Met Asp Thr Glu Leu Ser
145                 150                 155                 160

Thr Leu Ser Leu Ser Asn Glu Ile Leu Lys Gly Ile Lys Ala Asn
                165                 170                 175

Gln Ser Asn Leu Asp Ser Asp Thr Lys Val Met Glu Met Leu Ser Thr
            180                 185                 190

Phe Arg Pro Ser Gly Thr Ile Pro Tyr His Asp Ala Tyr Glu Asn Val
        195                 200                 205

Arg Lys Ala Ile Gln Leu Gln Asp Pro Lys Leu Glu Gln Phe Gln Lys
    210                 215                 220

Ser Pro Ala Val Ala Gly Leu Met His Gln Ala Ser Leu Leu Gly Ile
225                 230                 235                 240
```

-continued

```
Asn Asn Ser Ile Ser Pro Glu Leu Phe Asn Ile Leu Thr Glu Ile
            245                 250                 255

Thr Glu Ala Asn Ala Glu Ala Ile Tyr Lys Gln Asn Phe Gly Asp Ile
            260                 265                 270

Asp Pro Ala Cys Leu Ala Met Pro Glu Tyr Leu Lys Ser Tyr Tyr Asn
            275                 280                 285

Phe Ser Asp Glu Glu Leu Ser Gln Phe Ile Arg Lys Tyr Pro Asp Asn
            290                 295                 300

Glu Leu Asn Thr Gln Lys Ile His Leu Leu Lys Ile Asn Lys Ile Ile
305                 310                 315                 320

Leu Leu Ser Gln Ala Val Asn Leu Pro Phe Leu Lys Leu Asp Glu Ile
                325                 330                 335

Ile Pro Glu Gln Asn Ile Thr Pro Thr Val Leu Gly Lys Ile Phe Leu
                340                 345                 350

Val Lys Tyr Tyr Met Gln Lys Tyr Asn Ile Gly Thr Glu Thr Ala Leu
            355                 360                 365

Ile Leu Cys Asn Asp Ser Ile Ser Gln Tyr Ser Tyr Ser Asn Gln Pro
370                 375                 380

Ser Gln Phe Asp Arg Leu Phe Asn Thr Ser Pro Leu Asn Gly Gln Tyr
385                 390                 395                 400

Phe Val Ile Glu Asp Thr Asn Ile Asp Leu Ser Leu Asn Ser Thr Asp
                405                 410                 415

Asn Trp His Lys Ala Val Leu Lys Arg Ala Phe Asn Val Asp Asp Ile
                420                 425                 430

Ser Leu Tyr Arg Leu Leu His Ile Ala Asn His Asn Asn Thr Asp Gly
            435                 440                 445

Lys Ile Ala Asn Asn Ile Lys Asn Leu Ser Asn Leu Tyr Met Thr Lys
            450                 455                 460

Leu Leu Ala Asp Ile His Gln Leu Thr Ile Asp Glu Leu Tyr Leu Leu
465                 470                 475                 480

Leu Ile Thr Ile Gly Glu Asp Lys Ile Asn Leu Tyr Asp Ile Asp Asp
                485                 490                 495

Lys Glu Leu Glu Lys Leu Ile Asn Arg Leu Asp Thr Leu Ser Asn Trp
            500                 505                 510

Leu His Thr Gln Lys Trp Ser Ile Tyr Gln Leu Phe Leu Met Thr Thr
            515                 520                 525

Thr Asn Tyr Asp Lys Thr Leu Thr Pro Glu Ile Gln Asn Leu Leu Asp
            530                 535                 540

Thr Val Tyr Asn Gly Leu Gln Asn Phe Asp Lys Asn Lys Thr Lys Leu
545                 550                 555                 560

Leu Ala Ala Ile Ala Pro Tyr Ile Ala Ala Thr Leu Gln Leu Pro Ser
                565                 570                 575

Glu Asn Val Ala His Ser Ile Leu Leu Trp Ala Asp Lys Ile Lys Pro
            580                 585                 590

Ser Glu Asn Lys Ile Thr Ala Glu Lys Phe Trp Ile Trp Leu Gln Asn
            595                 600                 605

Arg Asp Thr Thr Glu Leu Ser Lys Pro Pro Glu Met Gln Glu Gln Ile
            610                 615                 620

Ile Gln Tyr Cys His Cys Leu Ala Gln Leu Thr Met Ile Tyr Arg Ser
625                 630                 635                 640

Ser Gly Ile Asn Glu Asn Ala Phe Arg Leu Phe Ile Glu Lys Pro Thr
                645                 650                 655
```

-continued

```
Ile Phe Gly Ile Pro Asp Glu Pro Asn Lys Ala Thr Pro Ala His Asn
            660                 665                 670

Ala Pro Thr Leu Ile Ile Leu Thr Arg Phe Ala Asn Trp Val Asn Ser
        675                 680                 685

Leu Gly Glu Lys Ala Ser Pro Ile Leu Thr Ala Phe Glu Asn Lys Thr
    690                 695                 700

Leu Thr Ala Glu Lys Leu Ala Asn Ala Met Asn Leu Asp Ala Asn Leu
705                 710                 715                 720

Leu Glu Gln Ala Ser Ile Gln Ala Gln Asn Tyr Lys Gln Val Thr Lys
                725                 730                 735

Glu Asn Thr Phe Ser Asn Trp Gln Ser Ile Asp Ile Leu Gln Trp
            740                 745                 750

Thr Asn Ile Ala Ser Asn Leu Asn Ile Ser Pro Gln Gly Ile Ser Pro
        755                 760                 765

Leu Ile Ala Leu Asp Tyr Ile Lys Pro Ala Gln Lys Thr Pro Thr Tyr
    770                 775                 780

Ala Gln Trp Glu Asn Ala Ala Ile Ala Leu Thr Ala Gly Leu Asp Thr
785                 790                 795                 800

Gln Gln Thr His Thr Leu His Val Phe Leu Asp Glu Ser Arg Ser Thr
                805                 810                 815

Ala Leu Ser Asn Tyr Tyr Ile Gly Lys Val Ala Asn Arg Ala Ala Ser
            820                 825                 830

Ile Lys Ser Arg Asp Asp Leu Tyr Gln Tyr Leu Leu Ile Asp Asn Gln
        835                 840                 845

Val Ser Ala Glu Ile Lys Thr Thr Arg Ile Ala Glu Ala Ile Ala Ser
    850                 855                 860

Ile Gln Leu Tyr Val Asn Arg Ala Leu Glu Asn Ile Glu Ile His Ala
865                 870                 875                 880

Val Ser Asp Val Ile Thr Arg Gln Phe Phe Ile Asp Trp Asp Lys Tyr
                885                 890                 895

Asn Lys Arg Tyr Ser Thr Trp Ala Gly Val Ser Gln Leu Val Tyr Tyr
            900                 905                 910

Pro Glu Asn Tyr Ile Asp Pro Thr Met Arg Ile Gly Gln Thr Lys Met
        915                 920                 925

Met Asp Thr Leu Leu Gln Ser Val Ser Gln Ser Gln Leu Asn Ala Asp
    930                 935                 940

Thr Val Glu Asp Ala Phe Lys Ser Tyr Leu Thr Ser Phe Glu Gln Val
945                 950                 955                 960

Ala Asn Leu Glu Val Ile Ser Ala Tyr His Asp Asn Val Asn Asn Asp
                965                 970                 975

Gln Gly Leu Thr Tyr Phe Ile Gly Asn Ser Lys Thr Gly Val Asn Gln
            980                 985                 990

Tyr Tyr Trp Arg Ser Val Asp His Ser Lys Phe Asn Asp Gly Lys Phe
        995                 1000                1005

Ala Ala Asn Ala Trp Ser Glu Trp His Lys Ile Asp Cys Ala Ile
    1010                1015                1020

Asn Pro Tyr Gln Ser Thr Ile Arg Pro Val Ile Tyr Lys Ser Arg
    1025                1030                1035

Leu Tyr Leu Ile Trp Leu Glu Gln Lys Glu Thr Ala Lys Gln Lys
    1040                1045                1050

Glu Asp Asn Lys Val Thr Asp Tyr His Tyr Glu Leu Lys Leu
    1055                1060                1065

Ala His Ile Arg Tyr Asp Gly Thr Trp Asn Val Pro Ile Thr Phe
```

-continued

```
            1070                1075                1080
Asp Val Asp Glu Lys Ile Leu Ala Leu Glu Leu Thr Lys Ser Gln
        1085                1090                1095

Ala Pro Gly Leu Tyr Cys Ala Gly Tyr Gln Gly Glu Asp Thr Leu
        1100                1105                1110

Leu Ile Met Phe Tyr Arg Lys Lys Glu Lys Leu Asp Asp Tyr Lys
        1115                1120                1125

Thr Ala Pro Met Gln Gly Phe Tyr Ile Phe Ser Asp Met Ser Ser
        1130                1135                1140

Lys Asp Met Thr Asn Glu Gln Cys Asn Ser Tyr Arg Asp Asn Gly
        1145                1150                1155

Tyr Thr His Phe Asp Thr Asn Ser Asp Thr Asn Ser Val Ile Arg
        1160                1165                1170

Ile Asn Asn Arg Tyr Ala Glu Asp Tyr Glu Ile Pro Ser Leu Ile
        1175                1180                1185

Asn His Ser Asn Ser His Asp Trp Gly Tyr Asn Leu Ser Gln
        1190                1195                1200

Val Tyr Gly Gly Asn Ile Val Ile Asn Tyr Lys Val Thr Ser Asn
        1205                1210                1215

Asp Leu Lys Ile Tyr Ile Ser Pro Lys Leu Arg Ile Ile His Asp
        1220                1225                1230

Gly Lys Glu Gly Arg Glu Arg Ile Gln Ser Asn Leu Ile Lys Lys
        1235                1240                1245

Tyr Gly Lys Leu Gly Asp Lys Phe Ile Ile Tyr Thr Ser Leu Gly
        1250                1255                1260

Ile Asn Pro Asn Asn Ser Ser Asn Arg Phe Met Phe Tyr Pro Val
        1265                1270                1275

Tyr Gln Tyr Asn Gly Asn Thr Ser Gly Leu Ala Gln Gly Arg Leu
        1280                1285                1290

Leu Phe His Arg Asp Thr Ser Tyr Ser Ser Lys Val Ala Ala Trp
        1295                1300                1305

Ile Pro Gly Ala Gly Arg Ser Leu Ile Asn Glu Asn Ala Asn Ile
        1310                1315                1320

Gly Asp Asp Cys Ala Glu Asp Ser Val Asn Lys Pro Asp Asp Leu
        1325                1330                1335

Lys Gln Tyr Ile Tyr Met Thr Asp Ser Lys Gly Thr Ala Thr Asp
        1340                1345                1350

Val Ser Gly Pro Val Asp Ile Asn Thr Ala Ile Ser Ser Glu Lys
        1355                1360                1365

Val Gln Ile Thr Ile Lys Ala Gly Lys Glu Tyr Ser Leu Thr Ala
        1370                1375                1380

Asn Lys Asp Val Ser Val Gln Pro Ser Pro Ser Phe Glu Glu Met
        1385                1390                1395

Cys Tyr Gln Phe Asn Ala Leu Glu Ile Asp Gly Ser Asn Leu Asn
        1400                1405                1410

Phe Thr Asn Asn Ser Ala Ser Ile Asp Val Thr Phe Thr Ala Leu
        1415                1420                1425

Ala Asp Asp Gly Arg Lys Leu Gly Tyr Glu Ile Phe Asn Ile Pro
        1430                1435                1440

Val Ile Gln Lys Val Lys Thr Asp Asn Ala Leu Thr Leu Phe His
        1445                1450                1455

Asp Glu Asn Gly Ala Gln Tyr Met Gln Trp Gly Ala Tyr Arg Ile
        1460                1465                1470
```

-continued

Arg Leu Asn Thr Leu Phe Ala Arg Gln Leu Val Glu Arg Ala Asn
1475                1480                1485

Thr Gly Ile Asp Thr Ile Leu Ser Met Glu Thr Gln Asn Ile Gln
1490                1495                1500

Glu Pro Met Met Gly Ile Gly Ala Tyr Ile Glu Leu Ile Leu Asp
1505                1510                1515

Lys Tyr Asn Pro Asp Ile His Gly Thr Asn Lys Ser Phe Lys Ile
1520                1525                1530

Ile Tyr Gly Asp Ile Phe Lys Ala Gly Asp His Phe Pro Ile Tyr
1535                1540                1545

Gln Gly Ala Leu Ser Asp Ile Thr Gln Thr Thr Val Lys Leu Phe
1550                1555                1560

Leu Pro Arg Val Asp Asn Ala Tyr Gly Asn Lys Asn Asn Leu Tyr
1565                1570                1575

Val Tyr Ala Ala Tyr Gln Lys Val Glu Thr Asn Phe Ile Arg Phe
1580                1585                1590

Val Lys Glu Asp Asn Asn Lys Pro Ala Thr Phe Asp Thr Thr Tyr
1595                1600                1605

Lys Asn Gly Thr Phe Pro Gly Leu Ala Ser Ala Arg Val Ile Gln
1610                1615                1620

Thr Val Ser Glu Pro Met Asp Phe Ser Gly Ala Asn Ser Leu Tyr
1625                1630                1635

Phe Trp Glu Leu Phe Tyr Tyr Thr Pro Met Met Val Ala Gln Arg
1640                1645                1650

Leu Leu His Glu Gln Asn Phe Asp Glu Ala Asn Arg Trp Leu Lys
1655                1660                1665

Tyr Val Trp Ser Pro Ser Gly Tyr Ile Val Arg Gly Gln Ile Lys
1670                1675                1680

Asn Tyr His Trp Asn Val Arg Pro Leu Leu Glu Asn Thr Ser Trp
1685                1690                1695

Asn Ser Asp Pro Leu Asp Ser Val Asp Pro Asp Ala Val Ala Gln
1700                1705                1710

His Asp Pro Met His Tyr Lys Val Ala Thr Phe Met Arg Thr Leu
1715                1720                1725

Asp Leu Leu Met Ala Arg Gly Asp His Ala Tyr Arg Gln Leu Glu
1730                1735                1740

Arg Asp Thr Leu Asn Glu Ala Lys Met Trp Tyr Met Gln Ala Leu
1745                1750                1755

His Leu Leu Gly Asn Lys Pro Tyr Leu Pro Leu Ser Ser Val Trp
1760                1765                1770

Asn Asp Pro Arg Leu Asp Asn Ala Ala Ala Thr Thr Thr Gln Lys
1775                1780                1785

Ala His Ala Tyr Ala Ile Thr Ser Leu Arg Gln Gly Thr Gln Thr
1790                1795                1800

Pro Ala Leu Leu Leu Arg Ser Ala Asn Thr Leu Thr Asp Leu Phe
1805                1810                1815

Leu Pro Gln Ile Asn Asp Val Met Leu Ser Tyr Trp Asn Lys Leu
1820                1825                1830

Glu Leu Arg Leu Tyr Asn Leu Arg His Asn Leu Ser Ile Asp Gly
1835                1840                1845

Gln Pro Leu His Leu Pro Ile Tyr Ala Thr Pro Ala Asp Pro Lys
1850                1855                1860

```
Ala Leu Leu Ser Ala Ala Val Ala Thr Ser Gln Gly Gly Gly Lys
        1865            1870            1875

Leu Pro Glu Ser Phe Ile Ser Leu Trp Arg Phe Pro His Met Leu
    1880            1885            1890

Glu Asn Ala Arg Ser Met Val Thr Gln Leu Ile Gln Phe Gly Ser
    1895            1900            1905

Thr Leu Gln Asn Ile Ile Glu Arg Gln Asp Ala Glu Ser Leu Asn
    1910            1915            1920

Ala Leu Leu Gln Asn Gln Ala Lys Glu Leu Ile Leu Thr Thr Leu
1925            1930            1935

Ser Ile Gln Asp Lys Thr Ile Glu Glu Ile Asp Ala Glu Lys Thr
    1940            1945            1950

Val Leu Glu Lys Ser Lys Ala Gly Ala Lys Ser Arg Phe Asp Asn
    1955            1960            1965

Tyr Ser Lys Leu Tyr Asp Glu Asp Val Asn Ala Gly Glu Arg Gln
    1970            1975            1980

Ala Leu Asp Met Arg Ile Ala Ser Gln Ser Ile Thr Ser Gly Leu
1985            1990            1995

Lys Gly Leu His Met Ala Ala Ala Ala Leu Glu Met Val Pro Asn
    2000            2005            2010

Ile Tyr Gly Phe Ala Val Gly Gly Thr Arg Tyr Gly Ala Ile Ala
    2015            2020            2025

Asn Ala Ile Ala Ile Gly Gly Gly Ile Ala Ala Glu Gly Leu Leu
2030            2035            2040

Ile Glu Ala Glu Lys Val Ser Gln Ser Glu Ile Trp Arg Arg Arg
    2045            2050            2055

Arg Gln Glu Trp Glu Ile Gln Arg Asn Asn Ala Glu Ala Glu Met
    2060            2065            2070

Lys Gln Ile Asp Ala Gln Leu Lys Ser Leu Thr Val Arg Arg Glu
    2075            2080            2085

Ala Ala Val Leu Gln Lys Thr Gly Leu Lys Thr Gln Gln Glu Gln
2090            2095            2100

Thr Gln Ala Gln Leu Ala Phe Leu Gln Arg Lys Phe Ser Asn Gln
    2105            2110            2115

Ala Leu Tyr Asn Trp Leu Arg Gly Arg Leu Ala Ala Ile Tyr Phe
    2120            2125            2130

Gln Phe Tyr Asp Leu Val Val Ala Arg Cys Leu Met Ala Glu Gln
    2135            2140            2145

Ala Tyr Arg Trp Glu Thr Asn Asp Ser Ser Ala Arg Phe Ile Lys
    2150            2155            2160

Pro Gly Ala Trp Gln Gly Thr Tyr Ala Gly Leu Leu Ala Gly Glu
    2165            2170            2175

Thr Leu Met Leu Asn Leu Ala Gln Met Glu Asp Ala His Leu Lys
    2180            2185            2190

Gln Glu Gln Arg Ala Leu Glu Val Glu Arg Thr Val Ser Leu Ala
    2195            2200            2205

Gln Val Tyr Gln Ser Leu Gly Glu Lys Ser Phe Ala Leu Lys Asp
    2210            2215            2220

Lys Ile Glu Ala Leu Leu Gln Gly Asp Lys Glu Thr Ser Ala Gly
    2225            2230            2235

Asn Asp Gly Asn Gln Leu Lys Leu Thr Asn Asn Thr Leu Ser Ala
    2240            2245            2250

Thr Leu Thr Leu Gln Asp Leu Lys Leu Lys Asp Asp Tyr Pro Glu
```

-continued

```
                2255                    2260                    2265

Glu  Met  Gln  Leu  Gly  Lys  Thr  Arg  Arg  Ile  Lys  Gln  Ile  Ser  Val
            2270                     2275                    2280

Ser  Leu  Pro  Ala  Leu  Leu  Gly  Pro  Tyr  Gln  Asp  Val   Gln  Ala  Val
            2285                     2290                    2295

Leu  Ser  Tyr  Gly  Gly  Asp  Ala   Thr  Gly  Leu  Ala  Lys   Gly  Cys  Lys
            2300                     2305                    2310

Ala  Leu  Ala  Val  Ser  His  Gly   Leu  Asn  Asp  Asn  Gly   Gln  Phe  Gln
            2315                     2320                    2325

Leu  Asp  Phe  Asn  Asp  Gly  Lys   Phe  Leu  Pro  Phe  Glu   Gly  Ile  Asp
            2330                     2335                    2340

Ile  Asn  Asp  Lys  Gly  Thr  Phe   Thr  Leu  Ser  Phe  Pro   Asn  Ala  Ala
            2345                     2350                    2355

Ser  Lys  Gln  Lys  Asn  Ile  Leu   Gln  Met  Leu  Thr  Asp   Ile  Ile  Leu
            2360                     2365                    2370

His  Ile  Arg  Tyr  Thr  Ile  Leu   Glu
            2375                     2380

<210> SEQ ID NO 9
<211> LENGTH: 4425
<212> TYPE: DNA
<213> ORGANISM: Photorhabdus luminescens
<220> FEATURE:
<221> NAME/KEY: CDS
<222> LOCATION: (1)..(4422)

<400> SEQUENCE: 9 atg caa aat tca caa gat ttt agt att acg gaa ctg tca ctg ccc aaa       48
Met Gln Asn Ser Gln Asp Phe Ser Ile Thr Glu Leu Ser Leu Pro Lys
 1               5                  10                  15 ggg ggg ggc gct atc acg gga atg ggt gaa gca tta acc ccc act gga       96
Gly Gly Gly Ala Ile Thr Gly Met Gly Glu Ala Leu Thr Pro Thr Gly
             20                  25                  30 ccg gat ggt atg gcc gcg cta tct cta cca ttg cct att tct gcc ggg      144
Pro Asp Gly Met Ala Ala Leu Ser Leu Pro Leu Pro Ile Ser Ala Gly
         35                  40                  45 cgc ggt tat gct ccc gca ttc act ctg aat tac aac agc ggc gcc ggt      192
Arg Gly Tyr Ala Pro Ala Phe Thr Leu Asn Tyr Asn Ser Gly Ala Gly
     50                  55                  60 aac agt cca ttt ggt ctg ggt tgg gat tgc aac gtt atg act atc cgc      240
Asn Ser Pro Phe Gly Leu Gly Trp Asp Cys Asn Val Met Thr Ile Arg
 65                  70                  75                  80 cgc cgc acc cat ttt ggc gtc ccc cat tat gac gaa acc gat acc ttt      288
Arg Arg Thr His Phe Gly Val Pro His Tyr Asp Glu Thr Asp Thr Phe
                 85                  90                  95 ttg ggg cca gaa ggc gaa gtg ctg gtg gta gcg gat caa cct cgc gac      336
Leu Gly Pro Glu Gly Glu Val Leu Val Val Ala Asp Gln Pro Arg Asp
            100                 105                 110 gaa tcc aca tta cag ggt atc aat tta ggc gcc acc ttt acc gtt acc      384
Glu Ser Thr Leu Gln Gly Ile Asn Leu Gly Ala Thr Phe Thr Val Thr
        115                 120                 125 ggc tac cgt tcc cgt ctg gaa agc cat ttc agc cga ttg gaa tat tgg      432
Gly Tyr Arg Ser Arg Leu Glu Ser His Phe Ser Arg Leu Glu Tyr Trp
    130                 135                 140 caa ccc aaa aca aca ggt aaa aca gat ttt tgg ttg ata tat agc cca      480
Gln Pro Lys Thr Thr Gly Lys Thr Asp Phe Trp Leu Ile Tyr Ser Pro
145                 150                 155                 160 gat ggg cag gtg cat cta ctg ggt aaa tca ccg caa gcg cgg atc agc      528
Asp Gly Gln Val His Leu Leu Gly Lys Ser Pro Gln Ala Arg Ile Ser
```

```
                    165                 170                 175
aac cca tcc caa acg aca caa aca gca caa tgg ctg ctg gaa gcc tct          576
Asn Pro Ser Gln Thr Thr Gln Thr Ala Gln Trp Leu Leu Glu Ala Ser
            180                 185                 190 gta tca tca cgt ggc gaa caa att tat tat caa tat cgc gcc gaa gat          624
Val Ser Ser Arg Gly Glu Gln Ile Tyr Tyr Gln Tyr Arg Ala Glu Asp
            195                 200                 205 gac aca ggt tgc gaa gca gat gaa att acg cac cat tta cag gct aca          672
Asp Thr Gly Cys Glu Ala Asp Glu Ile Thr His His Leu Gln Ala Thr
210                 215                 220 gcg caa cgt tat tta cac atc gtg tat tac ggc aac cgt aca gcc agc          720
Ala Gln Arg Tyr Leu His Ile Val Tyr Tyr Gly Asn Arg Thr Ala Ser
225                 230                 235                 240 gaa aca tta ccc ggt ctg gat ggc agc gcc cca tca caa gca gac tgg          768
Glu Thr Leu Pro Gly Leu Asp Gly Ser Ala Pro Ser Gln Ala Asp Trp
                245                 250                 255 ttg ttc tat ctg gta ttt gat tac ggc gaa cgc agt aac aac ctg aaa          816
Leu Phe Tyr Leu Val Phe Asp Tyr Gly Glu Arg Ser Asn Asn Leu Lys
            260                 265                 270 acg cca cca gca ttt tcg act aca ggt agc tgg ctt tgc cgt cag gac          864
Thr Pro Pro Ala Phe Ser Thr Thr Gly Ser Trp Leu Cys Arg Gln Asp
            275                 280                 285 cgt ttt tcc cgt tat gaa tat ggc ttt gag att cgt acc cgc cgc tta          912
Arg Phe Ser Arg Tyr Glu Tyr Gly Phe Glu Ile Arg Thr Arg Arg Leu
290                 295                 300 tgc cgt cag gta ttg atg tac cat cac ctg caa gca ctg gat agt aag          960
Cys Arg Gln Val Leu Met Tyr His His Leu Gln Ala Leu Asp Ser Lys
305                 310                 315                 320 ata aca gaa cac aac gga cca acg ctg gtt tca cgc ctg ata ctc aat         1008
Ile Thr Glu His Asn Gly Pro Thr Leu Val Ser Arg Leu Ile Leu Asn
                325                 330                 335 tac gac gaa agc gcg ata gcc agc acg cta gta ttc gtt cgc cga gtg         1056
Tyr Asp Glu Ser Ala Ile Ala Ser Thr Leu Val Phe Val Arg Arg Val
            340                 345                 350 gga cac gag caa gat ggt aat gtc gtc acc ctg ccg cca tta gaa ttg         1104
Gly His Glu Gln Asp Gly Asn Val Val Thr Leu Pro Pro Leu Glu Leu
            355                 360                 365 gca tat cag gat ttt tca ccg cga cat cac gct cac tgg caa cca atg         1152
Ala Tyr Gln Asp Phe Ser Pro Arg His His Ala His Trp Gln Pro Met
370                 375                 380 gat gta ctg gca aac ttc aat gcc att cag cgc tgg cag cta gtc gat         1200
Asp Val Leu Ala Asn Phe Asn Ala Ile Gln Arg Trp Gln Leu Val Asp
385                 390                 395                 400 cta aaa ggc gaa gga tta ccc ggc ctg tta tat cag gat aaa ggc gct         1248
Leu Lys Gly Glu Gly Leu Pro Gly Leu Leu Tyr Gln Asp Lys Gly Ala
                405                 410                 415 tgg tgg tac cgc tcc gca cag cgt ctg ggc gaa att ggc tca gat gcc         1296
Trp Trp Tyr Arg Ser Ala Gln Arg Leu Gly Glu Ile Gly Ser Asp Ala
            420                 425                 430 gtc act tgg gaa aag atg caa cct tta tcg gtt att cct tct ttg caa         1344
Val Thr Trp Glu Lys Met Gln Pro Leu Ser Val Ile Pro Ser Leu Gln
            435                 440                 445 agt aat gcc tcg ttg gtg gat atc aat gga gac ggc caa ctt gac tgg         1392
Ser Asn Ala Ser Leu Val Asp Ile Asn Gly Asp Gly Gln Leu Asp Trp
450                 455                 460 gtt atc acc gga ccg gga tta cgg gga tat cat agt caa cgc ccg gat         1440
Val Ile Thr Gly Pro Gly Leu Arg Gly Tyr His Ser Gln Arg Pro Asp
465                 470                 475                 480 ggc agt tgg aca cgt ttt acc cca ctc aac gct ctg ccg gtg gaa tac         1488
```

```
Gly Ser Trp Thr Arg Phe Thr Pro Leu Asn Ala Leu Pro Val Glu Tyr
            485                 490                 495 acc cat cca cgc gcg caa ctc gca gat tta atg gga gcc ggg cta tcc    1536
Thr His Pro Arg Ala Gln Leu Ala Asp Leu Met Gly Ala Gly Leu Ser
        500                 505                 510 gat ttg gtg ctg atc ggc cct aag agc gtg cgt tta tat gcc aat acc    1584
Asp Leu Val Leu Ile Gly Pro Lys Ser Val Arg Leu Tyr Ala Asn Thr
    515                 520                 525 cgc gac ggc ttt gcc aaa gga aaa gat gtg gtg caa tcc ggt gat atc    1632
Arg Asp Gly Phe Ala Lys Gly Lys Asp Val Val Gln Ser Gly Asp Ile
530                 535                 540 aca ctg ccg gtg ccg ggc gcc gat cca cgt aag ttg gtg gcg ttt agt    1680
Thr Leu Pro Val Pro Gly Ala Asp Pro Arg Lys Leu Val Ala Phe Ser
545                 550                 555                 560 gat gta ttg ggt tca ggt caa gcc cat ctg gtt gaa gta agc gcg act    1728
Asp Val Leu Gly Ser Gly Gln Ala His Leu Val Glu Val Ser Ala Thr
                565                 570                 575 aaa gtc acc tgc tgg cct aat ctg ggg cgc gga cgt ttt ggt caa ccc    1776
Lys Val Thr Cys Trp Pro Asn Leu Gly Arg Gly Arg Phe Gly Gln Pro
            580                 585                 590 att acc tta ccg gga ttc agc cag cca gca acc gag ttt aac ccg gct    1824
Ile Thr Leu Pro Gly Phe Ser Gln Pro Ala Thr Glu Phe Asn Pro Ala
        595                 600                 605 caa gtt tat ctg gcc gat ctg gat ggc agc ggt cca acg gat ctg att    1872
Gln Val Tyr Leu Ala Asp Leu Asp Gly Ser Gly Pro Thr Asp Leu Ile
    610                 615                 620 tat gtt cat aca aac cgt ctg gat atc ttc ctg aac aaa agt ggc aat    1920
Tyr Val His Thr Asn Arg Leu Asp Ile Phe Leu Asn Lys Ser Gly Asn
625                 630                 635                 640 ggc ttt gct gaa cca gtg aca tta cgc ttc ccg gaa ggt ctg cgt ttt    1968
Gly Phe Ala Glu Pro Val Thr Leu Arg Phe Pro Glu Gly Leu Arg Phe
                645                 650                 655 gat cat acc tgt cag tta caa atg gcc gat gta caa gga tta ggc gtc    2016
Asp His Thr Cys Gln Leu Gln Met Ala Asp Val Gln Gly Leu Gly Val
            660                 665                 670 gcc agc ctg ata ctg agc gtg ccg cat atg tct ccc cat cac tgg cgc    2064
Ala Ser Leu Ile Leu Ser Val Pro His Met Ser Pro His His Trp Arg
        675                 680                 685 tgc gat ctg acc aac atg aag ccg tgg tta ctc aat gaa atg aac aac    2112
Cys Asp Leu Thr Asn Met Lys Pro Trp Leu Leu Asn Glu Met Asn Asn
    690                 695                 700 aat atg ggg gtc cat cac acc ttg cgt tac cgc agt tcc tcc caa ttc    2160
Asn Met Gly Val His His Thr Leu Arg Tyr Arg Ser Ser Ser Gln Phe
705                 710                 715                 720 tgg ctg gat gaa aaa gcc gcg gcg ctg act acc gga caa aca ccg gtt    2208
Trp Leu Asp Glu Lys Ala Ala Ala Leu Thr Thr Gly Gln Thr Pro Val
                725                 730                 735 tgc tat ctc ccc ttc ccg atc cac acc cta tgg caa acg gaa aca gaa    2256
Cys Tyr Leu Pro Phe Pro Ile His Thr Leu Trp Gln Thr Glu Thr Glu
            740                 745                 750 gat gaa atc agc ggc aac aaa tta gtc aca aca ctt cgt tat gct cgt    2304
Asp Glu Ile Ser Gly Asn Lys Leu Val Thr Thr Leu Arg Tyr Ala Arg
        755                 760                 765 ggc gca tgg gac gga cgc gag cgg gaa ttt cgc gga ttt ggt tat gta    2352
Gly Ala Trp Asp Gly Arg Glu Arg Glu Phe Arg Gly Phe Gly Tyr Val
    770                 775                 780 gag cag aca gac agc cat caa ctg gct caa ggc aac gcg cca gaa cgt    2400
Glu Gln Thr Asp Ser His Gln Leu Ala Gln Gly Asn Ala Pro Glu Arg
785                 790                 795                 800
```

```
                                                              -continued acg cca ccg gcg ctg acc aaa aac tgg tat gcc acc gga ctg ccg gtg        2448
Thr Pro Pro Ala Leu Thr Lys Asn Trp Tyr Ala Thr Gly Leu Pro Val
                805                 810                 815 ata gat aac gca tta tca acc gag tat tgg cgt gat gat cag gct ttt        2496
Ile Asp Asn Ala Leu Ser Thr Glu Tyr Trp Arg Asp Asp Gln Ala Phe
            820                 825                 830 gcc ggt ttc tca ccg cgc ttt acg act tgg caa gat aac aaa gat gtc        2544
Ala Gly Phe Ser Pro Arg Phe Thr Thr Trp Gln Asp Asn Lys Asp Val
        835                 840                 845 ccg tta aca ccg gaa gat gat aac agt cgt tac tgg ttc aac cgc gcg        2592
Pro Leu Thr Pro Glu Asp Asp Asn Ser Arg Tyr Trp Phe Asn Arg Ala
    850                 855                 860 ttg aaa ggt caa ctg cta cgt agt gaa ctg tac gga ttg gac gat agt        2640
Leu Lys Gly Gln Leu Leu Arg Ser Glu Leu Tyr Gly Leu Asp Asp Ser
865                 870                 875                 880 aca aat aaa cac gtt ccc tat act gtc act gaa ttt cgt tca cag gta        2688
Thr Asn Lys His Val Pro Tyr Thr Val Thr Glu Phe Arg Ser Gln Val
                885                 890                 895 cgt cga tta cag cat acc gac agc cga tac cct gta ctt tgg tca tct        2736
Arg Arg Leu Gln His Thr Asp Ser Arg Tyr Pro Val Leu Trp Ser Ser
            900                 905                 910 gta gtt gaa agc cgc aac tat cac tac gaa cgt atc gcc agc gac ccg        2784
Val Val Glu Ser Arg Asn Tyr His Tyr Glu Arg Ile Ala Ser Asp Pro
        915                 920                 925 caa tgc agt caa aat att acg cta tcc agt gat cga ttt ggt cag ccg        2832
Gln Cys Ser Gln Asn Ile Thr Leu Ser Ser Asp Arg Phe Gly Gln Pro
    930                 935                 940 cta aaa cag ctt tcg gta cag tac ccg cgc cgc cag cag cca gca atc        2880
Leu Lys Gln Leu Ser Val Gln Tyr Pro Arg Arg Gln Gln Pro Ala Ile
945                 950                 955                 960 aat ctg tat cct gat aca ttg cct gat aag ttg tta gcc aac agc tat        2928
Asn Leu Tyr Pro Asp Thr Leu Pro Asp Lys Leu Leu Ala Asn Ser Tyr
                965                 970                 975 gat gac caa caa cgc caa tta cgg ctc acc tat caa caa tcc agt tgg        2976
Asp Asp Gln Gln Arg Gln Leu Arg Leu Thr Tyr Gln Gln Ser Ser Trp
            980                 985                 990 cat cac ctg acc aac aat acc gtt  cga gta ttg gga tta  ccg gat agt      3024
His His Leu Thr Asn Asn Thr Val  Arg Val Leu Gly Leu  Pro Asp Ser
        995                 1000                 1005 acc cgc  agt gat atc ttt act  tat ggc gct gaa aat  gtg cct gct         3069
Thr Arg  Ser Asp Ile Phe Thr  Tyr Gly Ala Glu Asn  Val Pro Ala
    1010                 1015                 1020 ggt ggt  tta aat ctg gaa ctt  ctg agt gat aaa aat  agc ctg atc         3114
Gly Gly  Leu Asn Leu Glu Leu  Leu Ser Asp Lys Asn  Ser Leu Ile
    1025                 1030                 1035 gcg gac  gat aaa cca cgt gaa  tac ctc ggt cag caa  aaa acc gct         3159
Ala Asp  Asp Lys Pro Arg Glu  Tyr Leu Gly Gln Gln  Lys Thr Ala
    1040                 1045                 1050 tat acc  gat gga caa aat aca  acg ccg ttg caa aca  cca aca cgg         3204
Tyr Thr  Asp Gly Gln Asn Thr  Thr Pro Leu Gln Thr  Pro Thr Arg
    1055                 1060                 1065 caa gcc  ctg att gcc ttt acc  gaa aca acg gta ttc  aac cag tcc         3249
Gln Ala  Leu Ile Ala Phe Thr  Glu Thr Thr Val Phe  Asn Gln Ser
    1070                 1075                 1080 aca tta  tca gcg ttt aac gga  agc atc ccg tcc gat  aaa tta tca         3294
Thr Leu  Ser Ala Phe Asn Gly  Ser Ile Pro Ser Asp  Lys Leu Ser
    1085                 1090                 1095 acg acg  ctg gag caa gct gga  tat cag caa aca aat  tat cta ttc         3339
Thr Thr  Leu Glu Gln Ala Gly  Tyr Gln Gln Thr Asn  Tyr Leu Phe
    1100                 1105                 1110
```

```
                                                    -continued cct cgc act gga gaa gat aaa gtt tgg gta gcc cat cac ggc tat       3384
Pro Arg Thr Gly Glu Asp Lys Val Trp Val Ala His His Gly Tyr
    1115                1120                1125 acc gat tat ggt aca gcg gca cag ttc tgg cgc ccg caa aaa cag       3429
Thr Asp Tyr Gly Thr Ala Ala Gln Phe Trp Arg Pro Gln Lys Gln
1130                1135                1140 agc aac acc caa ctc acc ggt aaa atc acc ctc atc tgg gat gca       3474
Ser Asn Thr Gln Leu Thr Gly Lys Ile Thr Leu Ile Trp Asp Ala
    1145                1150                1155 aac tat tgc gtt gtg gta caa acc cgg gat gct gct gga ctg aca       3519
Asn Tyr Cys Val Val Val Gln Thr Arg Asp Ala Ala Gly Leu Thr
1160                1165                1170 acc tca gcc aaa tat gac tgg cgt ttt ctg acc ccg gtg caa ctc       3564
Thr Ser Ala Lys Tyr Asp Trp Arg Phe Leu Thr Pro Val Gln Leu
    1175                1180                1185 acc gat atc aat gac aat cag cac ctt atc aca ctg gat gca ttg       3609
Thr Asp Ile Asn Asp Asn Gln His Leu Ile Thr Leu Asp Ala Leu
1190                1195                1200 ggc cga cca atc aca ttg cgc ttt tgg gga act gaa aac ggc aag       3654
Gly Arg Pro Ile Thr Leu Arg Phe Trp Gly Thr Glu Asn Gly Lys
    1205                1210                1215 atg aca ggt tat tcc tca ccg gaa aaa gca tca ttt tct cca cca       3699
Met Thr Gly Tyr Ser Ser Pro Glu Lys Ala Ser Phe Ser Pro Pro
1220                1225                1230 tcc gat gtt aat gcc gct att gag tta aaa aaa ccg ctc cct gta       3744
Ser Asp Val Asn Ala Ala Ile Glu Leu Lys Lys Pro Leu Pro Val
    1235                1240                1245 gca cag tgt cag gtc tac gca cca gaa agc tgg atg cca gta tta       3789
Ala Gln Cys Gln Val Tyr Ala Pro Glu Ser Trp Met Pro Val Leu
1250                1255                1260 agt cag aaa acc ttc aat cga ctg gca gaa caa gat tgg caa aag       3834
Ser Gln Lys Thr Phe Asn Arg Leu Ala Glu Gln Asp Trp Gln Lys
    1265                1270                1275 tta tat aac gcc cga atc atc acc gaa gat gga cgt atc tgc aca       3879
Leu Tyr Asn Ala Arg Ile Ile Thr Glu Asp Gly Arg Ile Cys Thr
1280                1285                1290 ctg gct tat cgc cgc tgg gta caa agc caa aag gca atc cct caa       3924
Leu Ala Tyr Arg Arg Trp Val Gln Ser Gln Lys Ala Ile Pro Gln
    1295                1300                1305 ctc att agc ctg tta aac aac gga ccc cgt tta cct cct cac agc       3969
Leu Ile Ser Leu Leu Asn Asn Gly Pro Arg Leu Pro Pro His Ser
1310                1315                1320 ctg aca ttg acg acg gat cgt tat gat cac gat cct gag caa cag       4014
Leu Thr Leu Thr Thr Asp Arg Tyr Asp His Asp Pro Glu Gln Gln
    1325                1330                1335 atc cgt caa cag gtg gta ttc agt gat ggc ttt ggc cgc ttg ctg       4059
Ile Arg Gln Gln Val Val Phe Ser Asp Gly Phe Gly Arg Leu Leu
1340                1345                1350 caa gcc gct gcc cga cat gag gca ggc atg gcc cgg caa cgc aat       4104
Gln Ala Ala Ala Arg His Glu Ala Gly Met Ala Arg Gln Arg Asn
    1355                1360                1365 gaa gac ggc tct ttg att ata aat gtc cag cat act gag aac cgt       4149
Glu Asp Gly Ser Leu Ile Ile Asn Val Gln His Thr Glu Asn Arg
1370                1375                1380 tgg gca gtg act gga cga acg gaa tat gac aat aag ggg caa ccg       4194
Trp Ala Val Thr Gly Arg Thr Glu Tyr Asp Asn Lys Gly Gln Pro
    1385                1390                1395 ata cgt acc tat cag ccc tat ttc ctc aat gac tgg cga tac gtc       4239
Ile Arg Thr Tyr Gln Pro Tyr Phe Leu Asn Asp Trp Arg Tyr Val
```

```
agc aat gat agt gcc cgg cag gaa aaa gaa gct tat gca gat acc    4284
Ser Asn Asp Ser Ala Arg Gln Glu Lys Glu Ala Tyr Ala Asp Thr
    1415                1420                1425 cat gtc tat gat ccc ata ggt cga gaa atc aag gtt atc acc gca    4329
His Val Tyr Asp Pro Ile Gly Arg Glu Ile Lys Val Ile Thr Ala
1430                1435                1440 aaa ggt tgg ttc cgt cga acc ttg ttc act ccc tgg ttt act gtc    4374
Lys Gly Trp Phe Arg Arg Thr Leu Phe Thr Pro Trp Phe Thr Val
    1445                1450                1455 aat gaa gat gaa aat gac aca gcc gct gag gtg aag aag gta aag    4419
Asn Glu Asp Glu Asn Asp Thr Ala Ala Glu Val Lys Lys Val Lys
1460                1465                1470 atg taa                                                        4425
Met
```

<210> SEQ ID NO 10
<211> LENGTH: 1474
<212> TYPE: PRT
<213> ORGANISM: Photorhabdus luminescens

<400> SEQUENCE: 10

```
Met Gln Asn Ser Gln Asp Phe Ser Ile Thr Glu Leu Ser Leu Pro Lys
1               5                   10                  15

Gly Gly Gly Ala Ile Thr Gly Met Gly Glu Ala Leu Thr Pro Thr Gly
            20                  25                  30

Pro Asp Gly Met Ala Ala Leu Ser Leu Pro Leu Pro Ile Ser Ala Gly
        35                  40                  45

Arg Gly Tyr Ala Pro Ala Phe Thr Leu Asn Tyr Asn Ser Gly Ala Gly
    50                  55                  60

Asn Ser Pro Phe Gly Leu Gly Trp Asp Cys Asn Val Met Thr Ile Arg
65                  70                  75                  80

Arg Arg Thr His Phe Gly Val Pro His Tyr Asp Glu Thr Asp Thr Phe
                85                  90                  95

Leu Gly Pro Glu Gly Glu Val Leu Val Val Ala Asp Gln Pro Arg Asp
            100                 105                 110

Glu Ser Thr Leu Gln Gly Ile Asn Leu Gly Ala Thr Phe Thr Val Thr
        115                 120                 125

Gly Tyr Arg Ser Arg Leu Glu Ser His Phe Ser Arg Leu Glu Tyr Trp
    130                 135                 140

Gln Pro Lys Thr Thr Gly Lys Thr Asp Phe Trp Leu Ile Tyr Ser Pro
145                 150                 155                 160

Asp Gly Gln Val His Leu Leu Gly Lys Ser Pro Gln Ala Arg Ile Ser
                165                 170                 175

Asn Pro Ser Gln Thr Thr Gln Thr Ala Gln Trp Leu Leu Glu Ala Ser
            180                 185                 190

Val Ser Ser Arg Gly Glu Gln Ile Tyr Tyr Gln Tyr Arg Ala Glu Asp
        195                 200                 205

Asp Thr Gly Cys Glu Ala Asp Glu Ile Thr His His Leu Gln Ala Thr
    210                 215                 220

Ala Gln Arg Tyr Leu His Ile Val Tyr Gly Asn Arg Thr Ala Ser
225                 230                 235                 240

Glu Thr Leu Pro Gly Leu Asp Gly Ser Ala Pro Ser Gln Ala Asp Trp
                245                 250                 255

Leu Phe Tyr Leu Val Phe Asp Tyr Gly Glu Arg Ser Asn Asn Leu Lys
            260                 265                 270
```

-continued

```
Thr Pro Pro Ala Phe Ser Thr Thr Gly Ser Trp Leu Cys Arg Gln Asp
            275                 280                 285

Arg Phe Ser Arg Tyr Glu Tyr Gly Phe Glu Ile Arg Thr Arg Arg Leu
        290                 295                 300

Cys Arg Gln Val Leu Met Tyr His His Leu Gln Ala Leu Asp Ser Lys
305                 310                 315                 320

Ile Thr Glu His Asn Gly Pro Thr Leu Val Ser Arg Leu Ile Leu Asn
                325                 330                 335

Tyr Asp Glu Ser Ala Ile Ala Ser Thr Leu Val Phe Val Arg Arg Val
            340                 345                 350

Gly His Glu Gln Asp Gly Asn Val Val Thr Leu Pro Leu Glu Leu
        355                 360                 365

Ala Tyr Gln Asp Phe Ser Pro Arg His His Ala His Trp Gln Pro Met
    370                 375                 380

Asp Val Leu Ala Asn Phe Asn Ala Ile Gln Arg Trp Gln Leu Val Asp
385                 390                 395                 400

Leu Lys Gly Glu Gly Leu Pro Gly Leu Leu Tyr Gln Asp Lys Gly Ala
                405                 410                 415

Trp Trp Tyr Arg Ser Ala Gln Arg Leu Gly Glu Ile Gly Ser Asp Ala
            420                 425                 430

Val Thr Trp Glu Lys Met Gln Pro Leu Ser Val Ile Pro Ser Leu Gln
        435                 440                 445

Ser Asn Ala Ser Leu Val Asp Ile Asn Gly Asp Gly Gln Leu Asp Trp
450                 455                 460

Val Ile Thr Gly Pro Gly Leu Arg Gly Tyr His Ser Gln Arg Pro Asp
465                 470                 475                 480

Gly Ser Trp Thr Arg Phe Thr Pro Leu Asn Ala Leu Pro Val Glu Tyr
                485                 490                 495

Thr His Pro Arg Ala Gln Leu Ala Asp Leu Met Gly Ala Gly Leu Ser
            500                 505                 510

Asp Leu Val Leu Ile Gly Pro Lys Ser Val Arg Leu Tyr Ala Asn Thr
        515                 520                 525

Arg Asp Gly Phe Ala Lys Gly Lys Asp Val Val Gln Ser Gly Asp Ile
    530                 535                 540

Thr Leu Pro Val Pro Gly Ala Asp Pro Arg Lys Leu Val Ala Phe Ser
545                 550                 555                 560

Asp Val Leu Gly Ser Gly Gln Ala His Leu Val Glu Val Ser Ala Thr
                565                 570                 575

Lys Val Thr Cys Trp Pro Asn Leu Gly Arg Gly Arg Phe Gly Gln Pro
            580                 585                 590

Ile Thr Leu Pro Gly Phe Ser Gln Pro Ala Thr Glu Phe Asn Pro Ala
        595                 600                 605

Gln Val Tyr Leu Ala Asp Leu Asp Gly Ser Gly Pro Thr Asp Leu Ile
    610                 615                 620

Tyr Val His Thr Asn Arg Leu Asp Ile Phe Leu Asn Lys Ser Gly Asn
625                 630                 635                 640

Gly Phe Ala Glu Pro Val Thr Leu Arg Phe Pro Glu Gly Leu Arg Phe
                645                 650                 655

Asp His Thr Cys Gln Leu Gln Met Ala Asp Val Gln Gly Leu Gly Val
            660                 665                 670

Ala Ser Leu Ile Leu Ser Val Pro His Met Ser Pro His His Trp Arg
        675                 680                 685
```

```
Cys Asp Leu Thr Asn Met Lys Pro Trp Leu Leu Asn Glu Met Asn Asn
690                 695                 700

Asn Met Gly Val His His Thr Leu Arg Tyr Arg Ser Ser Ser Gln Phe
705                 710                 715                 720

Trp Leu Asp Glu Lys Ala Ala Ala Leu Thr Thr Gly Gln Thr Pro Val
                725                 730                 735

Cys Tyr Leu Pro Phe Pro Ile His Thr Leu Trp Gln Thr Glu Thr Glu
                740                 745                 750

Asp Glu Ile Ser Gly Asn Lys Leu Val Thr Thr Leu Arg Tyr Ala Arg
                755                 760                 765

Gly Ala Trp Asp Gly Arg Glu Arg Glu Phe Arg Gly Phe Gly Tyr Val
770                 775                 780

Glu Gln Thr Asp Ser His Gln Leu Ala Gln Gly Asn Ala Pro Glu Arg
785                 790                 795                 800

Thr Pro Pro Ala Leu Thr Lys Asn Trp Tyr Ala Thr Gly Leu Pro Val
                805                 810                 815

Ile Asp Asn Ala Leu Ser Thr Glu Tyr Trp Arg Asp Gln Ala Phe
                820                 825                 830

Ala Gly Phe Ser Pro Arg Phe Thr Thr Trp Gln Asp Asn Lys Asp Val
                835                 840                 845

Pro Leu Thr Pro Glu Asp Asp Asn Ser Arg Tyr Trp Phe Asn Arg Ala
850                 855                 860

Leu Lys Gly Gln Leu Leu Arg Ser Glu Leu Tyr Gly Leu Asp Asp Ser
865                 870                 875                 880

Thr Asn Lys His Val Pro Tyr Thr Val Thr Glu Phe Arg Ser Gln Val
                885                 890                 895

Arg Arg Leu Gln His Thr Asp Ser Arg Tyr Pro Val Leu Trp Ser Ser
                900                 905                 910

Val Val Glu Ser Arg Asn Tyr His Tyr Glu Arg Ile Ala Ser Asp Pro
                915                 920                 925

Gln Cys Ser Gln Asn Ile Thr Leu Ser Ser Asp Arg Phe Gly Gln Pro
930                 935                 940

Leu Lys Gln Leu Ser Val Gln Tyr Pro Arg Gln Gln Pro Ala Ile
945                 950                 955                 960

Asn Leu Tyr Pro Asp Thr Leu Pro Asp Lys Leu Leu Ala Asn Ser Tyr
                965                 970                 975

Asp Asp Gln Gln Arg Gln Leu Arg Leu Thr Tyr Gln Ser Ser Trp
                980                 985                 990

His His Leu Thr Asn Asn Thr Val Arg Val Leu Gly Leu Pro Asp Ser
                995                 1000                1005

Thr Arg Ser Asp Ile Phe Thr Tyr Gly Ala Glu Asn Val Pro Ala
    1010                1015                1020

Gly Gly Leu Asn Leu Glu Leu Leu Ser Asp Lys Asn Ser Leu Ile
    1025                1030                1035

Ala Asp Asp Lys Pro Arg Glu Tyr Leu Gly Gln Gln Lys Thr Ala
    1040                1045                1050

Tyr Thr Asp Gly Gln Asn Thr Thr Pro Leu Gln Thr Pro Thr Arg
    1055                1060                1065

Gln Ala Leu Ile Ala Phe Thr Glu Thr Thr Val Phe Asn Gln Ser
    1070                1075                1080

Thr Leu Ser Ala Phe Asn Gly Ser Ile Pro Ser Asp Lys Leu Ser
    1085                1090                1095

Thr Thr Leu Glu Gln Ala Gly Tyr Gln Gln Thr Asn Tyr Leu Phe
```

```
                    1100             1105            1110
Pro Arg Thr Gly Glu Asp Lys Val Trp Val Ala His His Gly Tyr
1115                1120            1125

Thr Asp Tyr Gly Thr Ala Ala Gln Phe Trp Arg Pro Gln Lys Gln
1130                1135            1140

Ser Asn Thr Gln Leu Thr Gly Lys Ile Thr Leu Ile Trp Asp Ala
1145                1150            1155

Asn Tyr Cys Val Val Val Gln Thr Arg Asp Ala Ala Gly Leu Thr
1160                1165            1170

Thr Ser Ala Lys Tyr Asp Trp Arg Phe Leu Thr Pro Val Gln Leu
1175                1180            1185

Thr Asp Ile Asn Asp Asn Gln His Leu Ile Thr Leu Asp Ala Leu
1190                1195            1200

Gly Arg Pro Ile Thr Leu Arg Phe Trp Gly Thr Glu Asn Gly Lys
1205                1210            1215

Met Thr Gly Tyr Ser Ser Pro Glu Lys Ala Ser Phe Ser Pro Pro
1220                1225            1230

Ser Asp Val Asn Ala Ala Ile Glu Leu Lys Lys Pro Leu Pro Val
1235                1240            1245

Ala Gln Cys Gln Val Tyr Ala Pro Glu Ser Trp Met Pro Val Leu
1250                1255            1260

Ser Gln Lys Thr Phe Asn Arg Leu Ala Glu Gln Asp Trp Gln Lys
1265                1270            1275

Leu Tyr Asn Ala Arg Ile Ile Thr Glu Asp Gly Arg Ile Cys Thr
1280                1285            1290

Leu Ala Tyr Arg Arg Trp Val Gln Ser Gln Lys Ala Ile Pro Gln
1295                1300            1305

Leu Ile Ser Leu Leu Asn Asn Gly Pro Arg Leu Pro Pro His Ser
1310                1315            1320

Leu Thr Leu Thr Thr Asp Arg Tyr Asp His Asp Pro Glu Gln Gln
1325                1330            1335

Ile Arg Gln Gln Val Val Phe Ser Asp Gly Phe Gly Arg Leu Leu
1340                1345            1350

Gln Ala Ala Ala Arg His Glu Ala Gly Met Ala Arg Gln Arg Asn
1355                1360            1365

Glu Asp Gly Ser Leu Ile Ile Asn Val Gln His Thr Glu Asn Arg
1370                1375            1380

Trp Ala Val Thr Gly Arg Thr Glu Tyr Asp Asn Lys Gly Gln Pro
1385                1390            1395

Ile Arg Thr Tyr Gln Pro Tyr Phe Leu Asn Asp Trp Arg Tyr Val
1400                1405            1410

Ser Asn Asp Ser Ala Arg Gln Glu Lys Glu Ala Tyr Ala Asp Thr
1415                1420            1425

His Val Tyr Asp Pro Ile Gly Arg Glu Ile Lys Val Ile Thr Ala
1430                1435            1440

Lys Gly Trp Phe Arg Arg Thr Leu Phe Thr Pro Trp Phe Thr Val
1445                1450            1455

Asn Glu Asp Glu Asn Asp Thr Ala Ala Glu Val Lys Lys Val Lys
1460                1465            1470

Met

<210> SEQ ID NO 11
<211> LENGTH: 2883
```

```
<212> TYPE: DNA
<213> ORGANISM: Photorhabdus luminescens
<220> FEATURE:
<221> NAME/KEY: CDS
<222> LOCATION: (1)..(2880)

<400> SEQUENCE: 11
```

| | | | | | | | | | | | | | | | | |
|---|---|---|---|---|---|---|---|---|---|---|---|---|---|---|---|---|
| atg | aaa | aac | att | gat | ccc | aaa | ctt | tat | caa | aaa | acc | cct | act | gtc | agc | 48 |
| Met | Lys | Asn | Ile | Asp | Pro | Lys | Leu | Tyr | Gln | Lys | Thr | Pro | Thr | Val | Ser | |
| 1 | | | | 5 | | | | | 10 | | | | | 15 | | |
| gtt | tac | gat | aac | cgt | ggt | ctg | ata | atc | cgt | aac | atc | gat | ttt | cat | cgt | 96 |
| Val | Tyr | Asp | Asn | Arg | Gly | Leu | Ile | Ile | Arg | Asn | Ile | Asp | Phe | His | Arg | |
| | | | 20 | | | | | 25 | | | | | 30 | | | |
| act | acc | gca | aat | ggt | gat | ccc | gat | acc | cgt | att | acc | cgc | cat | caa | tac | 144 |
| Thr | Thr | Ala | Asn | Gly | Asp | Pro | Asp | Thr | Arg | Ile | Thr | Arg | His | Gln | Tyr | |
| | | 35 | | | | | 40 | | | | | 45 | | | | |
| gat | att | cac | gga | cac | cta | aat | caa | agc | atc | gat | ccg | cgc | cta | tat | gaa | 192 |
| Asp | Ile | His | Gly | His | Leu | Asn | Gln | Ser | Ile | Asp | Pro | Arg | Leu | Tyr | Glu | |
| | 50 | | | | | 55 | | | | | 60 | | | | | |
| gcc | aag | caa | acc | aac | aat | acg | atc | aaa | ccc | aat | ttt | ctt | tgg | cag | tat | 240 |
| Ala | Lys | Gln | Thr | Asn | Asn | Thr | Ile | Lys | Pro | Asn | Phe | Leu | Trp | Gln | Tyr | |
| 65 | | | | | 70 | | | | | 75 | | | | | 80 | |
| gat | ttg | acc | ggt | aat | ccc | cta | tgt | aca | gag | agc | att | gat | gca | ggt | cgc | 288 |
| Asp | Leu | Thr | Gly | Asn | Pro | Leu | Cys | Thr | Glu | Ser | Ile | Asp | Ala | Gly | Arg | |
| | | | | 85 | | | | | 90 | | | | | 95 | | |
| act | gtc | acc | ttg | aat | gat | att | gaa | ggc | cgt | ccg | cta | cta | acg | gtg | act | 336 |
| Thr | Val | Thr | Leu | Asn | Asp | Ile | Glu | Gly | Arg | Pro | Leu | Leu | Thr | Val | Thr | |
| | | | 100 | | | | | 105 | | | | | 110 | | | |
| gca | aca | ggg | gtt | ata | caa | act | cga | caa | tat | gaa | act | tct | tcc | ctg | ccc | 384 |
| Ala | Thr | Gly | Val | Ile | Gln | Thr | Arg | Gln | Tyr | Glu | Thr | Ser | Ser | Leu | Pro | |
| | | 115 | | | | | 120 | | | | | 125 | | | | |
| ggt | cgt | ctg | tta | tct | gtt | gcc | gaa | caa | aca | ccc | gag | gaa | aaa | aca | tcc | 432 |
| Gly | Arg | Leu | Leu | Ser | Val | Ala | Glu | Gln | Thr | Pro | Glu | Glu | Lys | Thr | Ser | |
| | 130 | | | | | 135 | | | | | 140 | | | | | |
| cgt | atc | acc | gaa | cgc | ctg | att | tgg | gct | ggc | aat | acc | gaa | gca | gag | aaa | 480 |
| Arg | Ile | Thr | Glu | Arg | Leu | Ile | Trp | Ala | Gly | Asn | Thr | Glu | Ala | Glu | Lys | |
| 145 | | | | | 150 | | | | | 155 | | | | | 160 | |
| gac | cat | aac | ctt | gcc | ggc | cag | tgc | gtg | cgt | cac | tat | gac | acg | gcg | gga | 528 |
| Asp | His | Asn | Leu | Ala | Gly | Gln | Cys | Val | Arg | His | Tyr | Asp | Thr | Ala | Gly | |
| | | | | 165 | | | | | 170 | | | | | 175 | | |
| gtt | acc | cgg | tta | gag | agt | tta | tca | ctg | acc | ggt | act | gtt | tta | tct | caa | 576 |
| Val | Thr | Arg | Leu | Glu | Ser | Leu | Ser | Leu | Thr | Gly | Thr | Val | Leu | Ser | Gln | |
| | | | 180 | | | | | 185 | | | | | 190 | | | |
| tcc | agc | caa | cta | ttg | atc | gac | act | caa | gag | gca | aac | tgg | aca | ggt | gat | 624 |
| Ser | Ser | Gln | Leu | Leu | Ile | Asp | Thr | Gln | Glu | Ala | Asn | Trp | Thr | Gly | Asp | |
| | | 195 | | | | | 200 | | | | | 205 | | | | |
| aac | gaa | acc | gtc | tgg | caa | aac | atg | ctg | gct | gat | gac | atc | tac | aca | acc | 672 |
| Asn | Glu | Thr | Val | Trp | Gln | Asn | Met | Leu | Ala | Asp | Asp | Ile | Tyr | Thr | Thr | |
| | 210 | | | | | 215 | | | | | 220 | | | | | |
| ctg | agc | acc | ttc | gat | gcc | acc | ggt | gct | tta | ctg | act | cag | acc | gat | gcg | 720 |
| Leu | Ser | Thr | Phe | Asp | Ala | Thr | Gly | Ala | Leu | Leu | Thr | Gln | Thr | Asp | Ala | |
| 225 | | | | | 230 | | | | | 235 | | | | | 240 | |
| aaa | ggg | aac | att | cag | aga | ctg | gct | tat | gat | gtg | gcc | ggg | cag | cta | aac | 768 |
| Lys | Gly | Asn | Ile | Gln | Arg | Leu | Ala | Tyr | Asp | Val | Ala | Gly | Gln | Leu | Asn | |
| | | | | 245 | | | | | 250 | | | | | 255 | | |
| ggg | agc | tgg | cta | aca | ctc | aaa | ggc | cag | acg | gaa | caa | gtg | att | atc | aaa | 816 |
| Gly | Ser | Trp | Leu | Thr | Leu | Lys | Gly | Gln | Thr | Glu | Gln | Val | Ile | Ile | Lys | |
| | | | 260 | | | | | 265 | | | | | 270 | | | |
| tcc | ctg | acc | tac | tcc | gcc | gcc | gga | caa | aaa | tta | cgt | gag | gaa | cac | ggc | 864 |
| Ser | Leu | Thr | Tyr | Ser | Ala | Ala | Gly | Gln | Lys | Leu | Arg | Glu | Glu | His | Gly | |
| | | 275 | | | | | 280 | | | | | 285 | | | | |

-continued

```
aat gat gtt atc acc gaa tac agt tat gaa ccg gaa acc caa cgg ctg      912
Asn Asp Val Ile Thr Glu Tyr Ser Tyr Glu Pro Glu Thr Gln Arg Leu
    290                 295                 300 atc ggt atc aaa acc cgc cgt ccg tca gac act aaa gtg cta caa gac      960
Ile Gly Ile Lys Thr Arg Arg Pro Ser Asp Thr Lys Val Leu Gln Asp
305                 310                 315                 320 ctg cgc tat gaa tat gac ccg gta ggc aat gtc atc agc atc cgt aat     1008
Leu Arg Tyr Glu Tyr Asp Pro Val Gly Asn Val Ile Ser Ile Arg Asn
                325                 330                 335 gac gcg gaa gcc acc cgc ttt tgg cac aat cag aaa gtg atg ccg gaa     1056
Asp Ala Glu Ala Thr Arg Phe Trp His Asn Gln Lys Val Met Pro Glu
            340                 345                 350 aac act tat acc tac gat tcc ctg tat cag ctt atc agc gcc acc ggg     1104
Asn Thr Tyr Thr Tyr Asp Ser Leu Tyr Gln Leu Ile Ser Ala Thr Gly
        355                 360                 365 cgc gaa atg gcg aat ata ggt caa caa agt cac caa ttt ccc tca ccc     1152
Arg Glu Met Ala Asn Ile Gly Gln Gln Ser His Gln Phe Pro Ser Pro
    370                 375                 380 gct cta cct tct gat aac aac acc tat acc aac tat acc cgt act tat     1200
Ala Leu Pro Ser Asp Asn Asn Thr Tyr Thr Asn Tyr Thr Arg Thr Tyr
385                 390                 395                 400 act tat gac cgt ggc ggc aat ctg acc aaa atc cag cac agt tca ccg     1248
Thr Tyr Asp Arg Gly Gly Asn Leu Thr Lys Ile Gln His Ser Ser Pro
                405                 410                 415 gcg acg caa aac aac tac acc acc aat atc acg gtt tca aat cgc agc     1296
Ala Thr Gln Asn Asn Tyr Thr Thr Asn Ile Thr Val Ser Asn Arg Ser
            420                 425                 430 aac cgc gca gta ctc agc aca ttg acc gaa gat ccg gcg caa gta gat     1344
Asn Arg Ala Val Leu Ser Thr Leu Thr Glu Asp Pro Ala Gln Val Asp
        435                 440                 445 gct ttg ttt gat gca ggc gga cat cag aac acc ttg ata tca gga caa     1392
Ala Leu Phe Asp Ala Gly Gly His Gln Asn Thr Leu Ile Ser Gly Gln
    450                 455                 460 aac ctg aac tgg aat act cgt ggt gaa ctg caa caa gta aca ctg gtt     1440
Asn Leu Asn Trp Asn Thr Arg Gly Glu Leu Gln Gln Val Thr Leu Val
465                 470                 475                 480 aaa cgg gac aag ggc gcc aat gat gat cgg gaa tgg tat cgt tat agc     1488
Lys Arg Asp Lys Gly Ala Asn Asp Asp Arg Glu Trp Tyr Arg Tyr Ser
                485                 490                 495 ggt gac gga aga agg atg tta aaa atc aat gaa cag cag gcc agc aac     1536
Gly Asp Gly Arg Arg Met Leu Lys Ile Asn Glu Gln Gln Ala Ser Asn
            500                 505                 510 aac gct caa aca caa cgt gtg act tat ttg ccg aac tta gaa ctt cgt     1584
Asn Ala Gln Thr Gln Arg Val Thr Tyr Leu Pro Asn Leu Glu Leu Arg
        515                 520                 525 cta aca caa aac agc acg gcc aca acc gaa gat ttg caa gtt atc acc     1632
Leu Thr Gln Asn Ser Thr Ala Thr Thr Glu Asp Leu Gln Val Ile Thr
    530                 535                 540 gta ggc gaa gcg ggc cgg gca cag gta cga gta tta cat tgg gag agc     1680
Val Gly Glu Ala Gly Arg Ala Gln Val Arg Val Leu His Trp Glu Ser
545                 550                 555                 560 ggt aaa ccg gaa gat atc gac aat aat cag ttg cgt tat agt tac gat     1728
Gly Lys Pro Glu Asp Ile Asp Asn Asn Gln Leu Arg Tyr Ser Tyr Asp
                565                 570                 575 aat ctt atc ggt tcc agt caa ctt gaa tta gat agc gaa gga caa att     1776
Asn Leu Ile Gly Ser Ser Gln Leu Glu Leu Asp Ser Glu Gly Gln Ile
            580                 585                 590 atc agt gaa gaa gaa tat tat ccc tat ggt gga aca gca tta tgg gcc     1824
Ile Ser Glu Glu Glu Tyr Tyr Pro Tyr Gly Gly Thr Ala Leu Trp Ala
```

-continued

```
                595                 600                 605
gcc agg aat cag aca gaa gcc agt tat aaa act atc cgt tat tca ggc     1872
Ala Arg Asn Gln Thr Glu Ala Ser Tyr Lys Thr Ile Arg Tyr Ser Gly
610                 615                 620 aaa gag cgg gat gcc acc ggg cta tat tac tac ggc tat cgt tat tac     1920
Lys Glu Arg Asp Ala Thr Gly Leu Tyr Tyr Tyr Gly Tyr Arg Tyr Tyr
625                 630                 635                 640 caa ccg tgg ata gga cgg tgg tta agc tcc gat ccg gca gga aca atc     1968
Gln Pro Trp Ile Gly Arg Trp Leu Ser Ser Asp Pro Ala Gly Thr Ile
                645                 650                 655 gat ggg ctg aat tta tat cgg atg gtg agg aat aat cca gtt acc ctc     2016
Asp Gly Leu Asn Leu Tyr Arg Met Val Arg Asn Asn Pro Val Thr Leu
                660                 665                 670 ctt gat cct gat gga tta atg cca aca att gca gaa cgc ata gca gca     2064
Leu Asp Pro Asp Gly Leu Met Pro Thr Ile Ala Glu Arg Ile Ala Ala
                675                 680                 685 cta aaa aaa aat aaa gta aca gac tca gcg cct tcg cca gca aat gcc     2112
Leu Lys Lys Asn Lys Val Thr Asp Ser Ala Pro Ser Pro Ala Asn Ala
690                 695                 700 aca aac gta gcg ata aac atc cgc ccg cct gta gca cca aaa cct agc     2160
Thr Asn Val Ala Ile Asn Ile Arg Pro Pro Val Ala Pro Lys Pro Ser
705                 710                 715                 720 tta ccg aaa gca tca acg agt agc caa cca acc aca cac cct atc gga     2208
Leu Pro Lys Ala Ser Thr Ser Ser Gln Pro Thr Thr His Pro Ile Gly
                725                 730                 735 gct gca aac ata aaa cca acg acg tct ggg tca tct att gtt gct cca     2256
Ala Ala Asn Ile Lys Pro Thr Thr Ser Gly Ser Ser Ile Val Ala Pro
                740                 745                 750 ttg agt cca gta gga aat aaa tct act tct gaa atc tct ctg cca gaa     2304
Leu Ser Pro Val Gly Asn Lys Ser Thr Ser Glu Ile Ser Leu Pro Glu
                755                 760                 765 agc gct caa agc agt tct tca agc act acc tcg aca aat cta cag aaa     2352
Ser Ala Gln Ser Ser Ser Ser Thr Thr Ser Thr Asn Leu Gln Lys
770                 775                 780 aaa tca ttt act tta tat aga gca gat aac aga tcc ttt gaa gaa atg     2400
Lys Ser Phe Thr Leu Tyr Arg Ala Asp Asn Arg Ser Phe Glu Glu Met
785                 790                 795                 800 caa agt aaa ttc cct gaa gga ttt aaa gcc tgg act cct cta gac act     2448
Gln Ser Lys Phe Pro Glu Gly Phe Lys Ala Trp Thr Pro Leu Asp Thr
                805                 810                 815 aag atg gca agg caa ttt gct agt atc ttt att ggt cag aaa gat aca     2496
Lys Met Ala Arg Gln Phe Ala Ser Ile Phe Ile Gly Gln Lys Asp Thr
                820                 825                 830 tct aat tta cct aaa gaa aca gtc aag aac ata agc aca tgg gga gca     2544
Ser Asn Leu Pro Lys Glu Thr Val Lys Asn Ile Ser Thr Trp Gly Ala
                835                 840                 845 aag cca aaa cta aaa gat ctc tca aat tac ata aaa tat acc aag gac     2592
Lys Pro Lys Leu Lys Asp Leu Ser Asn Tyr Ile Lys Tyr Thr Lys Asp
850                 855                 860 aaa tct aca gta tgg gtt tct act gca att aat act gaa gca ggt gga     2640
Lys Ser Thr Val Trp Val Ser Thr Ala Ile Asn Thr Glu Ala Gly Gly
865                 870                 875                 880 caa agc tca ggg gct cca ctc cat aaa att gat atg gat ctc tac gag     2688
Gln Ser Ser Gly Ala Pro Leu His Lys Ile Asp Met Asp Leu Tyr Glu
                885                 890                 895 ttt gcc att gat gga caa aaa cta aat cca cta ccg gag ggt aga act     2736
Phe Ala Ile Asp Gly Gln Lys Leu Asn Pro Leu Pro Glu Gly Arg Thr
                900                 905                 910 aaa aac atg gta cct tcc ctt tta ctc gac acc cca caa ata gag aca     2784
```

```
Lys Asn Met Val Pro Ser Leu Leu Asp Thr Pro Gln Ile Glu Thr
        915                 920                 925 tca tcc atc att gca ctt aat cat gga ccg gta aat gat gca gaa att      2832
Ser Ser Ile Ile Ala Leu Asn His Gly Pro Val Asn Asp Ala Glu Ile
930                 935                 940 tca ttt ctg aca aca att ccg ctt aaa aat gta aaa cct cat aag aga      2880
Ser Phe Leu Thr Thr Ile Pro Leu Lys Asn Val Lys Pro His Lys Arg
945                 950                 955                 960 taa                                                                   2883

<210> SEQ ID NO 12
<211> LENGTH: 960
<212> TYPE: PRT
<213> ORGANISM: Photorhabdus luminescens

<400> SEQUENCE: 12

Met Lys Asn Ile Asp Pro Lys Leu Tyr Gln Lys Thr Pro Thr Val Ser
1               5                   10                  15

Val Tyr Asp Asn Arg Gly Leu Ile Ile Arg Asn Ile Asp Phe His Arg
            20                  25                  30

Thr Thr Ala Asn Gly Asp Pro Asp Thr Arg Ile Thr Arg His Gln Tyr
        35                  40                  45

Asp Ile His Gly His Leu Asn Gln Ser Ile Asp Pro Arg Leu Tyr Glu
    50                  55                  60

Ala Lys Gln Thr Asn Asn Thr Ile Lys Pro Asn Phe Leu Trp Gln Tyr
65                  70                  75                  80

Asp Leu Thr Gly Asn Pro Leu Cys Thr Glu Ser Ile Asp Ala Gly Arg
                85                  90                  95

Thr Val Thr Leu Asn Asp Ile Glu Gly Arg Pro Leu Leu Thr Val Thr
            100                 105                 110

Ala Thr Gly Val Ile Gln Thr Arg Gln Tyr Glu Thr Ser Ser Leu Pro
        115                 120                 125

Gly Arg Leu Leu Ser Val Ala Glu Gln Thr Pro Glu Glu Lys Thr Ser
    130                 135                 140

Arg Ile Thr Glu Arg Leu Ile Trp Ala Gly Asn Thr Glu Ala Glu Lys
145                 150                 155                 160

Asp His Asn Leu Ala Gly Gln Cys Val Arg His Tyr Asp Thr Ala Gly
                165                 170                 175

Val Thr Arg Leu Glu Ser Leu Ser Leu Thr Gly Thr Val Leu Ser Gln
            180                 185                 190

Ser Ser Gln Leu Leu Ile Asp Thr Gln Glu Ala Asn Trp Thr Gly Asp
        195                 200                 205

Asn Glu Thr Val Trp Gln Asn Met Leu Ala Asp Ile Tyr Thr Thr
    210                 215                 220

Leu Ser Thr Phe Asp Ala Thr Gly Ala Leu Leu Thr Gln Thr Asp Ala
225                 230                 235                 240

Lys Gly Asn Ile Gln Arg Leu Ala Tyr Asp Val Ala Gly Gln Leu Asn
                245                 250                 255

Gly Ser Trp Leu Thr Leu Lys Gly Gln Thr Glu Gln Val Ile Ile Lys
            260                 265                 270

Ser Leu Thr Tyr Ser Ala Ala Gly Gln Lys Leu Arg Glu Glu His Gly
        275                 280                 285

Asn Asp Val Ile Thr Glu Tyr Ser Tyr Glu Pro Glu Thr Gln Arg Leu
    290                 295                 300

Ile Gly Ile Lys Thr Arg Arg Pro Ser Asp Thr Lys Val Leu Gln Asp
```

```
            305                 310                 315                 320
Leu Arg Tyr Glu Tyr Asp Pro Val Gly Asn Val Ile Ser Ile Arg Asn
                325                 330                 335
Asp Ala Glu Ala Thr Arg Phe Trp His Asn Gln Lys Val Met Pro Glu
            340                 345                 350
Asn Thr Tyr Thr Tyr Asp Ser Leu Tyr Gln Leu Ile Ser Ala Thr Gly
                355                 360                 365
Arg Glu Met Ala Asn Ile Gly Gln Gln Ser His Gln Phe Pro Ser Pro
        370                 375                 380
Ala Leu Pro Ser Asp Asn Asn Thr Tyr Thr Asn Tyr Thr Arg Thr Tyr
385                 390                 395                 400
Thr Tyr Asp Arg Gly Gly Asn Leu Thr Lys Ile Gln His Ser Ser Pro
                405                 410                 415
Ala Thr Gln Asn Asn Tyr Thr Thr Asn Ile Thr Val Ser Asn Arg Ser
            420                 425                 430
Asn Arg Ala Val Leu Ser Thr Leu Thr Glu Asp Pro Ala Gln Val Asp
        435                 440                 445
Ala Leu Phe Asp Ala Gly Gly His Gln Asn Thr Leu Ile Ser Gly Gln
450                 455                 460
Asn Leu Asn Trp Asn Thr Arg Gly Glu Leu Gln Gln Val Thr Leu Val
465                 470                 475                 480
Lys Arg Asp Lys Gly Ala Asn Asp Asp Arg Glu Trp Tyr Arg Tyr Ser
                485                 490                 495
Gly Asp Gly Arg Arg Met Leu Lys Ile Asn Glu Gln Gln Ala Ser Asn
            500                 505                 510
Asn Ala Gln Thr Gln Arg Val Thr Tyr Leu Pro Asn Leu Glu Leu Arg
        515                 520                 525
Leu Thr Gln Asn Ser Thr Ala Thr Thr Glu Asp Leu Gln Val Ile Thr
        530                 535                 540
Val Gly Glu Ala Gly Arg Ala Gln Val Arg Val Leu His Trp Glu Ser
545                 550                 555                 560
Gly Lys Pro Glu Asp Ile Asp Asn Asn Gln Leu Arg Tyr Ser Tyr Asp
                565                 570                 575
Asn Leu Ile Gly Ser Ser Gln Leu Glu Leu Asp Ser Glu Gly Gln Ile
            580                 585                 590
Ile Ser Glu Glu Glu Tyr Tyr Pro Tyr Gly Gly Thr Ala Leu Trp Ala
        595                 600                 605
Ala Arg Asn Gln Thr Glu Ala Ser Tyr Lys Thr Ile Arg Tyr Ser Gly
        610                 615                 620
Lys Glu Arg Asp Ala Thr Gly Leu Tyr Tyr Gly Tyr Arg Tyr Tyr
625                 630                 635                 640
Gln Pro Trp Ile Gly Arg Trp Leu Ser Ser Asp Pro Ala Gly Thr Ile
                645                 650                 655
Asp Gly Leu Asn Leu Tyr Arg Met Val Arg Asn Asn Pro Val Thr Leu
            660                 665                 670
Leu Asp Pro Asp Gly Leu Met Pro Thr Ile Ala Glu Arg Ile Ala Ala
        675                 680                 685
Leu Lys Lys Asn Lys Val Thr Asp Ser Ala Pro Ser Pro Ala Asn Ala
        690                 695                 700
Thr Asn Val Ala Ile Asn Ile Arg Pro Pro Val Ala Pro Lys Pro Ser
705                 710                 715                 720
Leu Pro Lys Ala Ser Thr Ser Ser Gln Pro Thr Thr His Pro Ile Gly
                725                 730                 735
```

-continued

```
Ala Ala Asn Ile Lys Pro Thr Thr Ser Gly Ser Ser Ile Val Ala Pro
            740                 745                 750
Leu Ser Pro Val Gly Asn Lys Ser Thr Ser Glu Ile Ser Leu Pro Glu
        755                 760                 765
Ser Ala Gln Ser Ser Ser Ser Thr Thr Ser Thr Asn Leu Gln Lys
    770                 775                 780
Lys Ser Phe Thr Leu Tyr Arg Ala Asp Asn Arg Ser Phe Glu Glu Met
785                 790                 795                 800
Gln Ser Lys Phe Pro Glu Gly Phe Lys Ala Trp Thr Pro Leu Asp Thr
                805                 810                 815
Lys Met Ala Arg Gln Phe Ala Ser Ile Phe Ile Gly Gln Lys Asp Thr
            820                 825                 830
Ser Asn Leu Pro Lys Glu Thr Val Lys Asn Ile Ser Thr Trp Gly Ala
        835                 840                 845
Lys Pro Lys Leu Lys Asp Leu Ser Asn Tyr Ile Lys Tyr Thr Lys Asp
    850                 855                 860
Lys Ser Thr Val Trp Val Ser Thr Ala Ile Asn Thr Glu Ala Gly Gly
865                 870                 875                 880
Gln Ser Ser Gly Ala Pro Leu His Lys Ile Asp Met Asp Leu Tyr Glu
                885                 890                 895
Phe Ala Ile Asp Gly Gln Lys Leu Asn Pro Leu Pro Glu Gly Arg Thr
            900                 905                 910
Lys Asn Met Val Pro Ser Leu Leu Leu Asp Thr Pro Gln Ile Glu Thr
        915                 920                 925
Ser Ser Ile Ile Ala Leu Asn His Gly Pro Val Asn Asp Ala Glu Ile
    930                 935                 940
Ser Phe Leu Thr Thr Ile Pro Leu Lys Asn Val Lys Pro His Lys Arg
945                 950                 955                 960
```

<210> SEQ ID NO 13
<211> LENGTH: 2850
<212> TYPE: DNA
<213> ORGANISM: Photorhabdus luminescens
<220> FEATURE:
<221> NAME/KEY: CDS
<222> LOCATION: (1)..(2847)

<400> SEQUENCE: 13

```
atg aaa aac att gac cca aaa ctt tat caa cat acg ccc acc gtt aac        48
Met Lys Asn Ile Asp Pro Lys Leu Tyr Gln His Thr Pro Thr Val Asn
1               5                   10                  15 gtc tac gat aac cgt ggc ctg acc att cgt aac atc gac ttt cac cgt        96
Val Tyr Asp Asn Arg Gly Leu Thr Ile Arg Asn Ile Asp Phe His Arg
                20                  25                  30 gac gtc gcg gga ggc gat aca gat act cgt att acc cgc cac caa tat       144
Asp Val Ala Gly Gly Asp Thr Asp Thr Arg Ile Thr Arg His Gln Tyr
            35                  40                  45 gat acc cga gga cac ttg agc caa agc att gat cca cgg ctg tat gac       192
Asp Thr Arg Gly His Leu Ser Gln Ser Ile Asp Pro Arg Leu Tyr Asp
        50                  55                  60 gcc aaa caa acc aat aac tcg aca aac ccc aac ttc ctc tgg caa tac       240
Ala Lys Gln Thr Asn Asn Ser Thr Asn Pro Asn Phe Leu Trp Gln Tyr
65                  70                  75                  80 aat ctc acc ggc gac act ttg cgg aca gaa agt gtc gat gcc ggc cgt       288
Asn Leu Thr Gly Asp Thr Leu Arg Thr Glu Ser Val Asp Ala Gly Arg
                85                  90                  95 acc gta gcc ctc aat gat att gaa ggc cgt caa gtg ttg att gta acc       336
Thr Val Ala Leu Asn Asp Ile Glu Gly Arg Gln Val Leu Ile Val Thr
```

```
                Thr Val Ala Leu Asn Asp Ile Glu Gly Arg Gln Val Leu Ile Val Thr
                                100                 105                 110 gca acc ggc gcc att cag acc cga caa tat gaa gcc aat acc ctg ccc          384
Ala Thr Gly Ala Ile Gln Thr Arg Gln Tyr Glu Ala Asn Thr Leu Pro
            115                 120                 125 ggt cgt cta tta tcc gta agt gaa caa gcc ccc gga gaa cag act ccc          432
Gly Arg Leu Leu Ser Val Ser Glu Gln Ala Pro Gly Glu Gln Thr Pro
130                 135                 140 cgc gtt act gag cat ttt att tgg gct ggt aat aca cag gcg gag aaa          480
Arg Val Thr Glu His Phe Ile Trp Ala Gly Asn Thr Gln Ala Glu Lys
145                 150                 155                 160 gat cat aat ctt gcc ggc cag tat gtg cgc cac tac gac aca gca gga          528
Asp His Asn Leu Ala Gly Gln Tyr Val Arg His Tyr Asp Thr Ala Gly
                165                 170                 175 gtg acg caa ctg gaa agc ctg tca ttg aca gaa aac atc tta tct caa          576
Val Thr Gln Leu Glu Ser Leu Ser Leu Thr Glu Asn Ile Leu Ser Gln
            180                 185                 190 tcc cgt cag tta tta gcc gac ggt cag gaa gca gac tgg aca ggt aac          624
Ser Arg Gln Leu Leu Ala Asp Gly Gln Glu Ala Asp Trp Thr Gly Asn
        195                 200                 205 gat gaa acc ctc tgg cag acc aaa ctc aat agc gaa act tac acg aca          672
Asp Glu Thr Leu Trp Gln Thr Lys Leu Asn Ser Glu Thr Tyr Thr Thr
    210                 215                 220 caa agc acc ttt gat gct acc ggc gct ttg ctg acc caa acc gat gca          720
Gln Ser Thr Phe Asp Ala Thr Gly Ala Leu Leu Thr Gln Thr Asp Ala
225                 230                 235                 240 aaa ggc aac atg caa cgt ctg gct tac aac gtg gca gga caa tta caa          768
Lys Gly Asn Met Gln Arg Leu Ala Tyr Asn Val Ala Gly Gln Leu Gln
                245                 250                 255 ggt agc tgg ctg aca ttg aaa aac caa agt gag caa gtc att gtc aaa          816
Gly Ser Trp Leu Thr Leu Lys Asn Gln Ser Glu Gln Val Ile Val Lys
            260                 265                 270 tcc ctg acc tat tcc gcc gca ggc cag aaa ttg cgt gaa gaa cac ggt          864
Ser Leu Thr Tyr Ser Ala Ala Gly Gln Lys Leu Arg Glu Glu His Gly
        275                 280                 285 aat ggc gtt atc act gaa tac agc tat gaa ccg gaa act cta cga ttg          912
Asn Gly Val Ile Thr Glu Tyr Ser Tyr Glu Pro Glu Thr Leu Arg Leu
    290                 295                 300 atc ggt acc act act cgc cgt caa tca gat agc aag gtg tta caa gat          960
Ile Gly Thr Thr Thr Arg Arg Gln Ser Asp Ser Lys Val Leu Gln Asp
305                 310                 315                 320 cta cgc tat gaa cat gat cct gta ggg aat att att agt gtc cgt aat         1008
Leu Arg Tyr Glu His Asp Pro Val Gly Asn Ile Ile Ser Val Arg Asn
                325                 330                 335 gat gca gaa gcc acc cgc ttc tgg cgc aat cag aaa ata gtc cct gaa         1056
Asp Ala Glu Ala Thr Arg Phe Trp Arg Asn Gln Lys Ile Val Pro Glu
            340                 345                 350 aat acc tac acc tac gat tcc ctg tat cag ctt atc agt gca aca gga         1104
Asn Thr Tyr Thr Tyr Asp Ser Leu Tyr Gln Leu Ile Ser Ala Thr Gly
        355                 360                 365 cgt gag atg gct aac atc ggc cag caa agc aac caa ctt cct tcg cca         1152
Arg Glu Met Ala Asn Ile Gly Gln Gln Ser Asn Gln Leu Pro Ser Pro
    370                 375                 380 atc atc cct ctt cct act gat gaa aac tca tat acc aac tat act cgc         1200
Ile Ile Pro Leu Pro Thr Asp Glu Asn Ser Tyr Thr Asn Tyr Thr Arg
385                 390                 395                 400 agc tat aat tac gat cgc ggc ggc aat ttg gtt caa atc cgg cac agt         1248
Ser Tyr Asn Tyr Asp Arg Gly Gly Asn Leu Val Gln Ile Arg His Ser
                405                 410                 415
```

```
tcc ccc gcc gcc caa aat aac tac acc aca gat atc acc gtt tcg aat      1296
Ser Pro Ala Ala Gln Asn Asn Tyr Thr Thr Asp Ile Thr Val Ser Asn
            420                 425                 430 cgc agt aac cgg gca gtg ctg agt tcg cta acc tca gac cca aca cag      1344
Arg Ser Asn Arg Ala Val Leu Ser Ser Leu Thr Ser Asp Pro Thr Gln
            435                 440                 445 gtg gag gca ctg ttt gat gcc ggc gga cat caa aca aaa ttg tta ccg      1392
Val Glu Ala Leu Phe Asp Ala Gly Gly His Gln Thr Lys Leu Leu Pro
450                 455                 460 ggg caa gag ctg agt tgg aat aca cga ggt gaa cta aaa cag gta acg      1440
Gly Gln Glu Leu Ser Trp Asn Thr Arg Gly Glu Leu Lys Gln Val Thr
465                 470                 475                 480 cca gtc agt cgc gag agc gcc agc gat cgg gaa tgg tat cgt tac ggc      1488
Pro Val Ser Arg Glu Ser Ala Ser Asp Arg Glu Trp Tyr Arg Tyr Gly
                485                 490                 495 aac gac ggc atg cga cgg tta aaa gtc agt gag caa cag act ggc aac      1536
Asn Asp Gly Met Arg Arg Leu Lys Val Ser Glu Gln Gln Thr Gly Asn
            500                 505                 510 agc acg cag cag caa cga gta act tat ctt ccc gat ctg gag cta cgt      1584
Ser Thr Gln Gln Gln Arg Val Thr Tyr Leu Pro Asp Leu Glu Leu Arg
            515                 520                 525 aca aca caa aat ggg act act aca tca gaa gac ctg cat gct att acc      1632
Thr Thr Gln Asn Gly Thr Thr Thr Ser Glu Asp Leu His Ala Ile Thr
530                 535                 540 gtg gga gca gca ggc cac gca caa gtg cga gtt cta cac tgg gaa act      1680
Val Gly Ala Ala Gly His Ala Gln Val Arg Val Leu His Trp Glu Thr
545                 550                 555                 560 acg cca cca gcc ggt atc aat aac aat cag ctt cgc tat agc tat gat      1728
Thr Pro Pro Ala Gly Ile Asn Asn Asn Gln Leu Arg Tyr Ser Tyr Asp
                565                 570                 575 aat ttg att ggt tcc agt caa ctt gaa ctg gat aac gca gga caa att      1776
Asn Leu Ile Gly Ser Ser Gln Leu Glu Leu Asp Asn Ala Gly Gln Ile
            580                 585                 590 atc agt cag gaa gag tat tat cca ttt ggc ggc aca gca tta tgg gca      1824
Ile Ser Gln Glu Glu Tyr Tyr Pro Phe Gly Gly Thr Ala Leu Trp Ala
            595                 600                 605 gca aga aac caa ata gaa gcc agc tac aaa atc ctc cgt tac tca ggt      1872
Ala Arg Asn Gln Ile Glu Ala Ser Tyr Lys Ile Leu Arg Tyr Ser Gly
610                 615                 620 aaa gaa cgc gat gct acc ggg ctc tat tat tac ggc tac cgc tat tat      1920
Lys Glu Arg Asp Ala Thr Gly Leu Tyr Tyr Tyr Gly Tyr Arg Tyr Tyr
625                 630                 635                 640 cag ccg tgg gtt ggt agg tgg tta agc gcc gat ccg gct gga aca atc      1968
Gln Pro Trp Val Gly Arg Trp Leu Ser Ala Asp Pro Ala Gly Thr Ile
                645                 650                 655 gat gga ctg aat cta tac cgg atg gtg aga aat aat ccg tca aca ctg      2016
Asp Gly Leu Asn Leu Tyr Arg Met Val Arg Asn Asn Pro Ser Thr Leu
            660                 665                 670 gtt gat att tct ggg ctt gca cct acg aaa tac aat att ccc gga ttt      2064
Val Asp Ile Ser Gly Leu Ala Pro Thr Lys Tyr Asn Ile Pro Gly Phe
            675                 680                 685 gac ttt gat gta gaa ata gat gag caa aaa aga tct aaa tta aaa cca      2112
Asp Phe Asp Val Glu Ile Asp Glu Gln Lys Arg Ser Lys Leu Lys Pro
690                 695                 700 acg ttg ata aga atc aaa gat gaa ttt tta cat tat ggt cct gta gat      2160
Thr Leu Ile Arg Ile Lys Asp Glu Phe Leu His Tyr Gly Pro Val Asp
705                 710                 715                 720 aag ctg tta gaa gaa aaa aaa ccc ggc ctc aat gta cca gag gag cta      2208
Lys Leu Leu Glu Glu Lys Lys Pro Gly Leu Asn Val Pro Glu Glu Leu
                725                 730                 735
```

-continued

| | | |
|---|---|---|
| ttt gat aga ggt cca tcc gag aat gga gtg tca aca tta act ttc aaa<br>Phe Asp Arg Gly Pro Ser Glu Asn Gly Val Ser Thr Leu Thr Phe Lys<br>            740                    745                    750 | | 2256 |
| aaa gac cta ccg ata agt tgt att agc aac aca gaa tat acc ctt gat<br>Lys Asp Leu Pro Ile Ser Cys Ile Ser Asn Thr Glu Tyr Thr Leu Asp<br>            755                    760                    765 | | 2304 |
| atc tta tac aac aaa cat gag act aaa cca ttc cct tac gaa aac gaa<br>Ile Leu Tyr Asn Lys His Glu Thr Lys Pro Phe Pro Tyr Glu Asn Glu<br>770                    775                    780 | | 2352 |
| gca aca gtt ggc gca gat ctg gga gta ata atg tcc gtg gag ttt gga<br>Ala Thr Val Gly Ala Asp Leu Gly Val Ile Met Ser Val Glu Phe Gly<br>785                    790                    795                    800 | | 2400 |
| aat aaa tca ata ggt aat gcc tct gac gaa gat tta aaa gaa gaa cat<br>Asn Lys Ser Ile Gly Asn Ala Ser Asp Glu Asp Leu Lys Glu Glu His<br>                    805                    810                    815 | | 2448 |
| ctc cca tta gga aaa tcc aca atg gat aaa aca gac ctg cca gat tta<br>Leu Pro Leu Gly Lys Ser Thr Met Asp Lys Thr Asp Leu Pro Asp Leu<br>            820                    825                    830 | | 2496 |
| aaa caa ggg cta atg atc gcg gag aag ata aaa agt gga aaa ggg gca<br>Lys Gln Gly Leu Met Ile Ala Glu Lys Ile Lys Ser Gly Lys Gly Ala<br>835                    840                    845 | | 2544 |
| tat cct ttt cat ttt ggt gct gca ata gct gtt gta tat ggt gag gat<br>Tyr Pro Phe His Phe Gly Ala Ala Ile Ala Val Val Tyr Gly Glu Asp<br>850                    855                    860 | | 2592 |
| aaa aaa gta gcc gct tca att ctg aca gat tta tct gaa cct aaa aga<br>Lys Lys Val Ala Ala Ser Ile Leu Thr Asp Leu Ser Glu Pro Lys Arg<br>865                    870                    875                    880 | | 2640 |
| gac gaa ggc gag tat ttg caa agt acg aga aag gta agc gca atg ttt<br>Asp Glu Gly Glu Tyr Leu Gln Ser Thr Arg Lys Val Ser Ala Met Phe<br>                    885                    890                    895 | | 2688 |
| atc aca aac gtc aat gaa ttt cgc ggc cat gat tac cca aaa agt aaa<br>Ile Thr Asn Val Asn Glu Phe Arg Gly His Asp Tyr Pro Lys Ser Lys<br>            900                    905                    910 | | 2736 |
| tat agt atc gga tta gtt aca gct gaa aaa cgt cag cca gta ata agc<br>Tyr Ser Ile Gly Leu Val Thr Ala Glu Lys Arg Gln Pro Val Ile Ser<br>            915                    920                    925 | | 2784 |
| aaa aaa cgt gca aac ccg gaa gag gcc cct tca tca tcc aga aat aaa<br>Lys Lys Arg Ala Asn Pro Glu Glu Ala Pro Ser Ser Ser Arg Asn Lys<br>930                    935                    940 | | 2832 |
| aaa ttg cat gta cat taa<br>Lys Leu His Val His<br>945 | | 2850 |

<210> SEQ ID NO 14
<211> LENGTH: 949
<212> TYPE: PRT
<213> ORGANISM: Photorhabdus luminescens

<400> SEQUENCE: 14

Met Lys Asn Ile Asp Pro Lys Leu Tyr Gln His Thr Pro Thr Val Asn
1                  5                    10                    15

Val Tyr Asp Asn Arg Gly Leu Thr Ile Arg Asn Ile Asp Phe His Arg
                  20                    25                    30

Asp Val Ala Gly Gly Asp Thr Asp Thr Arg Ile Thr Arg His Gln Tyr
                        35                    40                    45

Asp Thr Arg Gly His Leu Ser Gln Ser Ile Asp Pro Arg Leu Tyr Asp
        50                    55                    60

Ala Lys Gln Thr Asn Asn Ser Thr Asn Pro Asn Phe Leu Trp Gln Tyr
65                    70                    75                    80

-continued

Asn Leu Thr Gly Asp Thr Leu Arg Thr Glu Ser Val Asp Ala Gly Arg
                85                  90                  95
Thr Val Ala Leu Asn Asp Ile Glu Gly Arg Gln Val Leu Ile Val Thr
            100                 105                 110
Ala Thr Gly Ala Ile Gln Thr Arg Gln Tyr Glu Ala Asn Thr Leu Pro
            115                 120                 125
Gly Arg Leu Leu Ser Val Ser Glu Gln Ala Pro Gly Glu Gln Thr Pro
        130                 135                 140
Arg Val Thr Glu His Phe Ile Trp Ala Gly Asn Thr Gln Ala Glu Lys
145                 150                 155                 160
Asp His Asn Leu Ala Gly Gln Tyr Val Arg His Tyr Asp Thr Ala Gly
                165                 170                 175
Val Thr Gln Leu Glu Ser Leu Ser Leu Thr Glu Asn Ile Leu Ser Gln
            180                 185                 190
Ser Arg Gln Leu Leu Ala Asp Gly Gln Glu Ala Asp Trp Thr Gly Asn
        195                 200                 205
Asp Glu Thr Leu Trp Gln Thr Lys Leu Asn Ser Glu Thr Tyr Thr Thr
210                 215                 220
Gln Ser Thr Phe Asp Ala Thr Gly Ala Leu Leu Thr Gln Thr Asp Ala
225                 230                 235                 240
Lys Gly Asn Met Gln Arg Leu Ala Tyr Asn Val Ala Gly Gln Leu Gln
                245                 250                 255
Gly Ser Trp Leu Thr Leu Lys Asn Gln Ser Glu Gln Val Ile Val Lys
            260                 265                 270
Ser Leu Thr Tyr Ser Ala Ala Gly Gln Lys Leu Arg Glu Glu His Gly
        275                 280                 285
Asn Gly Val Ile Thr Glu Tyr Ser Tyr Glu Pro Glu Thr Leu Arg Leu
        290                 295                 300
Ile Gly Thr Thr Thr Arg Arg Gln Ser Asp Ser Lys Val Leu Gln Asp
305                 310                 315                 320
Leu Arg Tyr Glu His Asp Pro Val Gly Asn Ile Ile Ser Val Arg Asn
                325                 330                 335
Asp Ala Glu Ala Thr Arg Phe Trp Arg Asn Gln Lys Ile Val Pro Glu
            340                 345                 350
Asn Thr Tyr Thr Tyr Asp Ser Leu Tyr Gln Leu Ile Ser Ala Thr Gly
        355                 360                 365
Arg Glu Met Ala Asn Ile Gly Gln Gln Ser Asn Gln Leu Pro Ser Pro
        370                 375                 380
Ile Ile Pro Leu Pro Thr Asp Glu Asn Ser Tyr Thr Asn Tyr Thr Arg
385                 390                 395                 400
Ser Tyr Asn Tyr Asp Arg Gly Gly Asn Leu Val Gln Ile Arg His Ser
                405                 410                 415
Ser Pro Ala Ala Gln Asn Asn Tyr Thr Thr Asp Ile Thr Val Ser Asn
            420                 425                 430
Arg Ser Asn Arg Ala Val Leu Ser Ser Leu Thr Ser Asp Pro Thr Gln
        435                 440                 445
Val Glu Ala Leu Phe Asp Ala Gly His Gln Thr Lys Leu Leu Pro
        450                 455                 460
Gly Gln Glu Leu Ser Trp Asn Thr Arg Gly Leu Lys Gln Val Thr
465                 470                 475                 480
Pro Val Ser Arg Glu Ser Ala Ser Asp Arg Glu Trp Tyr Arg Tyr Gly
                485                 490                 495

```
Asn Asp Gly Met Arg Arg Leu Lys Val Ser Glu Gln Gln Thr Gly Asn
            500                 505                 510
Ser Thr Gln Gln Gln Arg Val Thr Tyr Leu Pro Asp Leu Glu Leu Arg
            515                 520                 525
Thr Thr Gln Asn Gly Thr Thr Thr Ser Glu Asp Leu His Ala Ile Thr
            530                 535                 540
Val Gly Ala Ala Gly His Ala Gln Val Arg Val Leu His Trp Glu Thr
545                 550                 555                 560
Thr Pro Pro Ala Gly Ile Asn Asn Gln Leu Arg Tyr Ser Tyr Asp
                565                 570                 575
Asn Leu Ile Gly Ser Ser Gln Leu Glu Leu Asp Asn Ala Gly Gln Ile
                580                 585                 590
Ile Ser Gln Glu Glu Tyr Tyr Pro Phe Gly Gly Thr Ala Leu Trp Ala
            595                 600                 605
Ala Arg Asn Gln Ile Glu Ala Ser Tyr Lys Ile Leu Arg Tyr Ser Gly
            610                 615                 620
Lys Glu Arg Asp Ala Thr Gly Leu Tyr Tyr Gly Tyr Arg Tyr Tyr
625                 630                 635                 640
Gln Pro Trp Val Gly Arg Trp Leu Ser Ala Asp Pro Ala Gly Thr Ile
                645                 650                 655
Asp Gly Leu Asn Leu Tyr Arg Met Val Arg Asn Asn Pro Ser Thr Leu
                660                 665                 670
Val Asp Ile Ser Gly Leu Ala Pro Thr Lys Tyr Asn Ile Pro Gly Phe
            675                 680                 685
Asp Phe Asp Val Glu Ile Asp Glu Gln Lys Arg Ser Lys Leu Lys Pro
            690                 695                 700
Thr Leu Ile Arg Ile Lys Asp Glu Phe Leu His Tyr Gly Pro Val Asp
705                 710                 715                 720
Lys Leu Leu Glu Glu Lys Lys Pro Gly Leu Asn Val Pro Glu Leu
                725                 730                 735
Phe Asp Arg Gly Pro Ser Glu Asn Gly Val Ser Thr Leu Thr Phe Lys
                740                 745                 750
Lys Asp Leu Pro Ile Ser Cys Ile Ser Asn Thr Glu Tyr Thr Leu Asp
            755                 760                 765
Ile Leu Tyr Asn Lys His Glu Thr Lys Pro Phe Pro Tyr Glu Asn Glu
            770                 775                 780
Ala Thr Val Gly Ala Asp Leu Gly Val Ile Met Ser Val Glu Phe Gly
785                 790                 795                 800
Asn Lys Ser Ile Gly Asn Ala Ser Asp Glu Asp Leu Lys Glu Glu His
                805                 810                 815
Leu Pro Leu Gly Lys Ser Thr Met Asp Lys Thr Asp Leu Pro Asp Leu
                820                 825                 830
Lys Gln Gly Leu Met Ile Ala Glu Lys Ile Lys Ser Gly Lys Gly Ala
            835                 840                 845
Tyr Pro Phe His Phe Gly Ala Ala Ile Ala Val Val Tyr Gly Glu Asp
            850                 855                 860
Lys Lys Val Ala Ala Ser Ile Leu Thr Asp Leu Ser Glu Pro Lys Arg
865                 870                 875                 880
Asp Glu Gly Glu Tyr Leu Gln Ser Thr Arg Lys Val Ser Ala Met Phe
                885                 890                 895
Ile Thr Asn Val Asn Glu Phe Arg Gly His Asp Tyr Pro Lys Ser Lys
                900                 905                 910
Tyr Ser Ile Gly Leu Val Thr Ala Glu Lys Arg Gln Pro Val Ile Ser
```

```
                915                 920                 925
Lys Lys Arg Ala Asn Pro Glu Glu Ala Pro Ser Ser Ser Arg Asn Lys
        930                 935                 940

Lys Leu His Val His
945

<210> SEQ ID NO 15
<211> LENGTH: 2817
<212> TYPE: DNA
<213> ORGANISM: Photorhabdus luminescens
<220> FEATURE:
<221> NAME/KEY: CDS
<222> LOCATION: (1)..(2814)

<400> SEQUENCE: 15 atg gaa aac att gac cca aaa ctt tat cac cat acg cct acc gtc agt      48
Met Glu Asn Ile Asp Pro Lys Leu Tyr His His Thr Pro Thr Val Ser
1               5                   10                  15 gtt cac gat aac cgt gga cta gct atc cgt aat att agt ttt cac cgc      96
Val His Asp Asn Arg Gly Leu Ala Ile Arg Asn Ile Ser Phe His Arg
            20                  25                  30 act acc gca gaa gca aat acc gat acc cgt att acc cgc cat caa tat     144
Thr Thr Ala Glu Ala Asn Thr Asp Thr Arg Ile Thr Arg His Gln Tyr
        35                  40                  45 aat gcc ggc gga tat ttg aac caa agc att gat cct cgc ctg tat gac     192
Asn Ala Gly Gly Tyr Leu Asn Gln Ser Ile Asp Pro Arg Leu Tyr Asp
    50                  55                  60 gcc aaa cag act aac aac gct gta caa ccg aat ttt atc tgg cga cat     240
Ala Lys Gln Thr Asn Asn Ala Val Gln Pro Asn Phe Ile Trp Arg His
65                  70                  75                  80 aat ttg acc ggc aat atc ctg cga aca gag agc gtc gat gcc ggt cgg     288
Asn Leu Thr Gly Asn Ile Leu Arg Thr Glu Ser Val Asp Ala Gly Arg
                85                  90                  95 acg att acc ctc aac gat att gaa ggc cgc ccg gtg ttg acc atc aat     336
Thr Ile Thr Leu Asn Asp Ile Glu Gly Arg Pro Val Leu Thr Ile Asn
            100                 105                 110 gca gcc ggt gtc cgg caa aac cat cgc tac gaa gat aac acc ctg ccc     384
Ala Ala Gly Val Arg Gln Asn His Arg Tyr Glu Asp Asn Thr Leu Pro
        115                 120                 125 ggt cgc ctg ctc gct atc agc gaa caa gga cag gca gaa gag aaa acg     432
Gly Arg Leu Leu Ala Ile Ser Glu Gln Gly Gln Ala Glu Glu Lys Thr
    130                 135                 140 acc gag cgc ctt atc tgg gcc ggc aat acg ccg caa gaa aaa gac cac     480
Thr Glu Arg Leu Ile Trp Ala Gly Asn Thr Pro Gln Glu Lys Asp His
145                 150                 155                 160 aac ctt gcc ggt cag tgc gtc cgc cat tac gat acc gca gga ctc act     528
Asn Leu Ala Gly Gln Cys Val Arg His Tyr Asp Thr Ala Gly Leu Thr
                165                 170                 175 caa ctc aac agc ctt gcc ctg acc ggc gcc gtt cta tca caa tct caa     576
Gln Leu Asn Ser Leu Ala Leu Thr Gly Ala Val Leu Ser Gln Ser Gln
            180                 185                 190 caa ctg ctt acc gat aac cag gat gcc gac tgg aca ggt gaa gac cag     624
Gln Leu Leu Thr Asp Asn Gln Asp Ala Asp Trp Thr Gly Glu Asp Gln
        195                 200                 205 agc ctc tgg caa caa aaa ctg agt agt gat gtc tat atc acc caa agt     672
Ser Leu Trp Gln Gln Lys Leu Ser Ser Asp Val Tyr Ile Thr Gln Ser
    210                 215                 220 aac act gat gcc acc ggg gct tta ctg acc cag acc gat gcc aaa ggc     720
Asn Thr Asp Ala Thr Gly Ala Leu Leu Thr Gln Thr Asp Ala Lys Gly
225                 230                 235                 240
```

-continued

| | |
|---|---|
| aac att cag cgg ctg gcc tat gat gtg gcc ggg cag cta aaa ggg agt<br>Asn Ile Gln Arg Leu Ala Tyr Asp Val Ala Gly Gln Leu Lys Gly Ser<br>245                        250                       255 | 768 |
| tgg tta aca ctc aaa ggt cag gcg gaa cag gtg att atc aaa tcg cta<br>Trp Leu Thr Leu Lys Gly Gln Ala Glu Gln Val Ile Ile Lys Ser Leu<br>260                        265                       270 | 816 |
| acc tac tcc gcc gcc ggg caa aaa tta cgt gaa gag cac ggt aac ggg<br>Thr Tyr Ser Ala Ala Gly Gln Lys Leu Arg Glu Glu His Gly Asn Gly<br>275                        280                       285 | 864 |
| att gtc act gaa tac agc tac gaa ccg gaa acc caa cgg ctt atc ggc<br>Ile Val Thr Glu Tyr Ser Tyr Glu Pro Glu Thr Gln Arg Leu Ile Gly<br>290                        295                       300 | 912 |
| att acc act cgc cgt cca tca gac gcc aag gtg ttg caa gac cta cgc<br>Ile Thr Thr Arg Arg Pro Ser Asp Ala Lys Val Leu Gln Asp Leu Arg<br>305                       310                      315                      320 | 960 |
| tat caa tat gac cca gta ggc aat gtc att agt atc cgt aat gat gcg<br>Tyr Gln Tyr Asp Pro Val Gly Asn Val Ile Ser Ile Arg Asn Asp Ala<br>                       325                       330                       335 | 1008 |
| gaa gcc act cgc ttt tgg cgc aat cag aaa gta gcc ccg gag aat agc<br>Glu Ala Thr Arg Phe Trp Arg Asn Gln Lys Val Ala Pro Glu Asn Ser<br>                       340                       345                       350 | 1056 |
| tat acc tac gat tcc ctg tat cag ctt atc agc gcc acc ggg cgc gag<br>Tyr Thr Tyr Asp Ser Leu Tyr Gln Leu Ile Ser Ala Thr Gly Arg Glu<br>                       355                       360                       365 | 1104 |
| atg gcc aat atc ggt cag caa agc aac caa ctt ccc tct ccg gcg cta<br>Met Ala Asn Ile Gly Gln Gln Ser Asn Gln Leu Pro Ser Pro Ala Leu<br>370                        375                       380 | 1152 |
| cct tct gat aac aat acc tac acc aac tat act cgc act tat act tat<br>Pro Ser Asp Asn Asn Thr Tyr Thr Asn Tyr Thr Arg Thr Tyr Thr Tyr<br>385                       390                       395                     400 | 1200 |
| gac cgt ggc ggc aat ttg acg aaa att cag cat agt tca cca gcc gcg<br>Asp Arg Gly Gly Asn Leu Thr Lys Ile Gln His Ser Ser Pro Ala Ala<br>                       405                       410                       415 | 1248 |
| caa aat aac tac acg acg gat ata acg gtt tca aat cgc agc aac cgc<br>Gln Asn Asn Tyr Thr Thr Asp Ile Thr Val Ser Asn Arg Ser Asn Arg<br>                       420                       425                       430 | 1296 |
| gcg gta ctc agc aca ttg acc gca gat cca act caa gtc gat gcc tta<br>Ala Val Leu Ser Thr Leu Thr Ala Asp Pro Thr Gln Val Asp Ala Leu<br>                       435                       440                       445 | 1344 |
| ttt gat gcg gga ggc cat caa acc agc ttg tta tcc ggc caa gtt cta<br>Phe Asp Ala Gly Gly His Gln Thr Ser Leu Leu Ser Gly Gln Val Leu<br>450                        455                       460 | 1392 |
| act tgg aca ccg cga ggc gaa ttg aaa caa gcc aac aat agc gca gga<br>Thr Trp Thr Pro Arg Gly Glu Leu Lys Gln Ala Asn Asn Ser Ala Gly<br>465                        470                       475                       480 | 1440 |
| aat gag tgg tat cgc tac gat agc aac ggc ata cgc cag cta aaa gtg<br>Asn Glu Trp Tyr Arg Tyr Asp Ser Asn Gly Ile Arg Gln Leu Lys Val<br>                       485                       490                       495 | 1488 |
| aat gaa caa caa act cag aat atc ccg caa caa caa agg gta act tat<br>Asn Glu Gln Gln Thr Gln Asn Ile Pro Gln Gln Gln Arg Val Thr Tyr<br>                       500                       505                       510 | 1536 |
| cta ccg ggg ctg gaa ata cgt aca acc cag aac aac gcc aca aca aca<br>Leu Pro Gly Leu Glu Ile Arg Thr Thr Gln Asn Asn Ala Thr Thr Thr<br>                       515                       520                       525 | 1584 |
| gaa gag tta cac gtt atc aca ctc ggt aaa gcc ggc cgc gcg caa gtc<br>Glu Glu Leu His Val Ile Thr Leu Gly Lys Ala Gly Arg Ala Gln Val<br>                       530                       535                       540 | 1632 |
| cga gta ttg cat tgg gag agc ggt aaa cca gaa gat att aat aac aat<br>Arg Val Leu His Trp Glu Ser Gly Lys Pro Glu Asp Ile Asn Asn Asn<br>545                        550                       555                       560 | 1680 |

-continued

| | |
|---|---|
| cag ctt cgt tac agc tac gat aat ctt att ggc tcc agc caa ctt caa<br>Gln Leu Arg Tyr Ser Tyr Asp Asn Leu Ile Gly Ser Ser Gln Leu Gln<br>565                         570                         575 | 1728 |
| tta gat agc gac gga caa att atc agt gaa gaa gaa tat tat cca ttt<br>Leu Asp Ser Asp Gly Gln Ile Ile Ser Glu Glu Glu Tyr Tyr Pro Phe<br>580                         585                         590 | 1776 |
| ggt ggt aca gcg ctg tgg gcg gca agg aat caa acc gaa gcc agc tat<br>Gly Gly Thr Ala Leu Trp Ala Ala Arg Asn Gln Thr Glu Ala Ser Tyr<br>595                         600                         605 | 1824 |
| aaa acc att cgt tat tct ggt aaa gag cgg gat gtt acc ggg ctg tat<br>Lys Thr Ile Arg Tyr Ser Gly Lys Glu Arg Asp Val Thr Gly Leu Tyr<br>610                         615                         620 | 1872 |
| tat tat ggc tac cgt tat tac caa ccg tgg gcg ggc aga tgg tta ggt<br>Tyr Tyr Gly Tyr Arg Tyr Tyr Gln Pro Trp Ala Gly Arg Trp Leu Gly<br>625                         630                         635                         640 | 1920 |
| gca gac ccg gca gga acc att gat gga ctg aat tta tat cgc atg gtg<br>Ala Asp Pro Ala Gly Thr Ile Asp Gly Leu Asn Leu Tyr Arg Met Val<br>645                         650                         655 | 1968 |
| aga aat aac ccg gtg acg caa ttt gat gtt cag gga tta tca ccg gcc<br>Arg Asn Asn Pro Val Thr Gln Phe Asp Val Gln Gly Leu Ser Pro Ala<br>660                         665                         670 | 2016 |
| aac aga aca gaa gaa gcg ata ata aaa cag ggt tcc ttt acg gga atg<br>Asn Arg Thr Glu Glu Ala Ile Ile Lys Gln Gly Ser Phe Thr Gly Met<br>675                         680                         685 | 2064 |
| gaa gaa gct gtt tat aaa aaa atg gct aaa cct caa act ttc aaa cgc<br>Glu Glu Ala Val Tyr Lys Lys Met Ala Lys Pro Gln Thr Phe Lys Arg<br>690                         695                         700 | 2112 |
| caa aga gct atc gct gcc caa aca gag caa gaa gcc cat gaa tca ttg<br>Gln Arg Ala Ile Ala Ala Gln Thr Glu Gln Glu Ala His Glu Ser Leu<br>705                         710                         715                         720 | 2160 |
| acc aac aac cct agt gta gat att agc cca att aaa aac tac acc aca<br>Thr Asn Asn Pro Ser Val Asp Ile Ser Pro Ile Lys Asn Tyr Thr Thr<br>725                         730                         735 | 2208 |
| gat agc tca caa att aat gcc gcg ata agg gaa aat cgt att acg cca<br>Asp Ser Ser Gln Ile Asn Ala Ala Ile Arg Glu Asn Arg Ile Thr Pro<br>740                         745                         750 | 2256 |
| gca gtg gaa agt tta gac gcc aca tta tct tcc cta caa gat aga caa<br>Ala Val Glu Ser Leu Asp Ala Thr Leu Ser Ser Leu Gln Asp Arg Gln<br>755                         760                         765 | 2304 |
| atg agg gta act tat cgg gtg atg acc tat gta gat aat tcc acg cca<br>Met Arg Val Thr Tyr Arg Val Met Thr Tyr Val Asp Asn Ser Thr Pro<br>770                         775                         780 | 2352 |
| tcg cct tgg cac tcg cca cag gaa gga aat agt att aat gtt ggt gat<br>Ser Pro Trp His Ser Pro Gln Glu Gly Asn Ser Ile Asn Val Gly Asp<br>785                         790                         795                         800 | 2400 |
| atc gtt tcg gat aac gct tat tta tca aca tcg gcc cat cgt ggt ttt<br>Ile Val Ser Asp Asn Ala Tyr Leu Ser Thr Ser Ala His Arg Gly Phe<br>805                         810                         815 | 2448 |
| ctg aat ttt gtt cac aaa aaa gaa acc agt gaa act cga tac gtc aag<br>Leu Asn Phe Val His Lys Lys Glu Thr Ser Glu Thr Arg Tyr Val Lys<br>820                         825                         830 | 2496 |
| atg gca ttt tta acg aat gcg ggt gtc aat gtc cca gca gca tct atg<br>Met Ala Phe Leu Thr Asn Ala Gly Val Asn Val Pro Ala Ala Ser Met<br>835                         840                         845 | 2544 |
| tat aat aat gct ggc gag gag caa gta ttt aaa atg gat tta aac gat<br>Tyr Asn Asn Ala Gly Glu Glu Gln Val Phe Lys Met Asp Leu Asn Asp<br>850                         855                         860 | 2592 |
| tca aga aaa agc ctt gct gaa aaa tta aaa cta aga gtc agt gga cca<br>Ser Arg Lys Ser Leu Ala Glu Lys Leu Lys Leu Arg Val Ser Gly Pro | 2640 |

```
                865                 870                 875                 880
caa tcg gga caa gcg gaa ata tta cta cct agg gaa aca cag ttc gaa              2688
Gln Ser Gly Gln Ala Glu Ile Leu Leu Pro Arg Glu Thr Gln Phe Glu
                    885                 890                 895 gtt gtt tca atg aaa cat caa ggc aga gat acc tat gta tta ttg caa              2736
Val Val Ser Met Lys His Gln Gly Arg Asp Thr Tyr Val Leu Leu Gln
                900                 905                 910 gat att aac caa tcc gca gcc act cat aga aat gta cgt aac act tac              2784
Asp Ile Asn Gln Ser Ala Ala Thr His Arg Asn Val Arg Asn Thr Tyr
            915                 920                 925 acc ggt aat ttc aaa tca tcc agt gca aat taa                                  2817
Thr Gly Asn Phe Lys Ser Ser Ser Ala Asn
        930                 935

<210> SEQ ID NO 16
<211> LENGTH: 938
<212> TYPE: PRT
<213> ORGANISM: Photorhabdus luminescens

<400> SEQUENCE: 16

Met Glu Asn Ile Asp Pro Lys Leu Tyr His His Thr Pro Thr Val Ser
1               5                   10                  15

Val His Asp Asn Arg Gly Leu Ala Ile Arg Asn Ile Ser Phe His Arg
                20                  25                  30

Thr Thr Ala Glu Ala Asn Thr Asp Thr Arg Ile Thr Arg His Gln Tyr
            35                  40                  45

Asn Ala Gly Gly Tyr Leu Asn Gln Ser Ile Asp Pro Arg Leu Tyr Asp
        50                  55                  60

Ala Lys Gln Thr Asn Asn Ala Val Gln Pro Asn Phe Ile Trp Arg His
65                  70                  75                  80

Asn Leu Thr Gly Asn Ile Leu Arg Thr Glu Ser Val Asp Ala Gly Arg
                85                  90                  95

Thr Ile Thr Leu Asn Asp Ile Glu Gly Arg Pro Val Leu Thr Ile Asn
            100                 105                 110

Ala Ala Gly Val Arg Gln Asn His Arg Tyr Glu Asp Asn Thr Leu Pro
        115                 120                 125

Gly Arg Leu Leu Ala Ile Ser Glu Gln Gly Gln Ala Glu Glu Lys Thr
    130                 135                 140

Thr Glu Arg Leu Ile Trp Ala Gly Asn Thr Pro Gln Glu Lys Asp His
145                 150                 155                 160

Asn Leu Ala Gly Gln Cys Val Arg His Tyr Asp Thr Ala Gly Leu Thr
                165                 170                 175

Gln Leu Asn Ser Leu Ala Leu Thr Gly Ala Val Leu Ser Gln Ser Gln
            180                 185                 190

Gln Leu Leu Thr Asp Asn Gln Asp Ala Asp Trp Thr Gly Glu Asp Gln
        195                 200                 205

Ser Leu Trp Gln Gln Lys Leu Ser Ser Asp Val Tyr Ile Thr Gln Ser
    210                 215                 220

Asn Thr Asp Ala Thr Gly Ala Leu Leu Thr Gln Thr Asp Ala Lys Gly
225                 230                 235                 240

Asn Ile Gln Arg Leu Ala Tyr Asp Val Ala Gly Gln Leu Lys Gly Ser
                245                 250                 255

Trp Leu Thr Leu Lys Gly Gln Ala Glu Gln Val Ile Ile Lys Ser Leu
            260                 265                 270

Thr Tyr Ser Ala Ala Gly Gln Lys Leu Arg Glu Glu His Gly Asn Gly
        275                 280                 285
```

```
Ile Val Thr Glu Tyr Ser Tyr Glu Pro Glu Thr Gln Arg Leu Ile Gly
290                 295                 300

Ile Thr Thr Arg Arg Pro Ser Asp Ala Lys Val Leu Gln Asp Leu Arg
305                 310                 315                 320

Tyr Gln Tyr Asp Pro Val Gly Asn Val Ile Ser Ile Arg Asn Asp Ala
                325                 330                 335

Glu Ala Thr Arg Phe Trp Arg Asn Gln Lys Val Ala Pro Glu Asn Ser
                340                 345                 350

Tyr Thr Tyr Asp Ser Leu Tyr Gln Leu Ile Ser Ala Thr Gly Arg Glu
            355                 360                 365

Met Ala Asn Ile Gly Gln Gln Ser Asn Gln Leu Pro Ser Pro Ala Leu
370                 375                 380

Pro Ser Asp Asn Asn Thr Tyr Thr Asn Tyr Thr Arg Thr Tyr Thr Tyr
385                 390                 395                 400

Asp Arg Gly Gly Asn Leu Thr Lys Ile Gln His Ser Ser Pro Ala Ala
                405                 410                 415

Gln Asn Asn Tyr Thr Thr Asp Ile Thr Val Ser Asn Arg Ser Asn Arg
                420                 425                 430

Ala Val Leu Ser Thr Leu Thr Ala Asp Pro Thr Gln Val Asp Ala Leu
            435                 440                 445

Phe Asp Ala Gly His Gln Thr Ser Leu Leu Ser Gly Gln Val Leu
450                 455                 460

Thr Trp Thr Pro Arg Gly Glu Leu Lys Gln Ala Asn Asn Ser Ala Gly
465                 470                 475                 480

Asn Glu Trp Tyr Arg Tyr Asp Ser Asn Gly Ile Arg Gln Leu Lys Val
                485                 490                 495

Asn Glu Gln Gln Thr Gln Asn Ile Pro Gln Gln Arg Val Thr Tyr
                500                 505                 510

Leu Pro Gly Leu Glu Ile Arg Thr Thr Gln Asn Asn Ala Thr Thr Thr
            515                 520                 525

Glu Glu Leu His Val Ile Thr Leu Gly Lys Ala Gly Arg Ala Gln Val
530                 535                 540

Arg Val Leu His Trp Glu Ser Gly Lys Pro Glu Asp Ile Asn Asn Asn
545                 550                 555                 560

Gln Leu Arg Tyr Ser Tyr Asp Asn Leu Ile Gly Ser Ser Gln Leu Gln
                565                 570                 575

Leu Asp Ser Asp Gly Gln Ile Ile Ser Glu Glu Glu Tyr Tyr Pro Phe
            580                 585                 590

Gly Gly Thr Ala Leu Trp Ala Ala Arg Asn Gln Thr Glu Ala Ser Tyr
            595                 600                 605

Lys Thr Ile Arg Tyr Ser Gly Lys Glu Arg Asp Val Thr Gly Leu Tyr
            610                 615                 620

Tyr Tyr Gly Tyr Arg Tyr Tyr Gln Pro Trp Ala Gly Arg Trp Leu Gly
625                 630                 635                 640

Ala Asp Pro Ala Gly Thr Ile Asp Gly Leu Asn Leu Tyr Arg Met Val
                645                 650                 655

Arg Asn Asn Pro Val Thr Gln Phe Asp Val Gln Gly Leu Ser Pro Ala
                660                 665                 670

Asn Arg Thr Glu Glu Ala Ile Ile Lys Gln Gly Ser Phe Thr Gly Met
            675                 680                 685

Glu Glu Ala Val Tyr Lys Lys Met Ala Lys Pro Gln Thr Phe Lys Arg
690                 695                 700
```

-continued

```
Gln Arg Ala Ile Ala Ala Gln Thr Glu Gln Glu Ala His Glu Ser Leu
705                 710                 715                 720

Thr Asn Asn Pro Ser Val Asp Ile Ser Pro Ile Lys Asn Tyr Thr Thr
                725                 730                 735

Asp Ser Ser Gln Ile Asn Ala Ala Ile Arg Glu Asn Arg Ile Thr Pro
            740                 745                 750

Ala Val Glu Ser Leu Asp Ala Thr Leu Ser Ser Leu Gln Asp Arg Gln
            755                 760                 765

Met Arg Val Thr Tyr Arg Val Met Thr Tyr Val Asp Asn Ser Thr Pro
        770                 775                 780

Ser Pro Trp His Ser Pro Gln Glu Gly Asn Ser Ile Asn Val Gly Asp
785             790                 795                 800

Ile Val Ser Asp Asn Ala Tyr Leu Ser Thr Ser Ala His Arg Gly Phe
                805                 810                 815

Leu Asn Phe Val His Lys Lys Glu Thr Ser Glu Thr Arg Tyr Val Lys
            820                 825                 830

Met Ala Phe Leu Thr Asn Ala Gly Val Asn Val Pro Ala Ala Ser Met
            835                 840                 845

Tyr Asn Asn Ala Gly Glu Glu Gln Val Phe Lys Met Asp Leu Asn Asp
    850                 855                 860

Ser Arg Lys Ser Leu Ala Glu Lys Leu Lys Leu Arg Val Ser Gly Pro
865                 870                 875                 880

Gln Ser Gly Gln Ala Glu Ile Leu Leu Pro Arg Glu Thr Gln Phe Glu
                885                 890                 895

Val Val Ser Met Lys His Gln Gly Arg Asp Thr Tyr Val Leu Leu Gln
            900                 905                 910

Asp Ile Asn Gln Ser Ala Ala Thr His Arg Asn Val Arg Asn Thr Tyr
        915                 920                 925

Thr Gly Asn Phe Lys Ser Ser Ser Ala Asn
    930                 935
```